(12) United States Patent
Kim et al.

(10) Patent No.: US 11,871,661 B2
(45) Date of Patent: *Jan. 9, 2024

(54) ORGANIC LIGHT-EMITTING DEVICE

(71) Applicant: Samsung Display Co., Ltd., Yongin-si (KR)

(72) Inventors: Sung-Wook Kim, Yongin-si (KR); Myeong-Suk Kim, Yongin-si (KR); Hwan-Hee Cho, Yongin-si (KR); Jin-Soo Hwang, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 377 days.

This patent is subject to a terminal disclaimer.

(21) Appl. No.: 15/377,732

(22) Filed: Dec. 13, 2016

(65) Prior Publication Data

US 2017/0179404 A1 Jun. 22, 2017

(30) Foreign Application Priority Data

Dec. 17, 2015 (KR) .......................... 10-2015-0181074

(51) Int. Cl.
*H10K 85/60* (2023.01)
*C07D 491/107* (2006.01)
(Continued)

(52) U.S. Cl.
CPC ....... *H10K 85/657* (2023.02); *C07D 491/107* (2013.01); *C07D 495/10* (2013.01);
(Continued)

(58) Field of Classification Search
CPC .............. C07D 491/107; C07D 495/10; C09K 2211/1011; C09K 2211/1037;
(Continued)

(56) References Cited

U.S. PATENT DOCUMENTS 6,251,531 B1 6/2001 Enokida et al.
7,635,526 B2 12/2009 Stossel et al.
(Continued)

FOREIGN PATENT DOCUMENTS

CN 100481574 C 4/2009
CN 103087068 A 5/2013
(Continued)

OTHER PUBLICATIONS

Gong, et al. "Highly efficient blue OLED based on 9-anthracene-spirobenzofluorene derivatives as host materials." Journal of Materials Chemistry, 20.47 (2010): 10735-10746.
(Continued)

*Primary Examiner* — Sean M DeGuire
(74) *Attorney, Agent, or Firm* — Lewis Roca Rothgerber Christie LLP

(57) ABSTRACT

An organic light-emitting device includes: a first electrode; a second electrode facing the first electrode; and an organic layer between the first electrode and the second electrode, the organic layer including an emission layer, wherein the organic layer includes a first compound represented by Formula 1 and a second compound represented by Formula 501. The organic light-emitting device including the first
(Continued)

compound and the second compound may have low driving voltage, high efficiency, and high luminance.

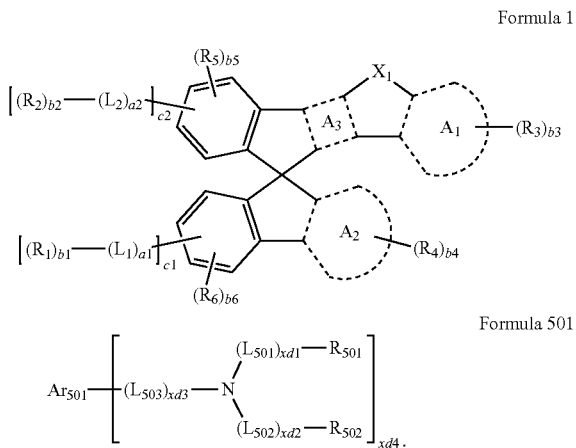

Formula 1

Formula 501

17 Claims, 4 Drawing Sheets

(51) Int. Cl.
C07D 495/10 (2006.01)
C09K 11/02 (2006.01)
C09K 11/06 (2006.01)
H10K 50/11 (2023.01)
H10K 50/15 (2023.01)
H10K 50/16 (2023.01)

(52) U.S. Cl.
CPC .......... C09K 11/025 (2013.01); C09K 11/06 (2013.01); H10K 85/615 (2023.02); H10K 85/626 (2023.02); H10K 85/633 (2023.02); C09K 2211/1007 (2013.01); C09K 2211/1011 (2013.01); C09K 2211/1014 (2013.01); C09K 2211/1033 (2013.01); C09K 2211/1037 (2013.01); C09K 2211/1048 (2013.01); C09K 2211/1051 (2013.01); C09K 2211/1092 (2013.01); C09K 2211/1096 (2013.01); H10K 50/11 (2023.02); H10K 50/15 (2023.02); H10K 50/16 (2023.02); H10K 85/622 (2023.02)

(58) Field of Classification Search
CPC .... C09K 2211/1048; C09K 2211/1051; H01L 51/0054; H10K 85/622
See application file for complete search history.

(56) References Cited

U.S. PATENT DOCUMENTS

| | | |
|---|---|---|
| 8,269,317 B2 | 9/2012 | Alleyne |
| 8,901,298 B2 | 12/2014 | Parham et al. |
| 8,987,462 B2 | 3/2015 | Kim et al. |
| 9,126,970 B2 | 9/2015 | Pflumm et al. |
| 9,288,869 B2 | 3/2016 | Han et al. |
| 9,722,191 B2 | 8/2017 | Kim et al. |
| 9,818,948 B2 | 11/2017 | Jatsch et al. |
| 9,837,617 B2 | 12/2017 | Pfister et al. |
| 10,134,997 B2 | 11/2018 | Kim et al. |
| 10,186,666 B2 | 1/2019 | Kim et al. |
| 10,411,195 B2* | 9/2019 | Kim .................. H01L 51/0073 |
| 10,693,076 B2 | 6/2020 | Hwang et al. |
| 2003/0072966 A1* | 4/2003 | Hosokawa ............ C07C 211/58 564/426 |
| 2004/0137270 A1* | 7/2004 | Seo ........................ C09K 11/06 428/690 |
| 2004/0197600 A1 | 10/2004 | Thompson et al. |
| 2006/0024522 A1 | 2/2006 | Thompson |
| 2007/0009758 A1 | 1/2007 | Funahashi |
| 2008/0154040 A1 | 6/2008 | Kosuge |
| 2008/0242871 A1 | 10/2008 | Kawakami et al. |
| 2009/0108737 A1 | 4/2009 | Kwong et al. |
| 2009/0124805 A1 | 5/2009 | Alleyne |
| 2009/0230857 A1 | 9/2009 | Choi et al. |
| 2009/0278118 A1 | 11/2009 | Ohrui et al. |
| 2010/0327270 A1 | 12/2010 | Buesing et al. |
| 2011/0037062 A1 | 2/2011 | Fukumatsu et al. |
| 2011/0112275 A1 | 5/2011 | Parham et al. |
| 2012/0018717 A1 | 1/2012 | Kim et al. |
| 2012/0080670 A1 | 4/2012 | Park et al. |
| 2012/0091885 A1 | 4/2012 | Kim et al. |
| 2012/0097899 A1 | 4/2012 | Parham et al. |
| 2012/0097924 A1 | 4/2012 | Kim et al. |
| 2012/0104379 A1 | 5/2012 | Kawakami et al. |
| 2012/0112174 A1 | 5/2012 | Lee et al. |
| 2012/0138914 A1 | 6/2012 | Kawamura et al. |
| 2012/0175561 A1 | 7/2012 | Franz et al. |
| 2012/0181922 A1 | 7/2012 | Kawamura et al. |
| 2012/0235123 A1 | 9/2012 | Lee et al. |
| 2013/0092913 A1 | 4/2013 | Nishimura et al. |
| 2013/0105769 A1 | 5/2013 | Lim et al. |
| 2013/0200350 A1 | 8/2013 | Sawada et al. |
| 2013/0240796 A1 | 9/2013 | Parham et al. |
| 2013/0256645 A1 | 10/2013 | Min et al. |
| 2013/0341599 A1 | 12/2013 | Xia et al. |
| 2014/0131664 A1 | 5/2014 | Yen et al. |
| 2014/0151647 A1 | 6/2014 | Mizuki et al. |
| 2014/0225040 A1* | 8/2014 | Parham ............... C07D 403/04 544/70 |
| 2014/0225046 A1 | 8/2014 | Jatsch et al. |
| 2014/0306197 A1 | 10/2014 | Kim et al. |
| 2014/0367647 A1 | 12/2014 | Kim et al. |
| 2015/0021563 A1 | 1/2015 | Kim et al. |
| 2015/0021585 A1 | 1/2015 | Yu et al. |
| 2015/0060785 A1 | 3/2015 | Kim et al. |
| 2015/0060808 A1 | 3/2015 | Kim et al. |
| 2015/0311450 A1 | 10/2015 | Park et al. |
| 2015/0318478 A1 | 11/2015 | Pflumm et al. |
| 2016/0043330 A1 | 2/2016 | Kim et al. |
| 2016/0126475 A1 | 5/2016 | Lee et al. |
| 2016/0126479 A1 | 5/2016 | Hwang et al. |
| 2016/0190466 A1 | 6/2016 | Pfister et al. |
| 2016/0214942 A1 | 7/2016 | Parham et al. |
| 2016/0218300 A1 | 7/2016 | Xia et al. |
| 2016/0293848 A1 | 10/2016 | Kim et al. |
| 2016/0308147 A1* | 10/2016 | Parham ............... C09K 11/025 |
| 2017/0062729 A1* | 3/2017 | Cha ........................ C07C 211/61 |
| 2017/0162801 A1* | 6/2017 | Cho .................... H01L 51/0074 |
| 2017/0179404 A1 | 6/2017 | Kim et al. |
| 2017/0346009 A1 | 11/2017 | Yokoyama et al. |
| 2017/0346015 A1 | 11/2017 | Hayashi et al. |
| 2017/0352813 A1 | 12/2017 | Duan et al. |
| 2018/0006245 A1 | 1/2018 | Pfister et al. |
| 2018/0208836 A1 | 7/2018 | Kuma et al. |

FOREIGN PATENT DOCUMENTS

| | | |
|---|---|---|
| CN | 103718316 A | 4/2014 |
| CN | 103842339 A | 6/2014 |
| JP | 2010114180 A | 5/2010 |
| KR | 10-2008-0096733 A | 11/2008 |
| KR | 10-2009-0011487 A | 2/2009 |
| KR | 10-2009-0098646 A | 9/2009 |
| KR | 10-2009-0117326 A | 11/2009 |
| KR | 10-2010-0106026 | 10/2010 |
| KR | 10-2010-0110895 A | 10/2010 |
| KR | 10-2010-0121378 A | 11/2010 |
| KR | 10-2010-0130197 A | 12/2010 |
| KR | 10-2011-0002156 A | 1/2011 |
| KR | 10-2011-0007124 A | 1/2011 |
| KR | 10-2011-0021487 A | 3/2011 |

(56) References Cited

FOREIGN PATENT DOCUMENTS

| | | |
|---|---|---|
| KR | 10-2011-0032373 A | 3/2011 |
| KR | 10-2011-0068330 | 6/2011 |
| KR | 10-2011-0088378 A | 8/2011 |
| KR | 10-2012-0006000 A | 1/2012 |
| KR | 10-2012-0034140 | 4/2012 |
| KR | 10-2012-0038402 | 4/2012 |
| KR | 10-2012-0043623 | 5/2012 |
| KR | 10-2012-0060611 | 6/2012 |
| KR | 10-2012-0078301 | 7/2012 |
| KR | 10-2012-0089223 | 8/2012 |
| KR | 10-2012-0089223 A | 8/2012 |
| KR | 10-2012-0117622 | 10/2012 |
| KR | 20120135837 A | 12/2012 |
| KR | 10-2013-0011405 A | 1/2013 |
| KR | 10-2013-0042865 A | 4/2013 |
| KR | 10-2013-0051807 A | 5/2013 |
| KR | 10-2013-0077470 A | 7/2013 |
| KR | 10-2013-0122602 | 11/2013 |
| KR | 10-1381505 B1 | 3/2014 |
| KR | 10-2014-0054132 A | 5/2014 |
| KR | 10-2014-0069199 A | 6/2014 |
| KR | 10-2014-0088003 | 7/2014 |
| KR | 10-2014-0104895 | 8/2014 |
| KR | 10-2014-0105913 A | 9/2014 |
| KR | 10-2015-0006802 A | 1/2015 |
| KR | 10-2015-0025529 A | 3/2015 |
| KR | 10-2015-0113642 A | 10/2015 |
| KR | 10-2015-0128583 A | 11/2015 |
| KR | 10-2015-0132660 A | 11/2015 |
| KR | 10-2016-0053423 A | 5/2016 |
| KR | 10-2016-0119904 A | 10/2016 |
| WO | WO 2010/110554 A2 | 9/2010 |
| WO | WO 2010/136109 A1 | 12/2010 |
| WO | WO 2011/025282 A2 | 3/2011 |
| WO | WO 2011/037380 A2 | 10/2011 |
| WO | WO 2013/100464 A1 | 7/2013 |
| WO | WO-2013100464 A1 * | 7/2013 ......... H01L 51/0073 |
| WO | WO 2014/007564 A1 | 1/2014 |
| WO | WO 2014/104600 A1 | 7/2014 |
| WO | WO-2014104600 A1 * | 7/2014 ........... C07D 209/86 |
| WO | WO 2014/129846 A1 | 8/2014 |
| WO | WO-2014185751 A1 * | 11/2014 ........... C07D 405/04 |
| WO | WO 2015/012618 A1 | 1/2015 |
| WO | 2015/022051 A1 | 2/2015 |
| WO | WO 2015/053463 A1 | 4/2015 |
| WO | WO 2015/090504 A2 | 6/2015 |
| WO | WO 2016/017919 A2 | 2/2016 |

OTHER PUBLICATIONS

U.S. Office Action dated May 15, 2018, issued in U.S. Appl. No. 15/098,258 (23 pages).
U.S. Advisory Action dated Feb. 5, 2019, issued in U.S. Appl. No. 15/098,258 (4 pages).
U.S. Office Action dated May 7, 2019, issued in U.S. Appl. No. 15/098,258 (26 pages).
Machine Translation of KR 2013/0122602 A.
U.S. Final Office Action dated Nov. 27, 2018, issued in U.S. Appl. No. 15/098,258 (18 pages).
U.S. Advisory Action dated Jul. 15, 2020, issued in U.S. Appl. No. 15/098,258 (4 pages).
Machine translation for KR 10-2012-0078301 A (publication date Jul. 2012).
Machine Translation of WO-2014104600-A1.
Machine Translation of WO-2014129846-A1.
Office Action dated Nov. 15, 2019, issued in U.S. Appl. No. 15/098,258 (28 pages).
U.S. Final Office action dated Apr. 30, 2020, issued in U.S. Appl. No. 15/098,258 (26 pages)
Cheuk-Lam Ho, et al., ""Small-Molecular blue phosphorescent dyes for organic light-emitting devices"", New J. Chem, 2013,37, 1665-1683 (Only abstract enclosed).
Office action dated Nov. 17, 2020 in U.S. Appl. No. 15/098,258, 28 pages.
Advisory Action for U.S. Appl. No. 14/457,533 dated Jan. 30, 2017, 3 pages.
Advisory Action for U.S. Appl. No. 14/457,533 dated Nov. 15, 2017, 3 pages.
Final Office Action for U.S. Appl. No. 14/253,830 dated Jul. 30, 2018, 12 pages.
Final Office Action for U.S. Appl. No. 14/253,830 dated Sep. 15, 2017, 10 pages.
Final Office Action for U.S. Appl. No. 14/457,533 dated Jul. 24, 2017, 10 pages.
Final Office Action for U.S. Appl. No. 14/457,533 dated Nov. 15, 2016, 14 pages.
Final Office Action for U.S. Appl. No. 15/098,258 dated Jun. 2, 2021, 25 pages.
Final Office Action for U.S. Appl. No. 15/703,770 dated Dec. 2, 2019, 10 pages.
Notice of Allowance for U.S. Appl. No. 14/036,574 dated Nov. 7, 2014, 8 pages.
Notice of Allowance for U.S. Appl. No. 14/253,830 dated May 2, 2019, 8 pages.
Notice of Allowance for U.S. Appl. No. 14/457,533 dated Jul. 5, 2018, 8 pages.
Notice of Allowance for U.S. Appl. No. 14/661,427 dated Mar. 30, 2017, 8 pages.
Notice of Allowance for U.S. Appl. No. 14/963,274 dated Aug. 29, 2018, 10 pages.
Notice of Allowance for U.S. Appl. No. 15/703,770 dated Feb. 10, 2020, 6 pages.
Office Action for U.S. Appl. No. 14/253,830 dated Feb. 7, 2018, 12 pages.
Office Action for U.S. Appl. No. 14/253,830 dated Mar. 7, 2017, 9 pages.
Office Action for U.S. Appl. No. 14/253,830 dated Nov. 26, 2018, 12 pages.
Office Action for U.S. Appl. No. 14/457,533 dated Feb. 9, 2018, 11 pages.
Office Action for U.S. Appl. No. 14/457,533 dated Jun. 22, 2016, 10 pages.
Office Action for U.S. Appl. No. 14/457,533 dated Mar. 9, 2017, 9 pages.
Office Action for U.S. Appl. No. 14/963,274 dated Mar. 16, 2018, 11 pages.
Office Action for U.S. Appl. No. 15/098,258 dated Nov. 17, 2020, 28 pages.
Office Action for U.S. Appl. No. 15/703,770 dated Jun. 3, 2019, 10 pages.
Restriction Requirement for U.S. Appl. No. 14/963,274 dated Sep. 27, 2017, 6 pages.
Office Action for U.S. Appl. No. 15/098,258 dated Nov. 10, 2022, 18 pages.
Korean Notice of Allowance for KR Patent Appiication N0w 10-2015-0048326 dated Oct. 5, 2022, 3 pages.
Final Rejection for U.S. Appl. No. 15/098,258 dated Apr. 28, 2023, pages.
U.S. Notice of Allowance dated Oct. 23, 2023, issued in U.S. Appl. No. 15/098,258 (9 pages).

\* cited by examiner

| 190 |
|-----|
| 150 |
| 110 |

| 190 |
|-----|
| 150 |
| 110 |
| 210 |

| 220 |
|---|
| 190 |
| 150 |
| 110 |

| |
|---|
| 220 |
| 190 |
| 150 |
| 110 |
| 210 |

ORGANIC LIGHT-EMITTING DEVICE

CROSS-REFERENCE TO RELATED APPLICATION

This application claims priority to and the benefit of Korean Patent Application No. 10-2015-0181074, filed on Dec. 17, 2015, in the Korean Intellectual Property Office, the entire content of which is incorporated herein by reference.

BACKGROUND

1. Field

One or more aspects of embodiments of the present disclosure relate to an organic light-emitting device.

2. Description of the Related Art

Organic light-emitting devices are self-emission devices that have wide viewing angles, high contrast ratios, short response times, and excellent brightness, driving voltage, and response speed characteristics, and can produce full-color images.

The organic light-emitting device may include a first electrode disposed (e.g., positioned) on a substrate, and a hole transport region, an emission layer, an electron transport region, and a second electrode, which are sequentially disposed on the first electrode. Holes provided from, for example, the first electrode may move toward the emission layer through the hole transport region, and electrons provided from, for example, the second electrode may move toward the emission layer through the electron transport region. Carriers, such as holes and electrons, may then recombine in the emission layer to produce excitons. These excitons transit from an excited state to a ground state, thereby generating light.

SUMMARY

One or more aspects of embodiments of the present disclosure are directed towards an organic light-emitting device that includes a first compound and a second compound represented by the Formulae provided herein.

Additional aspects will be set forth in part in the description which follows and, in part, will be apparent from the description, or may be learned by practice of the presented embodiments.

According to one or more embodiments, an organic light-emitting device includes: a first electrode; a second electrode facing the first electrode; and an organic layer between the first electrode and the second electrode, the organic layer including an emission layer, wherein the organic layer includes a first compound represented by Formula 1 and a second compound represented by Formula 501:

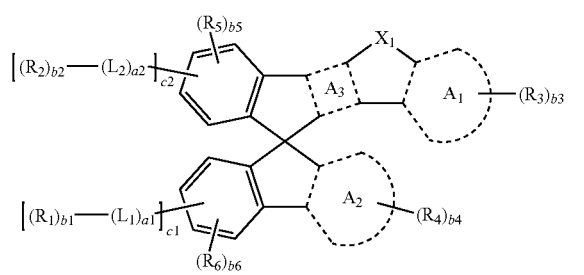

Formula 1

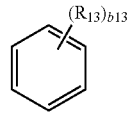

Formula 2A

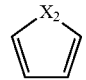

Formula 2B

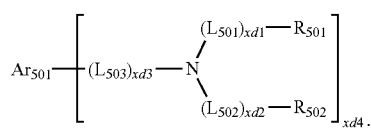

Formula 501

In Formulae 1, 2A, 2B, and 501, ring $A_1$ and ring $A_2$ may each independently be selected from a benzene ring, a naphthalene ring, a pyridine ring, a pyrimidine ring, a pyrazine ring, a quinoline ring, an isoquinoline ring, a quinoxaline ring, a quinazoline ring, and a cinnoline ring, ring $A_3$ may be a group represented by Formula 2A or a group represented by Formula 2B, $X_1$ may be N-[$(L_{11})_{a11}$-$(R_{11})_{b11}$], O, or S, $X_2$ may be N-[$(L_{12})_{a12}$-$(R_{12})_{b12}$], O, or S, $Ar_{501}$ may be selected from a substituted or unsubstituted $C_5$-$C_{30}$ carbocyclic group and a substituted or unsubstituted $C_2$-$C_{30}$ heterocyclic group, $L_1$ and $L_2$ may each independently be a substituted or unsubstituted condensed polycyclic group having three or more carbocyclic groups condensed with each other, a1 and a2 may each independently be an integer selected from 1 to 5, wherein when a1 is two or more, two or more $L_1(s)$ may be identical to or different from each other; and when a2 is two or more, two or more $L_2(s)$ may be identical to or different from each other, $L_{11}$, $L_{12}$, and $L_{501}$ to $L_{503}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a11, a12, and xd1 to xd3 may each independently be an integer selected from 0 to 5, wherein when a11 is two or more, two or more $L_{11}(s)$ may be identical to or different from each other; when a12 is two or more, two or more $L_{12}(s)$ may be identical to or different from each other; when xd1 is two or more, two or more $L_{501}(s)$ may be identical to or different from each other; when xd2 is two or more, two or more $L_{502}(s)$ may be identical to or different from each other; and when xd3 is two or more, two or more $L_{503}(s)$ may be identical to or different from each other, $R_1$ to $R_6$, $R_{11}$ to $R_{13}$, $R_{501}$, and $R_{502}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), b1, b2, b5, b6, b11, and b12 may each independently be an integer selected from 0 to 4, b3 and b4 may each independently be an integer selected from 0 to 6, b13 may be 0, 1, or 2, c1 and c2 may each independently be an integer selected from 0 to 4, and the sum of c1 and c2 (c1+c2) may be 1 or greater, xd4 may be an integer selected from 1 to 6, and at least one substituent of the substituted condensed polycyclic group having three or more carbocyclic groups condensed with each other, the substituted $C_5$-$C_{30}$ carbocyclic group, the substituted $C_2$-$C_{30}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from the group consisting of:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_1$ to $Q_3$, $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

In the organic light-emitting device, the emission layer may include a host and a dopant, wherein the first compound may be included in the host, and the second compound may be included in the dopant.

BRIEF DESCRIPTION OF THE DRAWINGS

These and/or other aspects will become apparent and more readily appreciated from the following description of the embodiments, taken in conjunction with the accompanying drawings in which:

FIG. 1 is a schematic view of an organic light-emitting device according to an embodiment of the present disclosure;

FIG. 2 is a schematic view of an organic light-emitting device according to another embodiment of the present disclosure;

FIG. 3 is a schematic view of an organic light-emitting device according to another embodiment of the present disclosure; and FIG. 4 is a schematic view of an organic light-emitting device according to another embodiment of the present disclosure.

DETAILED DESCRIPTION

Reference will now be made in more detail to embodiments, examples of which are illustrated in the accompanying drawing, wherein like reference numerals refer to like elements throughout. In this regard, the present embodiments may have different forms and should not be construed as being limited to the descriptions set forth herein. Accordingly, the embodiments are merely described below, by referring to the drawing, to explain aspects of the present description. As used herein, the term "and/or" includes any and all combinations of one or more of the associated listed items. Expressions such as "at least one of," "one of," and "selected from," when preceding a list of elements, modify the entire list of elements and do not modify the individual elements of the list. Further, the use of "may" when describing embodiments of the present invention refers to "one or more embodiments of the present invention."

An organic light-emitting device according to an embodiment may include a first electrode; a second electrode facing the first electrode; and an organic layer between the first electrode and the second electrode, the organic layer including an emission layer, wherein the organic layer may include a first compound represented by Formula 1 and a second compound represented by Formula 501:

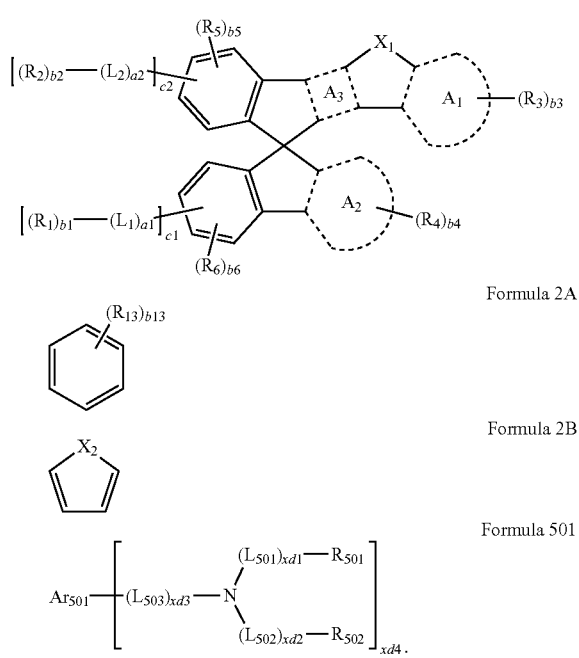

Formula 1

Formula 2A

Formula 2B

Formula 501

Ring $A_1$ and ring $A_2$ in Formula 1 may each be fused with a neighboring 5-membered ring, while sharing at least two ring-forming carbon atoms therewith. In Formula 1, ring $A_1$ and ring $A_2$ may each independently be selected from a benzene ring, a naphthalene ring, a pyridine ring, a pyrimidine ring, a pyrazine ring, a quinoline ring, an isoquinoline ring, a quinoxaline ring, a quinazoline ring, and a cinnoline ring.

For example, ring $A_1$ and ring $A_2$ in Formula 1 may each independently be selected from a benzene ring, a naphthalene ring, a pyridine ring, a quinoline ring, and an isoquinoline ring.

In various embodiments, in Formula 1,
ring $A_1$ may be a benzene ring or a pyridine ring; and ring $A_2$ may be selected from a benzene ring, a naphthalene ring, a pyridine ring, a quinoline ring, and an isoquinoline ring, or
ring $A_1$ may be selected from a naphthalene ring, a quinoline ring, and an isoquinoline ring; and ring $A_2$ may be a benzene ring or a pyridine ring,
but embodiments of the present disclosure are not limited thereto.

Ring $A_3$ in Formula 1 may be fused with two neighboring 5-membered rings, while sharing at least two ring-forming carbon atoms with each of the two neighboring 5-membered rings. In Formula 1, ring $A_3$ may be a group represented by Formula 2A or a group represented by Formula 2B:

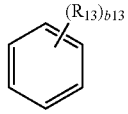

Formula 2A

Formula 2B $R_{13}$ and $b_{13}$ in Formula 2A and $X_2$ in Formula 2B are the same as described throughout the present specification.

In various embodiments, $A_3$ in Formula 1 may be a group represented by Formula 2A, but is not limited thereto.

$X_1$ in Formula 1 may be N-$[(L_{11})_{a11}$-$(R_{11})_{b11}]$, O, or S; and $X_2$ in Formula 2B may be N-$[(L_{12})_{a12}$-$(R_{12})_{b12}]$, O, or S.

For example, $X_1$ in Formula 1 may be O or S.

$Ar_{501}$ in Formula 501 may be selected from a substituted or unsubstituted $C_5$-$C_{30}$ carbocyclic group and a substituted or unsubstituted $C_2$-$C_{30}$ heterocyclic group.

For example, $Ar_{501}$ in Formula 501 may be a substituted or unsubstituted condensed polycyclic ring having three or more carbocyclic groups condensed (e.g., fused) with each other.

In various embodiments, $Ar_{501}$ in Formula 501 may selected from the group consisting of:
an indacene group, an acenaphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, a hexacene group, a pentacene group, a rubicene group, a coronene group, an ovalene group, a benzopyrene group, a benzochrysene group, a benzotriphenylene group, and a phenanthroline group; and
an indacene group, an acenaphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, a hexacene group, a pentacene group, a rubicene group, a coronene group, an ovalene group, a benzopyrene group, a benzochrysene group, a benzotriphenylene group, and a phenanthroline group, each substituted with at least one selected from deuterium, —F, —Cl, —Br, —I, a hydroxyl group, a cyano group, a nitro group, an am idino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$), wherein $Q_{31}$ to $Q_{33}$ may each independently be selected from a $C_1$-$C_{10}$ alkyl group, a $C_1$-$C_{10}$ alkoxy group, a phenyl group, and a naphthyl group.

In various embodiments, $Ar_{501}$ in Formula 501 may be selected from the group consisting of:

a fluorene group, a spiro-bifluorene group, a benzofluorene group, a dibenzofluorene group, an anthracene group, a fluoranthene group, a triphenylene group, a pyrene group, a chrysene group, a benzopyrene group, a benzochrysene group, and a benzotriphenylene group; and a fluorene group, a spiro-bifluorene group, a benzofluorene group, a dibenzofluorene group, an anthracene group, a fluoranthene group, a triphenylene group, a pyrene group, a chrysene group, a benzopyrene group, a benzochrysene group, and a benzotriphenylene group, each substituted with at least one selected from deuterium, —F, —Cl, —Br, —I, a hydroxyl group, a cyano group, a nitro group, an am idino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a naphthyl group, and —Si($Q_{31}$)($Q_{32}$)($Q_{33}$), wherein $Q_{31}$ to $Q_{33}$ may each independently be selected from a $C_1$-$C_{10}$ alkyl group, a $C_1$-$C_{10}$ alkoxy group, a phenyl group, and a naphthyl group.

$L_1$ and $L_2$ in Formula 1 may each independently be a substituted or unsubstituted condensed polycyclic group having three or more carbocyclic groups condensed (e.g., fused) with each other. In some embodiments, $L_1$ and $L_2$ each independently include carbon atoms as ring-forming atoms and do not include a heteroatom (e.g., N, O, S, P, or the like). Accordingly, $L_1$ and $L_2$ do not include groups that have less than three carbocyclic groups condensed with each other (e.g., $L_1$ and $L_2$ do not include a naphthylene group that has only two carbocyclic groups condensed with each other), or groups that include a heteroatom as a ring-forming atom (e.g., $L_1$ and $L_2$ do not include a pyridinylene group that includes N as a ring-forming atom).

In various embodiments, $L_1$ and $L_2$ in Formula 1 may each independently be selected from the group consisting of:

an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, and an ovelenylene group; and an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylere group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, and an ovalenylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$), wherein $Q_{31}$ to $Q_{33}$ may each independently be selected from a $C_1$-$C_{10}$ alkyl group, a $C_1$-$C_{10}$ alkoxy group, a phenyl group, and a naphthyl group.

In various embodiments, $L_1$ and $L_2$ in Formula 1 may each independently be selected from the group consisting of:

a phenalenylene group, a phenanthrenylene group, an anthracenylene group, a fluoranthenylene group, a triphenylenylene group, a pyrenylene group, a chrysenylene group, and a perylenylene group; and a phenalenylene group, a phenanthrenylene group, an anthracenylene group, a fluoranthenylene group, a triphenylenylene group, a pyrenylene group, a chrysenylene group, and a perylenylene group, each substituted with at least one selected from deuterium, —F, —Cl, —Br, —I, a hydroxyl group, a cyano group, a nitro group, an am idino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$), wherein $Q_{31}$ to $Q_{33}$ may each independently be selected from a $C_1$-$C_{10}$ alkyl group, a $C_1$-$C_{10}$ alkoxy group, a phenyl group, and a naphthyl group.

a1 and a2 in Formula 1 may each independently be an integer selected from 1 to 5, wherein when a1 is two or more, two or more $L_1$(s) may be identical to or different from each other, and when a2 is two or more, two or more $L_2$(s) may be identical to or different from each other. That is, in Formula 1, "$L_1$" is included in the group represented by *-[($L_1$)$_{a1}$-($R_1$)$_{b1}$] and "$L_2$" is included in the group represented by *-[($L_2$)$_{a2}$-($R_2$)$_{b2}$].

In various embodiments, a1 and a2 in Formula 1 may each independently be 1 or 2, or may each independently be 1, but a1 and a2 are not limited thereto.

$L_{11}$, $L_{12}$, and $L_{501}$ to $L_{503}$ in the Formulae described above may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

For example, $L_{11}$, $L_{12}$, and $L_{501}$ to $L_{503}$ may each independently be selected from the group consisting of:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$), wherein $Q_{31}$ to $Q_{33}$ may each independently be selected from a $C_1$-$C_{10}$ alkyl group, a $C_1$-$C_{10}$ alkoxy group, a phenyl group, and a naphthyl group.

In various embodiments, $L_1$ and $L_2$ may each independently be selected from groups represented by Formulae 3-8, 3-9, 3-25, and 3-35 to 3-41, and $L_{11}$, $L_{12}$, and $L_{501}$ to $L_{503}$ may each independently be selected from groups represented by Formulae 3-1 to 3-41:

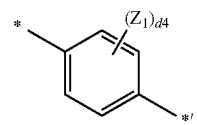

Formula 3-1

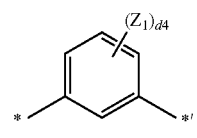

Formula 3-2

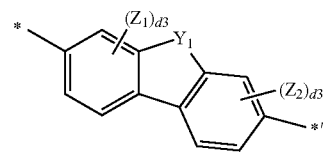

Formula 3-3

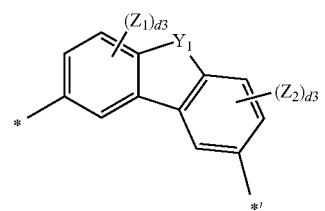

Formula 3-4

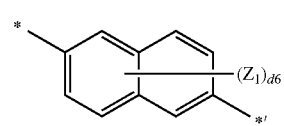

Formula 3-5

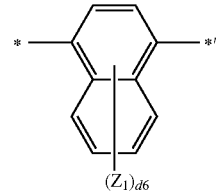

Formula 3-6

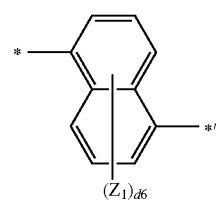

Formula 3-7

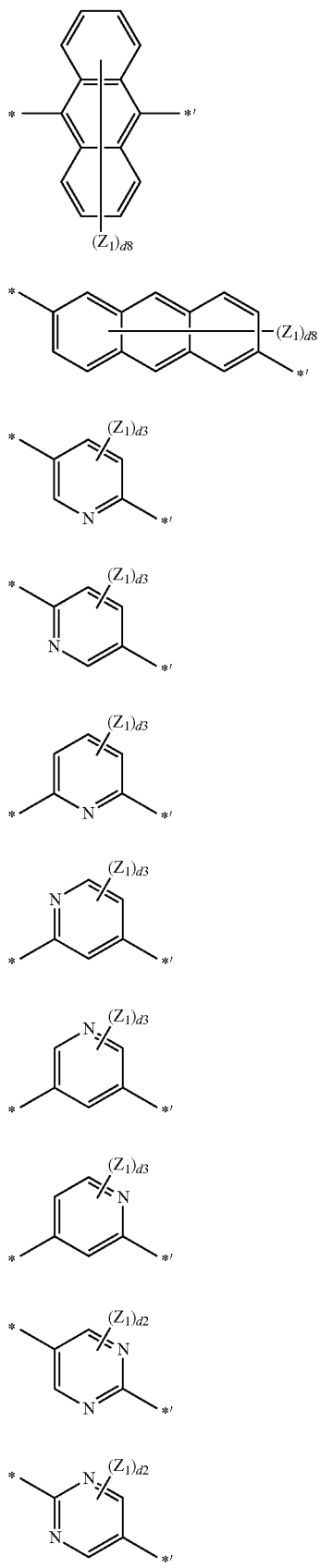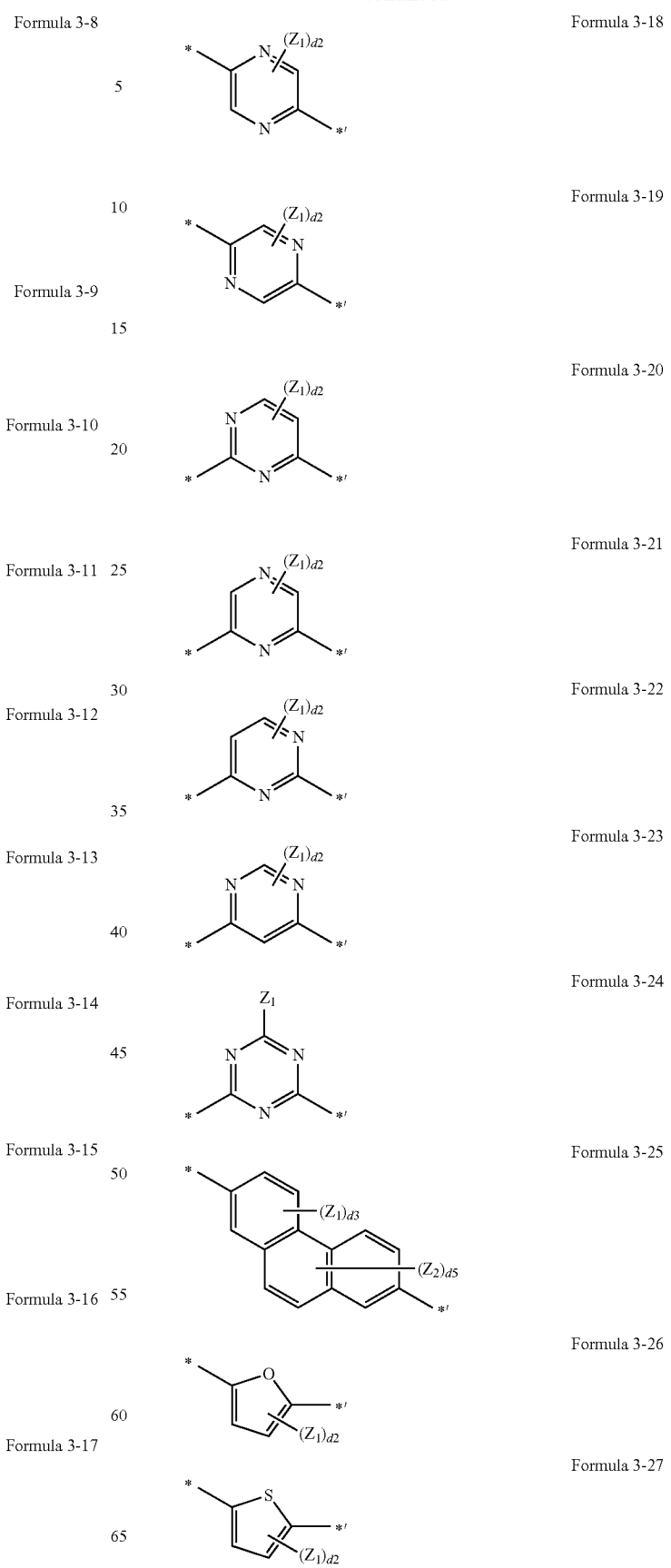

-continued
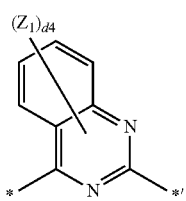
Formula 3-28
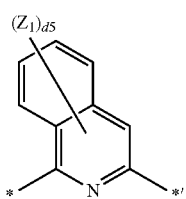
Formula 3-29
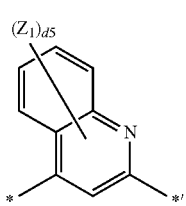
Formula 3-30
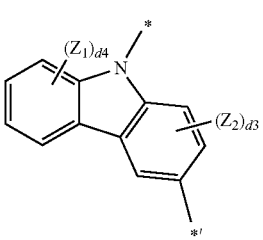
Formula 3-31
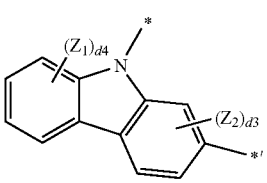
Formula 3-32
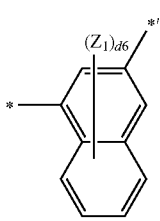
Formula 3-33
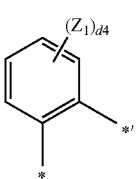
Formula 3-34
-continued
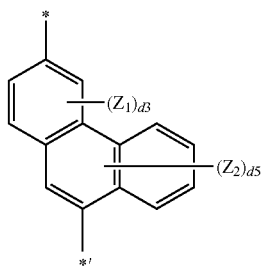
Formula 3-35
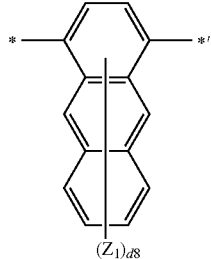
Formula 3-36
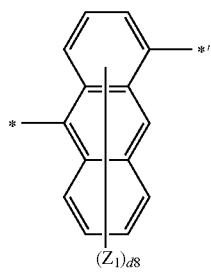
Formula 3-37
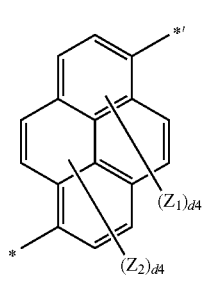
Formula 3-38
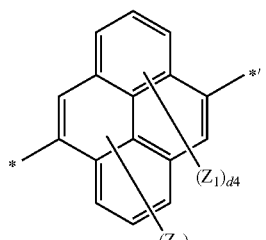
Formula 3-39

Formula 3-40

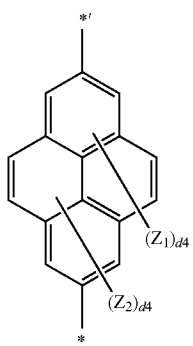

Formula 3-41

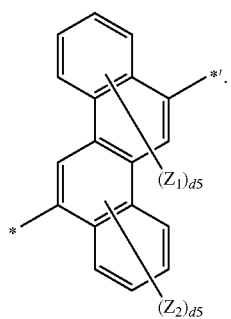

Formula 4-1
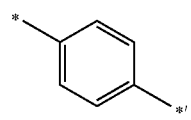

Formula 4-2
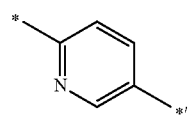

Formula 4-3
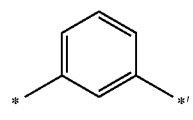

Formula 4-4
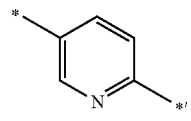

Formula 4-5
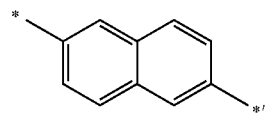

Formula 4-6
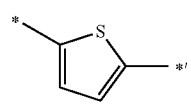

Formula 4-7
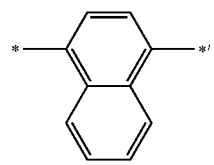

Formula 4-8
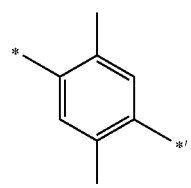

Formula 4-9
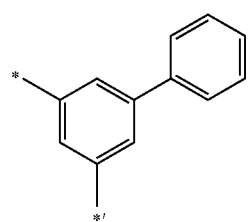

Formula 4-10
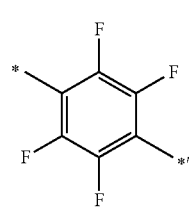

In Formulae 3-1 to 3-41, $Y_1$ may be selected from O, S, $C(Z_3)(Z_4)$, $N(Z_5)$, and $Si(Z_6)(Z_7)$, $Z_1$ to $Z_7$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —Si($Q_{31}$)($Q_{32}$)($Q_{33}$), wherein $Q_{31}$ to $Q_{33}$ may each independently be selected from a $C_1$-$C_{10}$ alkyl group, a $C_1$-$C_{10}$ alkoxy group, a phenyl group, and a naphthyl group, d2 may be an integer selected from 0 to 2, d3 may be an integer selected from 0 to 3, d4 may be an integer selected from 0 to 4, d5 may be an integer selected from 0 to 5, d6 may be an integer selected from 0 to 6, d8 may be an integer selected from 0 to 8, and

* and *' each independently indicate a binding site to a neighboring atom.

In various embodiments, $L_1$ and $L_2$ may each independently be selected from groups represented by Formulae 4-11, 4-13, 4-27, and 4-29 to 4-35, and $L_{11}$, $L_{12}$, and $L_{501}$ to $L_{503}$ may each independently be selected from Formulae 4-1 to 4-35, but $L_1$, $L_2$ $L_{11}$, $L_{12}$, and $L_{501}$ to $L_{503}$ are not limited thereto:

-continued
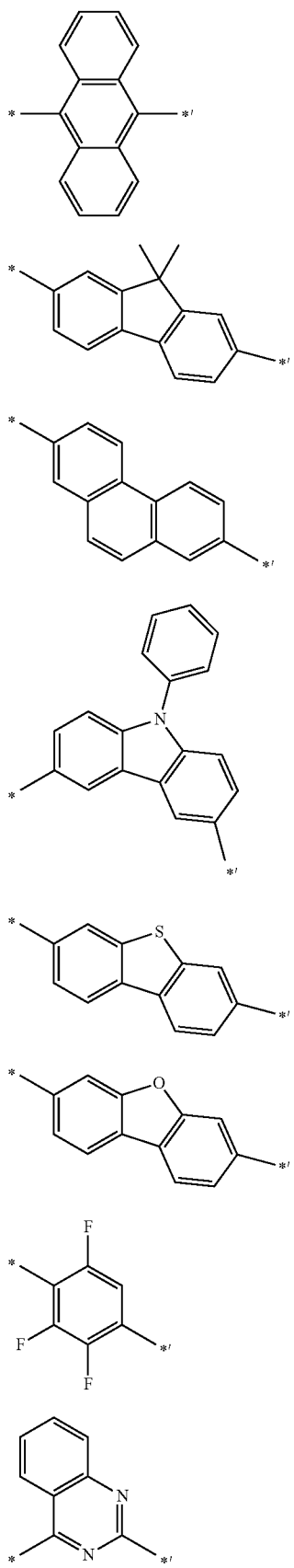
Formula 4-11
Formula 4-12
Formula 4-13
Formula 4-14
Formula 4-15
Formula 4-16
Formula 4-17
Formula 4-18
Formula 4-19
Formula 4-20
Formula 4-21
Formula 4-22
Formula 4-23
Formula 4-24
Formula 4-25
Formula 4-26

-continued

Formula 4-27
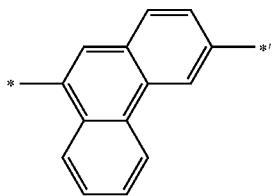

Formula 4-28
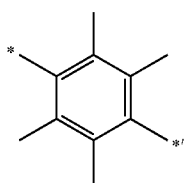

Formula 4-29
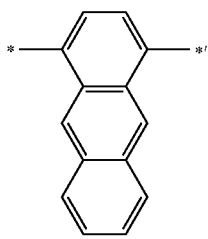

Formula 4-30
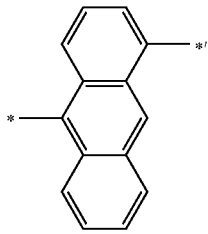

Formula 4-31
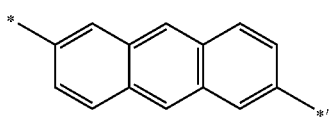

Formula 4-32
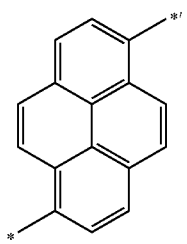

Formula 4-33
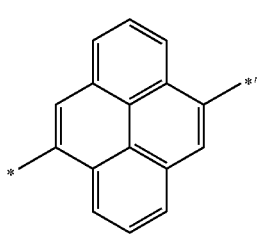

-continued

Formula 4-34
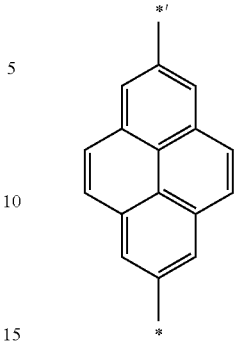

Formula 4-35
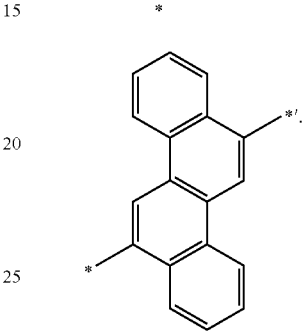

In Formulae 4-1 to 4-35, * and *' each independently indicate a binding atom to a neighboring atom, and "D" may refer to deuterium.

a11, a12, and xd1 to xd3 may each independently be an integer selected from 0 to 5, wherein when a11 is two or more, two or more $L_{11}$(s) may be identical to or different from each other; when a12 is two or more, two or more $L_{12}$(s) may be identical to or different from each other; when xd1 is two or more, two or more $L_{501}$(s) may be identical to or different from each other; when xd2 is two or more, two or more $L_{502}$(s) may be identical to or different from each other; and xd3 is two or more, two or more $L_{503}$(s) may be identical to or different from each other.

In various embodiments, a11, a12, and xd1 to xd3 in the Formulae described above may each independently be 0, 1, or 2, or may each independently be 0 or 1, but are not limited thereto.

$R_1$ to $R_6$, $R_{11}$ to $R_{13}$, $R_{501}$, and $R_{502}$ in the Formulae described above may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), wherein $Q_1$ to $Q_3$ are as described herein.

For example, $R_1$ to $R_6$, $R_{11}$ to $R_{13}$, $R_{501}$, and $R_{502}$ in the Formulae described above may each independently be selected from the group consisting of:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, and a hydrazino group, and a hydrazono group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$), and —Si($Q_1$)($Q_2$)($Q_3$), wherein $Q_1$ to $Q_3$ and $Q_{31}$ to $Q_{33}$ may each independently be selected from a $C_1$-$C_{10}$ alkyl group, a $C_1$-$C_{10}$ alkoxy group, a phenyl group, and a naphthyl group.

In various embodiments, $R_1$ to $R_6$, $R_{11}$ to $R_{13}$, and $R_{501}$ and $R_{502}$ in the Formulae described above may each independently be selected from the group consisting of:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, an imidazopyrimidinyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ may each independently be selected from a $C_1$-$C_{10}$ alkyl group, a $C_1$-$C_{10}$ alkoxy group, a phenyl group, and a naphthyl group.

In various embodiments, $R_1$ to $R_6$, $R_{11}$ to $R_{13}$, and $R_{501}$ and $R_{502}$ in the Formulae described above may each independently be selected from hydrogen, deuterium, —F, —Cl, —Br, —I, a hydroxyl group, a cyano group, a nitro group, an amidino group, a hydrazino group, a hydrazono group, a $C_1$-$C_{10}$ alkyl group, a $C_1$-$C_{10}$ alkoxy group, a group represented by any of Formulae 5-1 to 5-75, and —Si($Q_1$)($Q_2$)($Q_3$), wherein $Q_1$ to $Q_3$ may each independently be selected from a $C_1$-$C_{10}$ alkyl group, a $C_1$-$C_{10}$ alkoxy group, a phenyl group, and a naphthyl group:

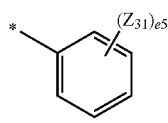

Formula 5-1

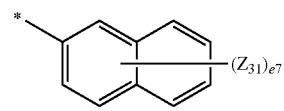

Formula 5-2

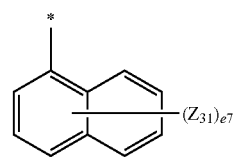

Formula 5-3

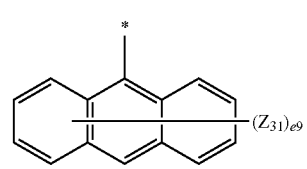

Formula 5-4

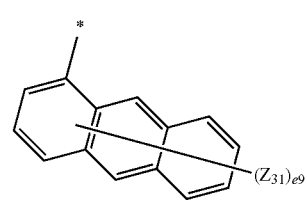

Formula 5-5

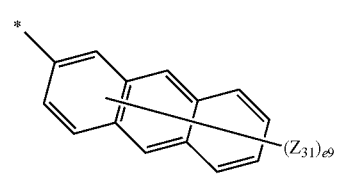

Formula 5-6

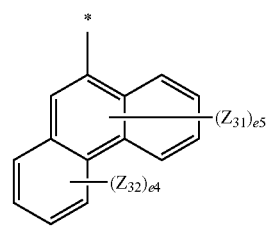

Formula 5-7

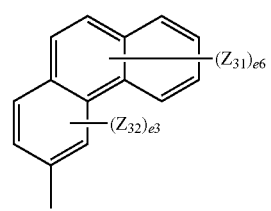

Formula 5-8

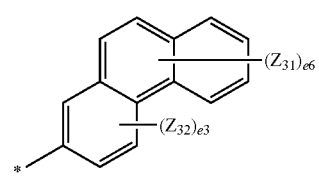

Formula 5-9

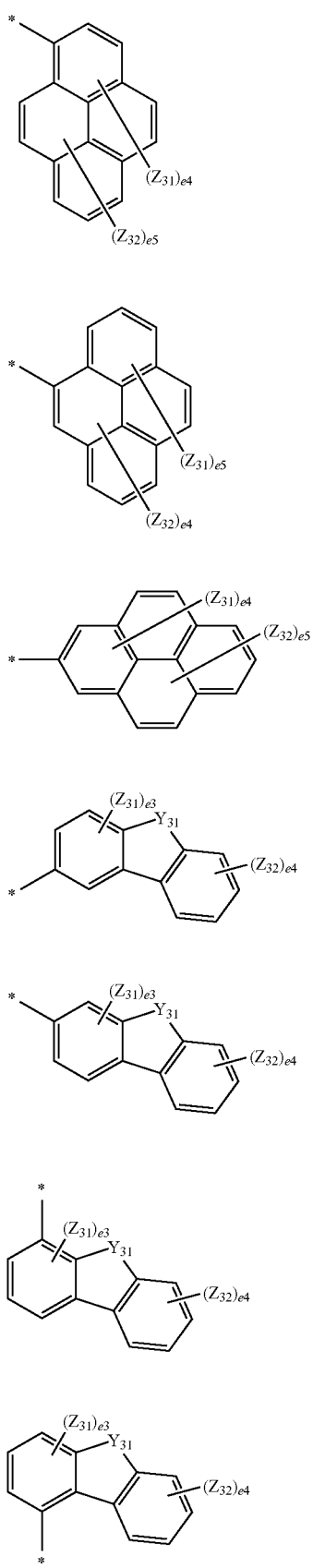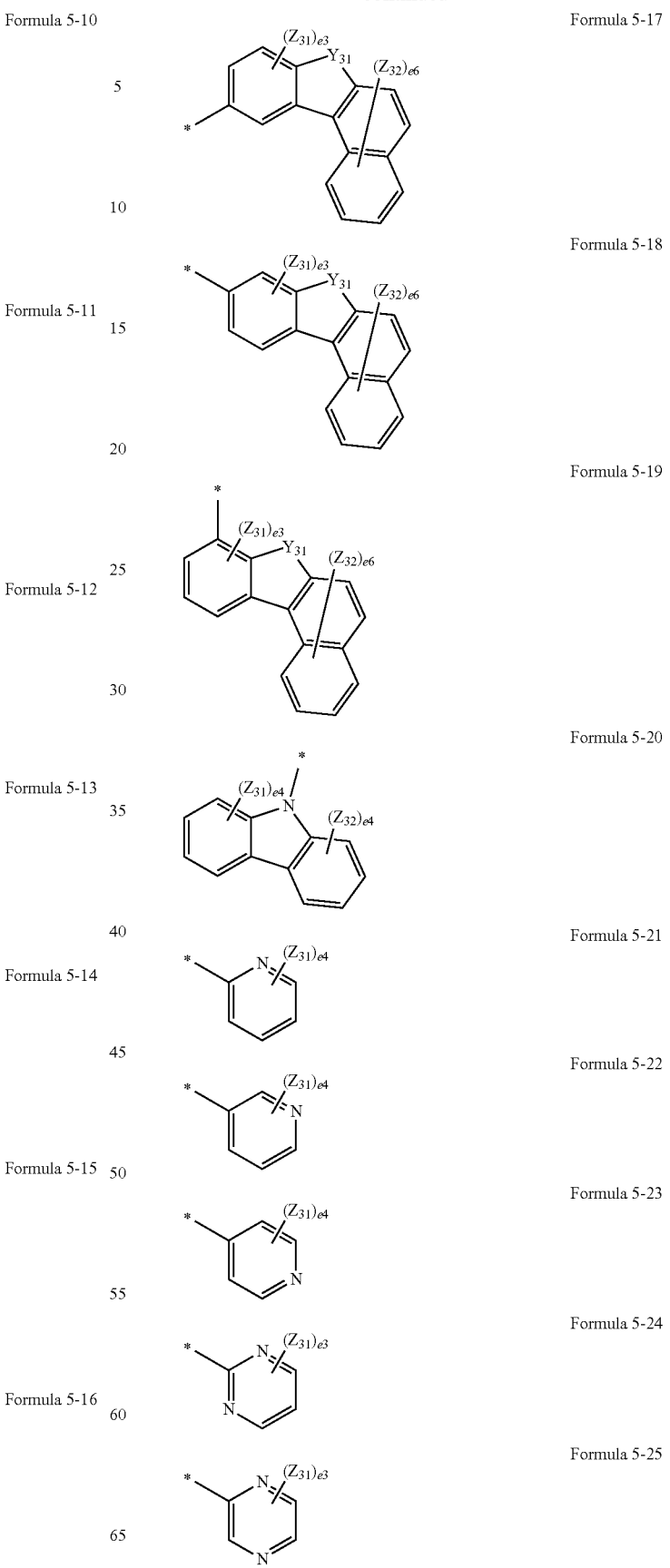

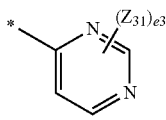
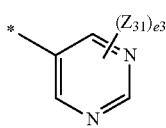
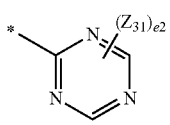
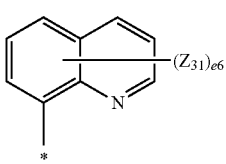
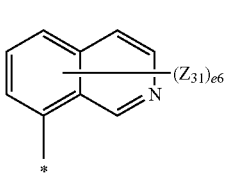
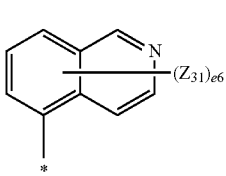
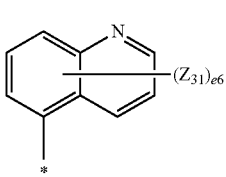
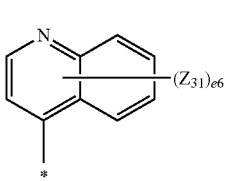
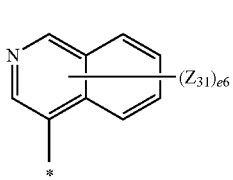
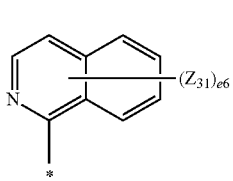
Formula 5-26
Formula 5-27
Formula 5-28
Formula 5-29
Formula 5-30
Formula 5-31
Formula 5-32
Formula 5-33
Formula 5-34
Formula 5-35
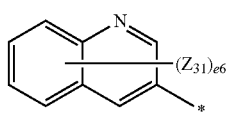 Formula 5-36
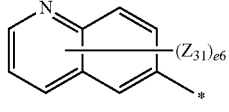 Formula 5-37
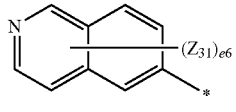 Formula 5-38
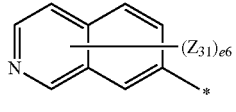 Formula 5-39
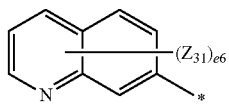 Formula 5-40
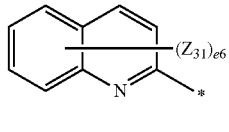 Formula 5-41
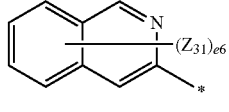 Formula 5-42
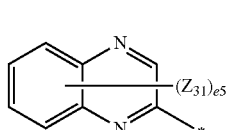 Formula 5-43
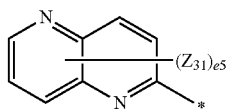 Formula 5-44
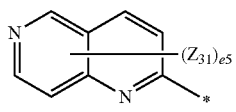 Formula 5-45
Formula 5-46
Formula 5-47

| | |
|---|---|
| 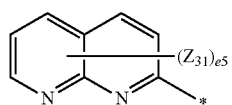 Formula 5-48 | 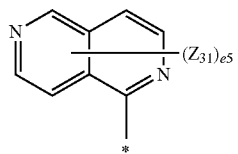 Formula 5-59 |
| 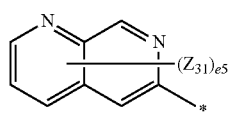 Formula 5-49 | 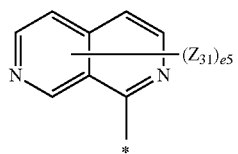 Formula 5-60 |
| 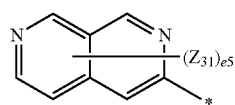 Formula 5-50 | 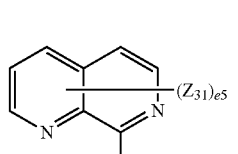 Formula 5-61 |
| 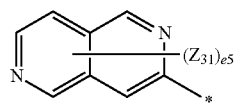 Formula 5-51 | 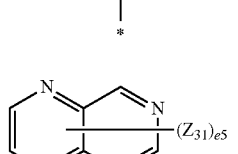 Formula 5-62 |
| 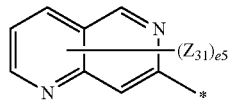 Formula 5-52 | 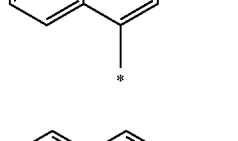 Formula 5-63 |
| 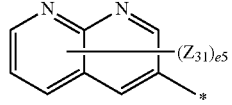 Formula 5-53 | 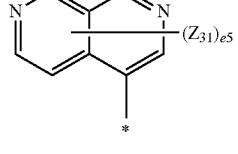 Formula 5-64 |
| 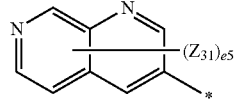 Formula 5-54 | 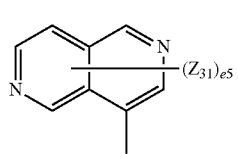 Formula 5-65 |
| 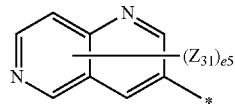 Formula 5-55 | 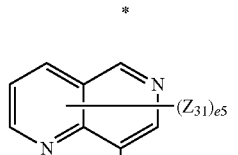 Formula 5-66 |
| 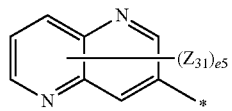 Formula 5-56 | 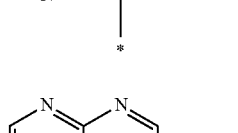 Formula 5-67 |
| 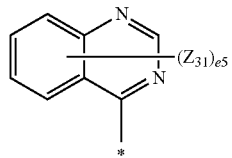 Formula 5-57 | 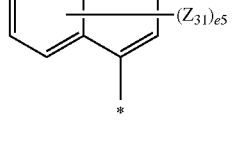 |
| 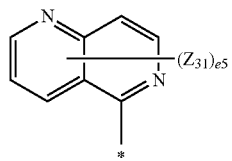 Formula 5-58 | 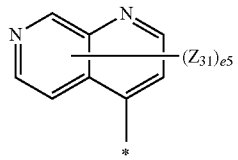 |

-continued

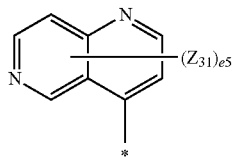
Formula 5-68

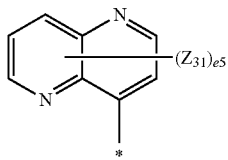
Formula 5-69

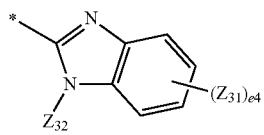
Formula 5-70

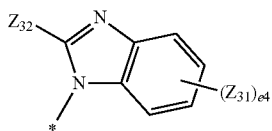
Formula 5-71

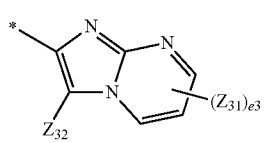
Formula 5-72

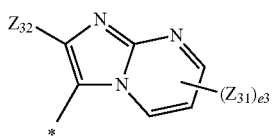
Formula 5-73

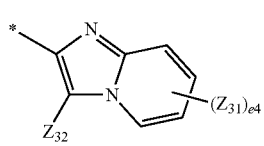
Formula 5-74

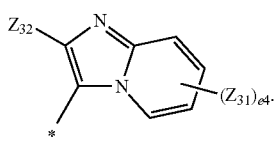
Formula 5-75

In Formulae 5-1 to 5-75, $Y_{31}$ may be selected from O, S, $C(Z_{33})(Z_{34})$, $N(Z_{35})$, and $Si(Z_{36})(Z_{37})$, $Z_{31}$ to $Z_{37}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a biphenyl group, a terphenyl group, and —$Si(Q_{31})(Q_{32})(Q_{33})$, wherein $Q_{31}$ to $Q_{33}$ may each independently be selected from a $C_1$-$C_{10}$ alkyl group, a $C_1$-$C_{10}$ alkoxy group, a phenyl group, and a naphthyl group, e2 may be an integer selected from 0 to 2, e3 may be an integer selected from 0 to 3, e4 may be an integer selected from 0 to 4, e5 may be an integer selected from 0 to 5, e6 may be an integer selected from 0 to 6, e7 may be an integer selected from 0 to 7, e9 may be an integer selected from 0 to 9, and

* indicates a binding site to a neighboring atom.

In various embodiments, $R_1$ to $R_6$, $R_{11}$ to $R_{13}$, $R_{501}$, and $R_{502}$ in the Formulae described above may each independently be selected from hydrogen, deuterium, —F, —Cl, —Br, —I, a hydroxyl group, a cyano group, a nitro group, an amidino group, a hydrazino group, a hydrazono group, a $C_1$-$C_{10}$ alkyl group, a $C_1$-$C_{10}$ alkoxy group, a group represented by any of Formulae 6-1 to 6-43, a group represented by any of Formulae 10-1 to 10-117, and —$Si(Q_1)(Q_2)(Q_3)$, wherein $Q_1$ to $Q_3$ may each independently be selected from a $C_1$-$C_{10}$ alkyl group, a $C_1$-$C_{10}$ alkoxy group, a phenyl group, and a naphthyl group, but $R_1$ to $R_6$, $R_{11}$ to $R_{13}$, $R_{501}$, and $R_{502}$ are not limited thereto:

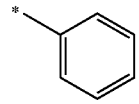
Formula 6-1

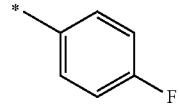
Formula 6-2

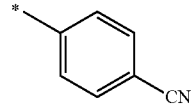
Formula 6-3

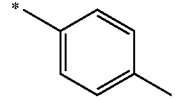
Formula 6-4

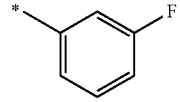
Formula 6-5

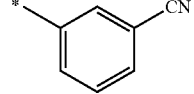
Formula 6-6

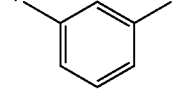
Formula 6-7

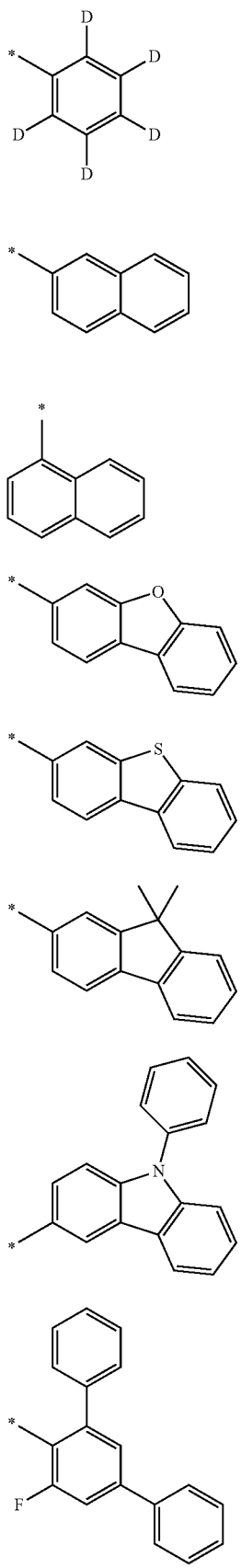
Formula 6-8
Formula 6-9
Formula 6-10
Formula 6-11
Formula 6-12
Formula 6-13
Formula 6-14
Formula 6-15
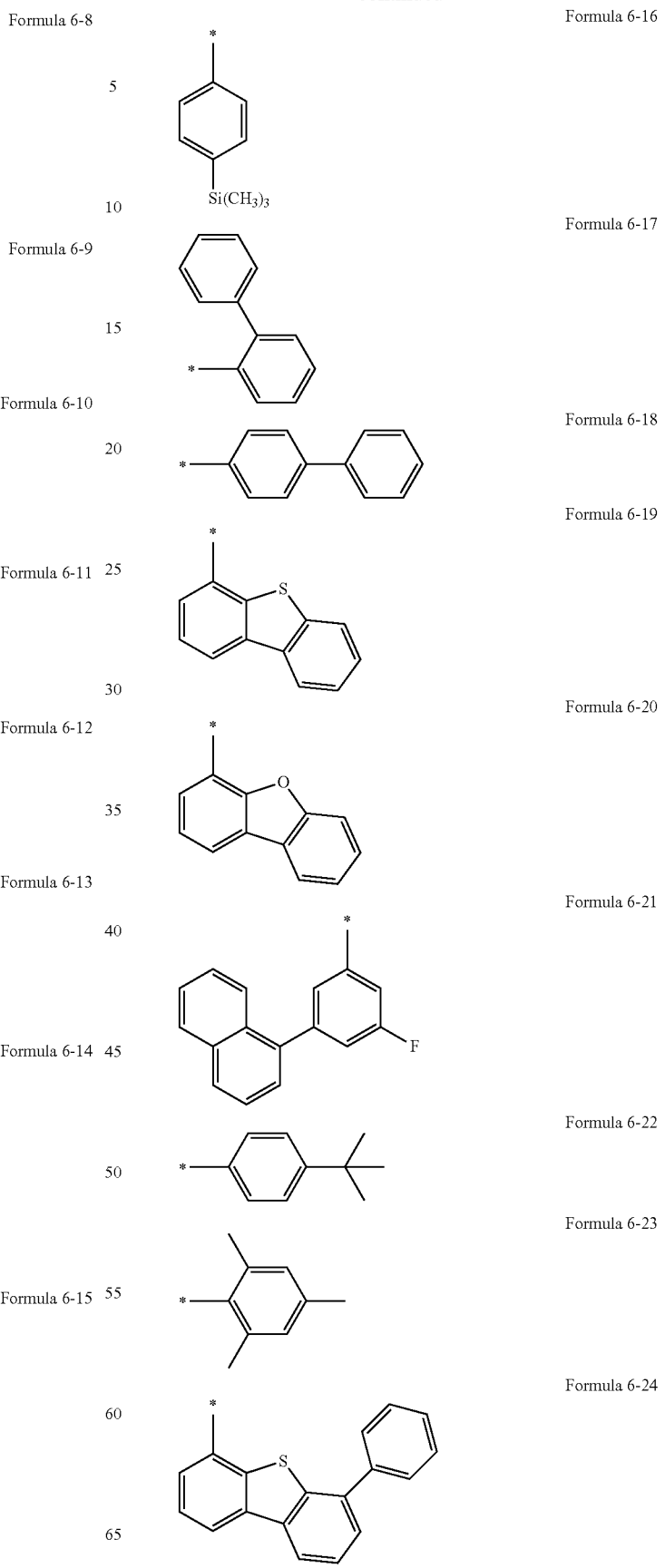
Formula 6-16
Formula 6-17
Formula 6-18
Formula 6-19
Formula 6-20
Formula 6-21
Formula 6-22
Formula 6-23
Formula 6-24

Formula 6-25
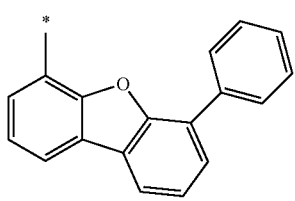
Formula 6-26
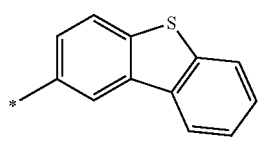
Formula 6-27
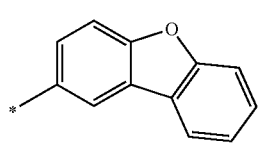
Formula 6-28
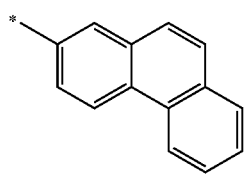
Formula 6-29
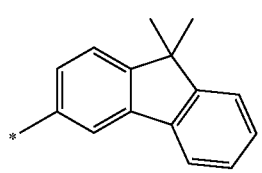
Formula 6-30
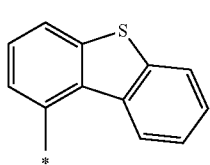
Formula 6-31
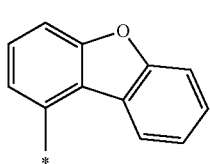
Formula 6-32
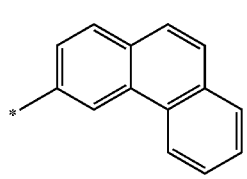
Formula 6-33
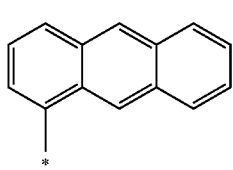
Formula 6-34
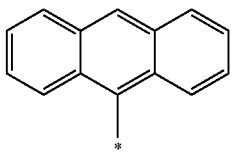
Formula 6-35
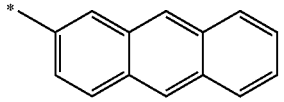
Formula 6-36
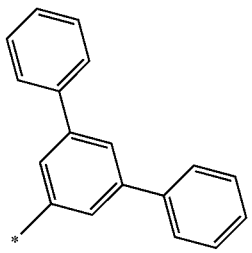
Formula 6-37
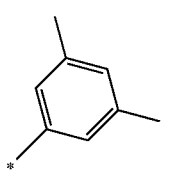
Formula 6-38
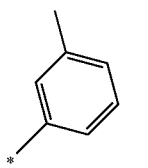
Formula 6-39
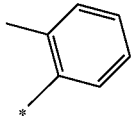
Formula 6-40
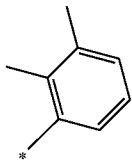
Formula 6-41
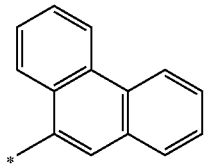
Formula 6-42
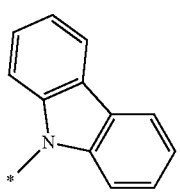

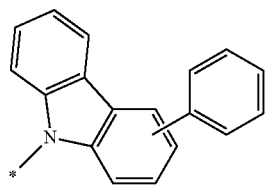
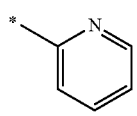
Formula 10-1
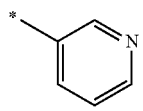
Formula 10-2
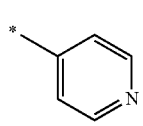
Formula 10-3
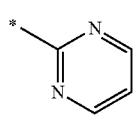
Formula 10-4
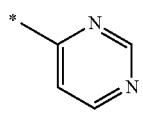
Formula 10-5
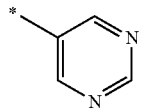
Formula 10-6
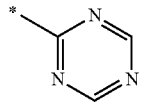
Formula 10-7
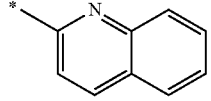
Formula 10-8
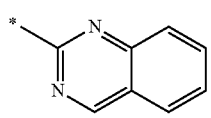
Formula 10-9
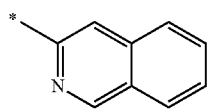
Formula 10-10
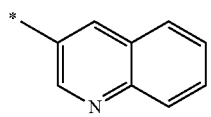
Formula 10-11
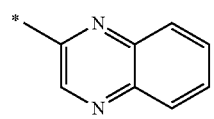
Formula 6-43
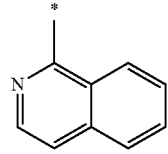
Formula 10-12
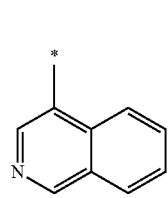
Formula 10-13
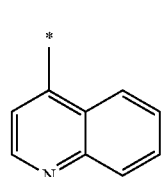
Formula 10-14
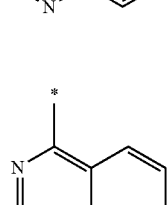
Formula 10-15
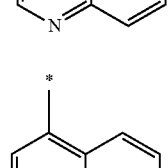
Formula 10-16
Formula 10-17
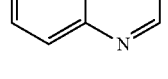
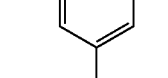
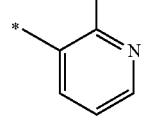
Formula 10-18
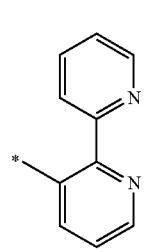
Formula 10-19

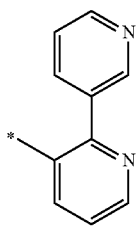
Formula 10-20
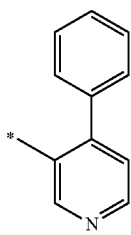
Formula 10-26
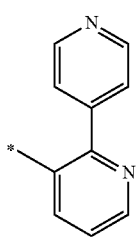
Formula 10-21
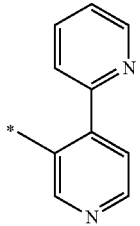
Formula 10-27
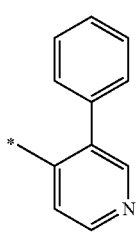
Formula 10-22
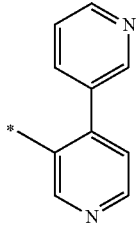
Formula 10-28
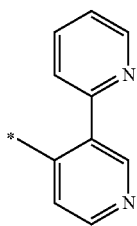
Formula 10-23
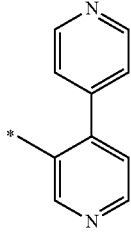
Formula 10-29
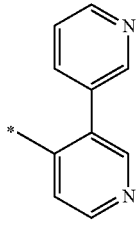
Formula 10-24
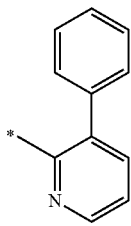
Formula 10-30
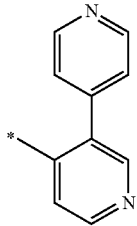
Formula 10-25
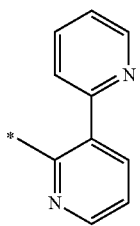
Formula 10-31

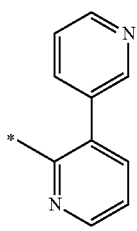
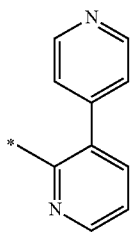
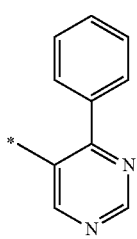
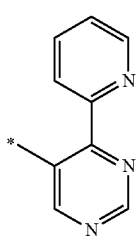
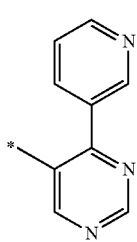
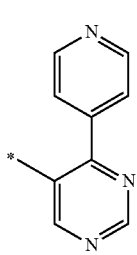
Formula 10-32
Formula 10-33
Formula 10-34
Formula 10-35
Formula 10-36
Formula 10-37
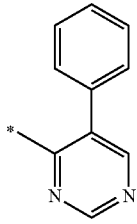
Formula 10-38
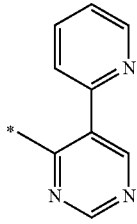
Formula 10-39
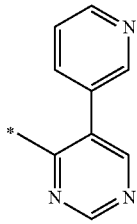
Formula 10-40
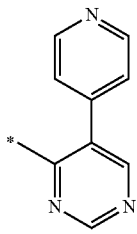
Formula 10-41
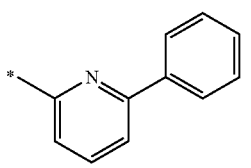
Formula 10-42
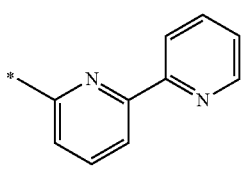
Formula 10-43
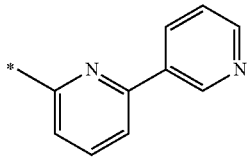
Formula 10-44
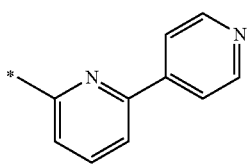
Formula 10-45

Formula 10-46
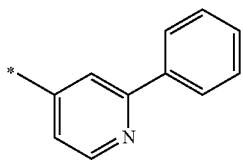
Formula 10-47
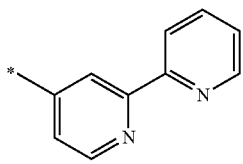
Formula 10-48
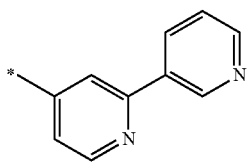
Formula 10-49
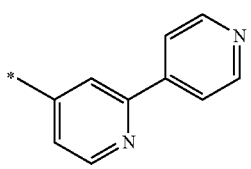
Formula 10-50
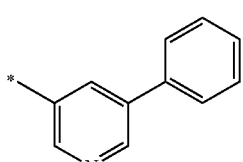
Formula 10-51
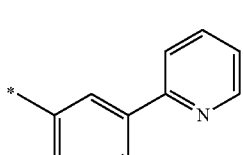
Formula 10-52
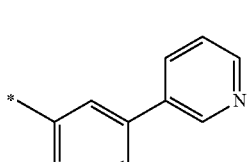
Formula 10-53
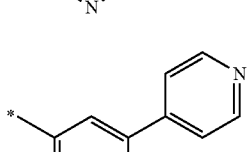
Formula 10-54
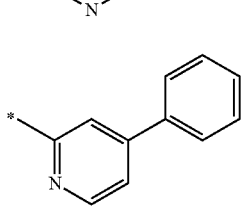
Formula 10-55
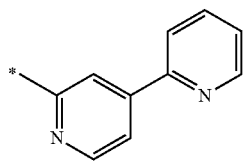
Formula 10-56
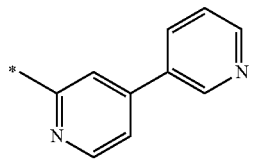
Formula 10-57
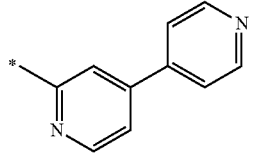
Formula 10-58
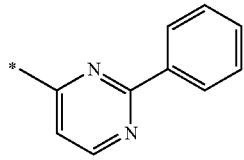
Formula 10-59
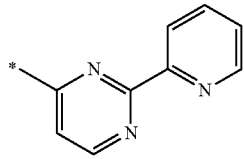
Formula 10-60
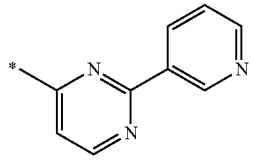
Formula 10-61
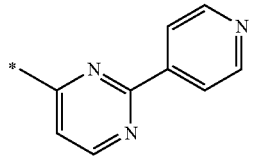
Formula 10-62
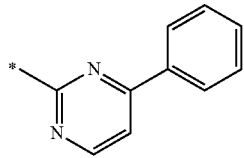
Formula 10-63
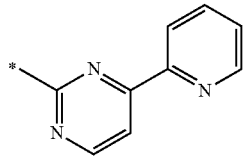

-continued
Formula 10-64
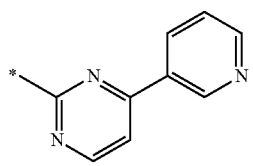
Formula 10-65
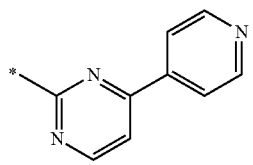
Formula 10-66
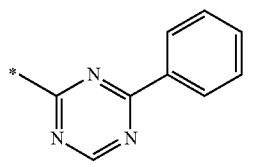
Formula 10-67
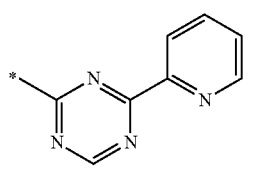
Formula 10-68
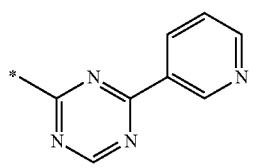
Formula 10-69
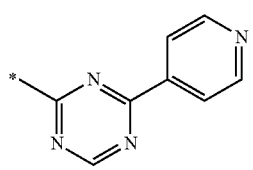
Formula 10-70
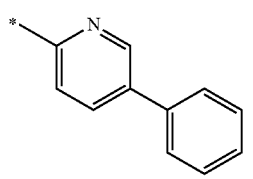
Formula 10-71
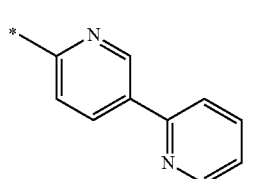
Formula 10-72
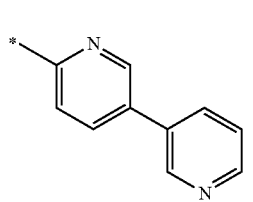
-continued
Formula 10-73
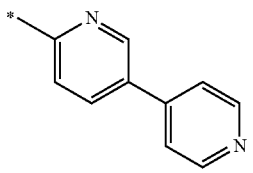
Formula 10-74
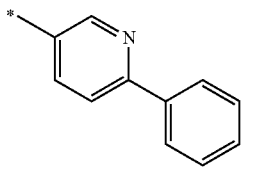
Formula 10-75
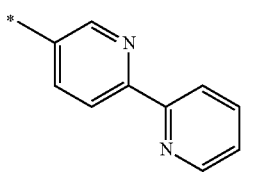
Formula 10-76
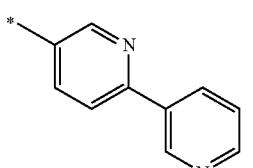
Formula 10-77
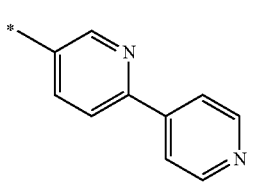
Formula 10-78
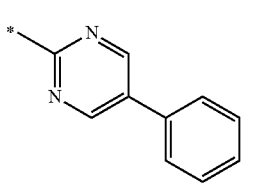
Formula 10-79
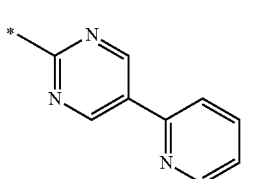
Formula 10-80
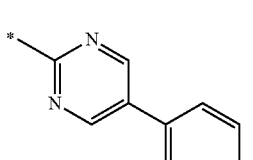
Formula 10-81
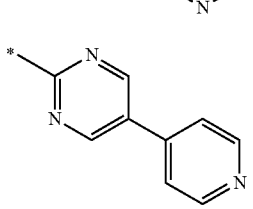

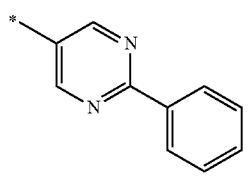
Formula 10-82
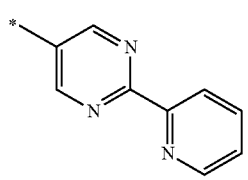
Formula 10-83
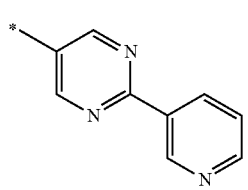
Formula 10-84
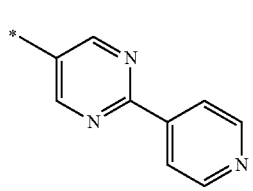
Formula 10-85
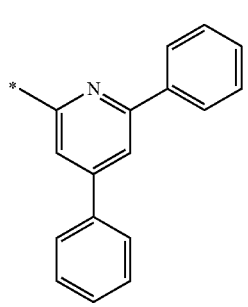
Formula 10-86
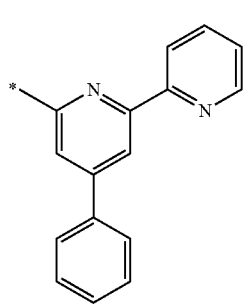
Formula 10-87
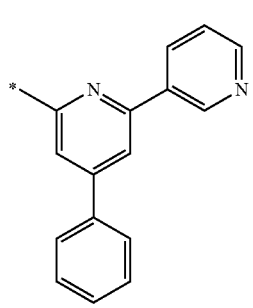
Formula 10-88
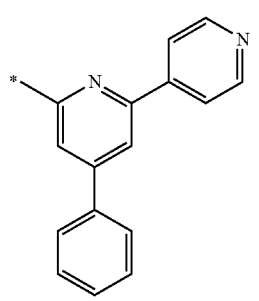
Formula 10-89
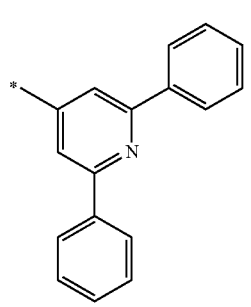
Formula 10-90
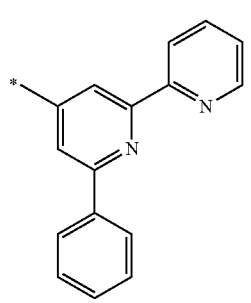
Formula 10-91
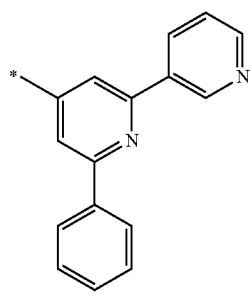
Formula 10-92
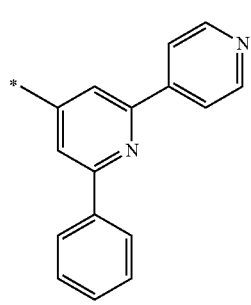
Formula 10-93

Formula 10-94
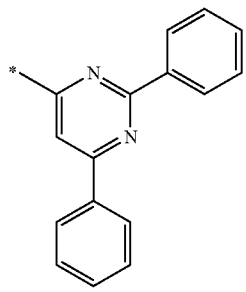
Formula 10-95
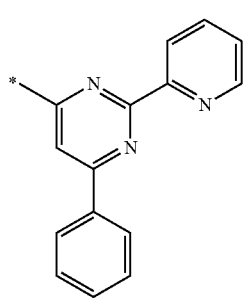
Formula 10-96
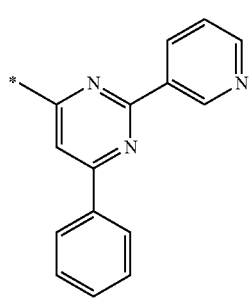
Formula 10-97
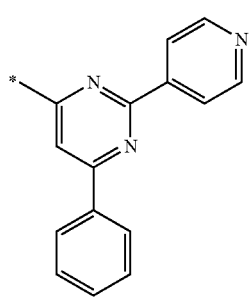
Formula 10-98
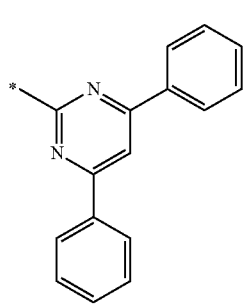
Formula 10-99
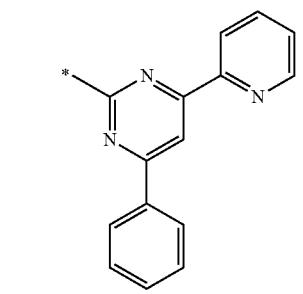
Formula 10-100
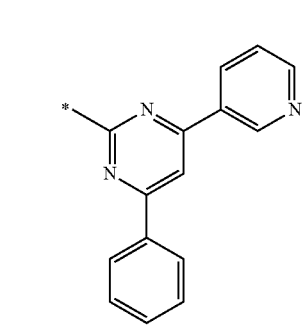
Formula 10-101
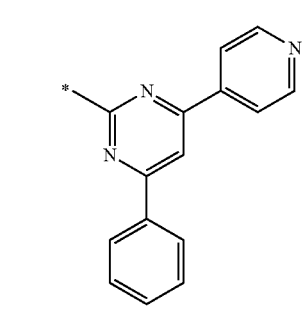
Formula 10-102
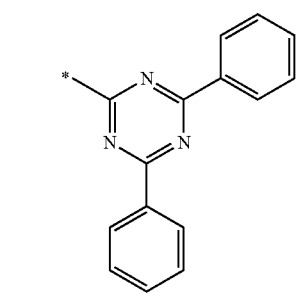
Formula 10-103
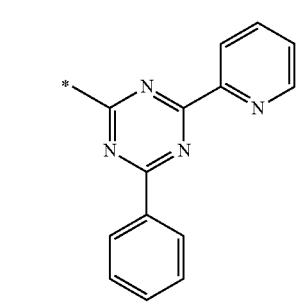

Formula 10-104
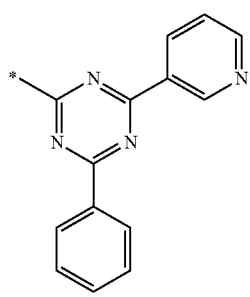
Formula 10-105
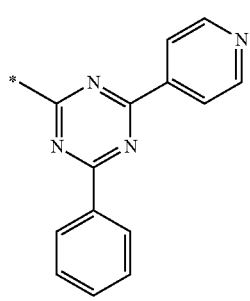
Formula 10-106
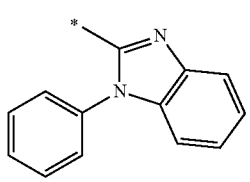
Formula 10-107
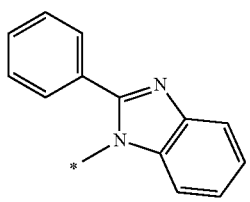
Formula 10-108
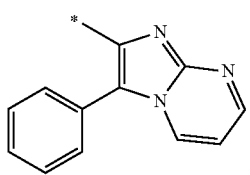
Formula 10-109
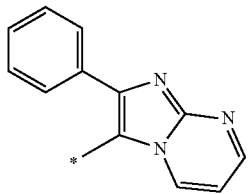
Formula 10-110
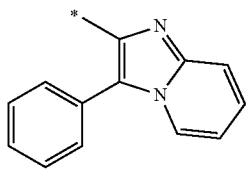
Formula 10-111
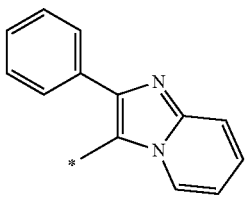
Formula 10-112
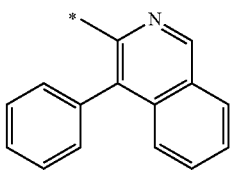
Formula 10-113
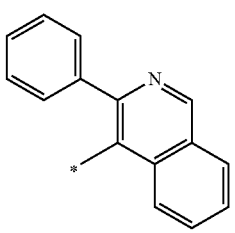
Formula 10-114
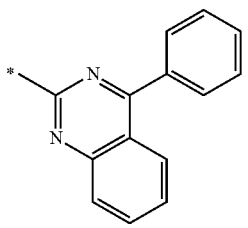
Formula 10-115
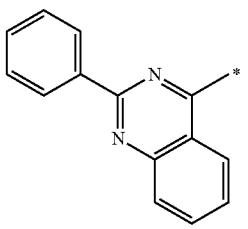
Formula 10-116
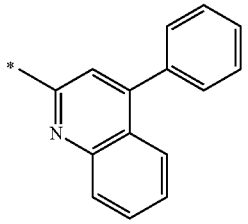
Formula 10-117
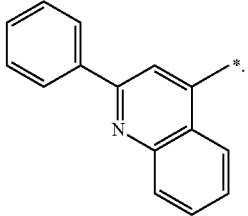
In Formulae 6-1 to 6-43 and 10-1 to 10-117, * indicates a binding site to a neighboring atom, and "D" may refer to deuterium.

In various embodiments, in the Formulae described above,

R$_3$ to R$_6$ and R$_{13}$ may each independently be selected from hydrogen, deuterium, —F, —Cl, —Br, —I, a hydroxyl group, a cyano group, a nitro group, an amidino group, a hydrazino group, a hydrazono group, a C$_1$-C$_{20}$ alkyl group, a C$_1$-C$_{20}$ alkoxy group, a phenyl group, a naphthyl group, and —Si(Q$_1$)(Q$_2$)(Q$_3$), and R$_1$, R$_2$, R$_{11}$, R$_{12}$, R$_{501}$, and R$_{502}$ may each independently be selected from a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, and a substituted or unsubstituted monovalent non-aromatic condensed heteropolycyclic group (e.g., R$_1$, R$_2$, R$_{11}$, R$_{12}$, R$_{501}$, and R$_{502}$ may each independently be selected from groups represented by Formulae 5-1 to 5-75 or groups represented by Formulae 6-1 to 6-43 and 10-1 to 10-117).

In various embodiments, in the Formulae described above,

R$_3$ to R$_6$ and R$_{13}$ may each be hydrogen, and

R$_1$, R$_2$, R$_{11}$, R$_{12}$, R$_{501}$, and R$_{502}$ may each independently be selected from groups represented by Formulae 5-1 to 5-75 (e.g., groups represented by Formulae 6-1 to 6-43 and 10-1 to 10-117), but are not limited thereto.

b1, b2, b5, b6, b11, and b12 in the Formulae described above may each independently be an integer selected from 0 to 4, b3 and b4 may each independently be an integer selected from 0 to 6, and b13 may be 0, 1, or 2.

For example, b1, b2, b11, and b12 in the Formulae described above may each independently be 0, 1, or 2, or may each independently be 1 or 2.

In various embodiments, b1, b2, b11, and b12 in the Formulae described above may be 1, but are not limited thereto.

b3 to b6 and b13 in the Formulae described above may each independently be 0, 1, or 2, or may each independently be 0 or 1, but are not limited thereto.

c1 and c2 in Formula 1 may each independently be an integer selected from 0 to 4, and the sum of c1 and c2 (c1+c2) may be 1 or greater. That is, in Formula 1, at least one selected from the group represented by *-[(L$_1$)$_{a1}$-(R$_1$)$_{b1}$] and the group represented by *-[(L$_2$)$_{a2}$-(R$_2$)$_{b2}$] is present.

In various embodiments, in Formula 1, the sum of c1 and c2 (c1+c2) may be 1 or 2.

In various embodiments, in Formula 1, c1 may be 1 and c2 may be 0, c1 may be 1 and c2 may be 1, or c1 may be 0 and c2 may be 1, but embodiments are not limited thereto.

xd4 in Formula 501 may be an integer selected from 1 to 6. For example, xd4 in Formula 501 may be 2, 3, or 4, but is not limited thereto. In various embodiments, xd4 in Formula 501 may be 2.

In various embodiments, the first compound may be represented by one selected from Formulae 1A to 1E:

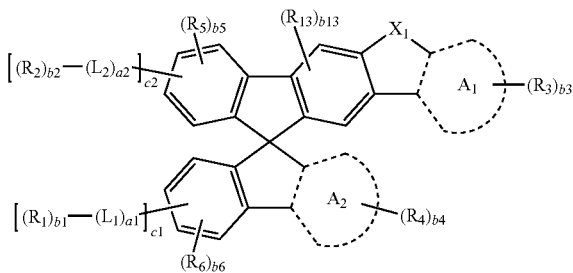

Formula 1A

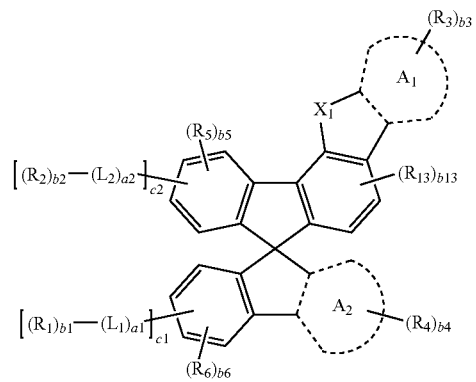

Formula 1B

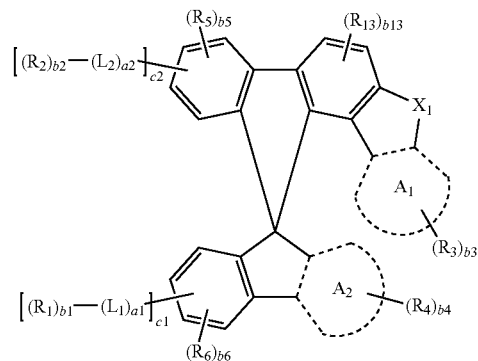

Formula 1C

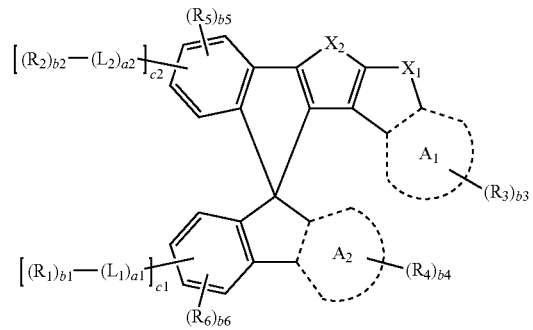

Formula 1D

-continued

Formula 1E

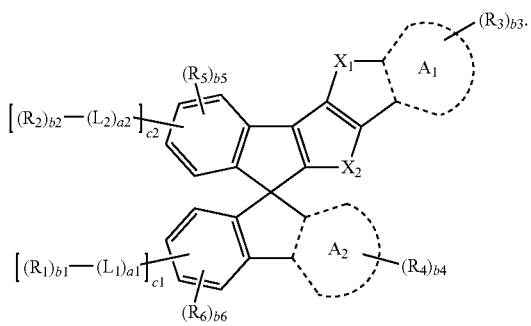

In Formulae 1A to 1E, ring $A_1$, ring $A_2$, $X_1$, $X_2$, $L_1$, $L_2$, a1, a2, $R_1$ to $R_6$, $R_{13}$, b1 to b6, b13, c1, and c2 are the same as described above.

For example, in Formulae 1A to 1E,
ring $A_1$ may be a benzene ring or a pyridine ring, and ring $A_2$ may be selected from a benzene ring, a naphthalene ring, a pyridine ring, a quinoline ring, and an isoquinoline ring; or ring $A_1$ may be selected from a naphthalene ring, a quinoline ring, and an isoquinoline ring, and ring $A_2$ may be a benzene ring or a pyridine ring, $X_1$ and $X_2$ may each independently be O or S, $L_1$ and $L_2$ may each independently be selected from groups represented by Formulae 3-8, 3-9, 3-25, and 3-35 to 3-41 (e.g., groups represented by Formulae 4-11, 4-13, 4-27, and 4-29 to 4-35), a1 and a2 may each independently be 1 or 2, $R_1$ and $R_2$ may each independently be selected from groups represented by Formulae 5-1 to 5-75 (e.g., groups represented by Formulae 6-1 to 6-43 and 10-1 to 10-117), b1 and b2 may each independently be 1 or 2, $R_3$ to $R_6$ and $R_{13}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a naphthyl group, and —Si($Q_1$)($Q_2$)($Q_3$), wherein $Q_1$ to $Q_3$ may each independently be selected from a $C_1$-$C_{10}$ alkyl group, a $C_1$-$C_{10}$ alkoxy group, a phenyl group, and a naphthyl group, b3 to b6 and b13 may each independently be 0, 1, or 2, and c1 may be 1 and c2 may be 0; c1 may be 1 and c2 may be 1; or c1 may be 0 and c2 may be 1, but embodiments are not limited thereto.

In various embodiments, the first compound may be represented by one selected from Formulae 1-1 to 1-7:

Formula 1-1

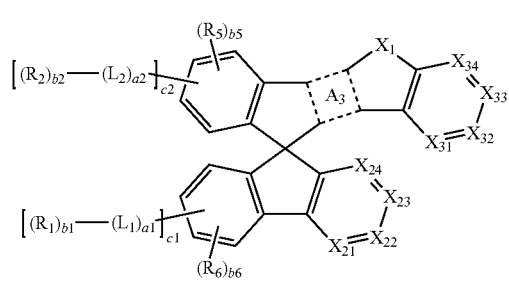

Formula 1-2

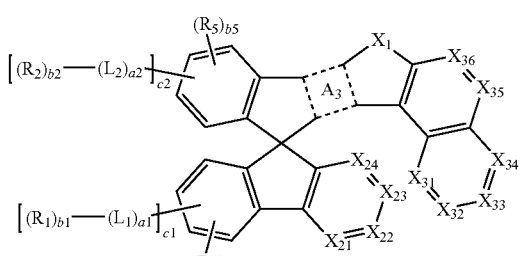

Formula 1-3

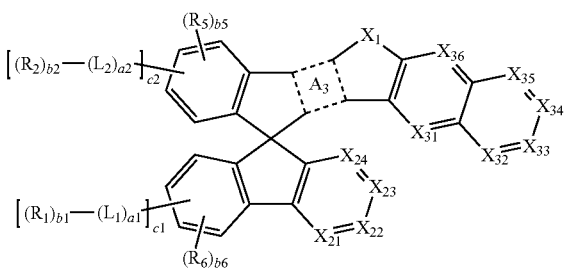

Formula 1-4

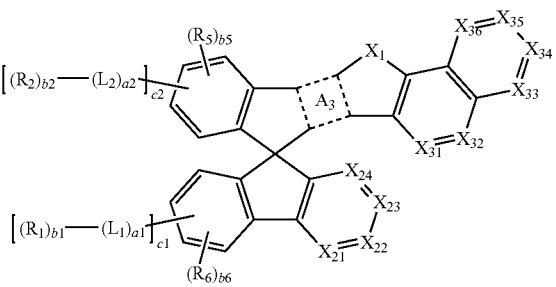

Formula 1-5

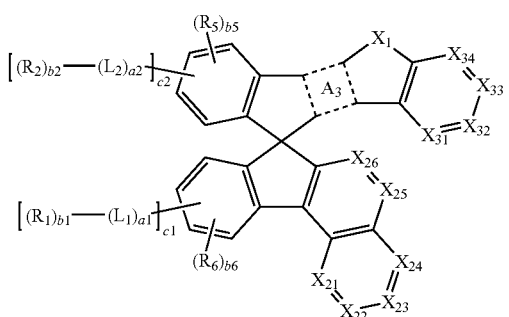

Formula 1-6

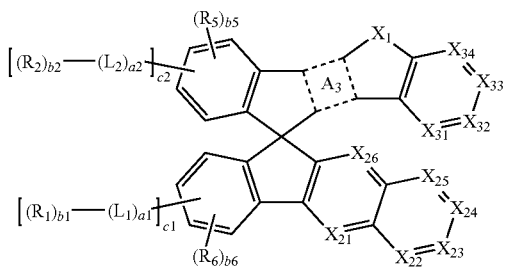

-continued

Formula 1-7

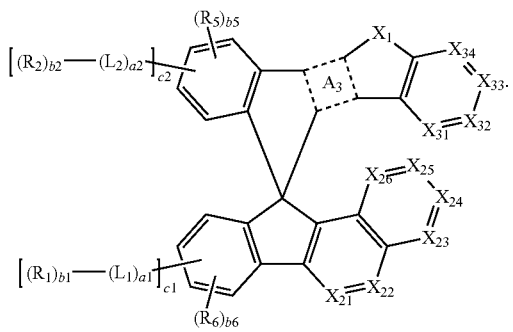

In Formulae 1-1 to 1-7,
ring $A_3$, $X_1$, $L_1$, $L_2$, a1, a2, $R_1$, $R_2$, $R_5$, $R_6$, b1, b2, b5, b6, c1, and c2 are the same as described above,
$X_{21}$ may be N or $C(R_{21})$; $X_{22}$ may be N or $C(R_{22})$; $X_{23}$ may be N or $C(R_{23})$, $X_{24}$ may be N or $C(R_{24})$; $X_{25}$ may be N or $C(R_{25})$; $X_{26}$ may be N or $C(R_{26})$; $X_{31}$ may be N or $C(R_{31})$; $X_{32}$ may be N or $C(R_{32})$; $X_{33}$ may be N or $C(R_{33})$; $X_{34}$ may be N or $C(R_{34})$; $X_{35}$ may be N or $C(R_{35})$; and $X_{36}$ may be N or $C(R_{36})$,
descriptions of $R_{21}$ to $R_{26}$ may each independently be the same as the description provided above in connection with $R_3$, and
descriptions of $R_{31}$ to $R_{36}$ may each independently be the same as the description provided above in connection with $R_4$.
In various embodiments,
none, one, or two selected from $X_{21}$ to $X_{24}$ and $X_{31}$ to $X_{34}$ in Formula 1-1 may be N,
none, one, or two selected from $X_{21}$ to $X_{24}$ and $X_{31}$ to $X_{36}$ in Formulae 1-2 to 1-4 may be N, and
none, one, or two selected from $X_{21}$ to $X_{26}$ and $X_{31}$ to $X_{36}$ in Formulae 1-5 to 1-7 may be N.
In various embodiments,
none or one selected from $X_{21}$ to $X_{24}$ in Formulae 1-1 to 1-4 may be N,
none or one selected from $X_{31}$ to $X_{34}$ in Formulae 1-1 and 1-5 to 1-7 may be N,
none or one selected $X_{21}$ to $X_{26}$ in Formulae 1-5 to 1-7 may be N, and
none or one selected from $X_{31}$ to $X_{36}$ in Formulae 1-2 to 1-4 may be N.
For example, ring $A_3$ in Formulae 1-1 to 1-7 may be a group represented by Formula 2A.
In various embodiments, in Formulae 1-1 to 1-7,
$X_1$ and $X_2$ may each independently be O or S,
$L_1$ and $L_2$ may each independently be selected from groups represented by Formulae 3-8, 3-9, 3-25, and 3-35 to 3-41 (e.g., groups represented by Formulae 4-11, 4-13, 4-27, and 4-29 to 4-35),
a1 and a2 may each independently be 1 or 2,
$R_1$ and $R_2$ may each independently be selected from groups represented by Formulae 5-1 to 5-75 (e.g., groups represented by Formulae 6-1 to 6-43 and 10-1 to 10-117),
b1 and b2 may each independently be 1 or 2,
$R_{21}$ to $R_{26}$, $R_{31}$ to $R_{36}$, $R_5$, and $R_6$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a naphthyl group, and —Si($Q_1$)($Q_2$)($Q_3$),
wherein $Q_1$ to $Q_3$ may each independently be selected from a $C_1$-$C_{10}$ alkyl group, a $C_1$-$C_{10}$ alkoxy group, a phenyl group, and a naphthyl group,
b5 and b6 may each independently be 0, 1, or 2, and
c1 may be 1 and c2 may be 0; c1 may be 1 and c2 may be 1; or c1 may be 0 and c2 may be 1, but embodiments of the present disclosure are not limited thereto.

In various embodiments, the first compound may be represented by one selected from Formulae 1(1) to 1(24), but is not limited thereto:

Formula 1(5)
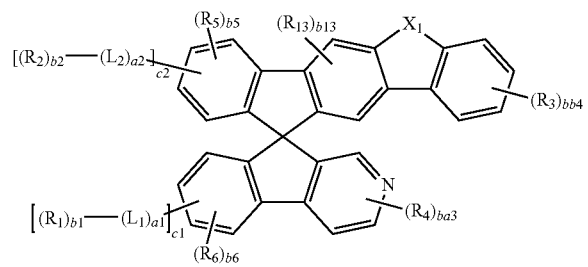
Formula 1(6)
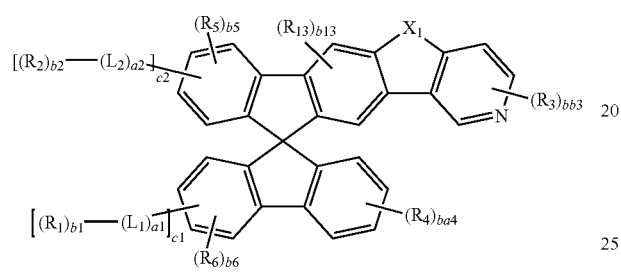
Formula 1(7)
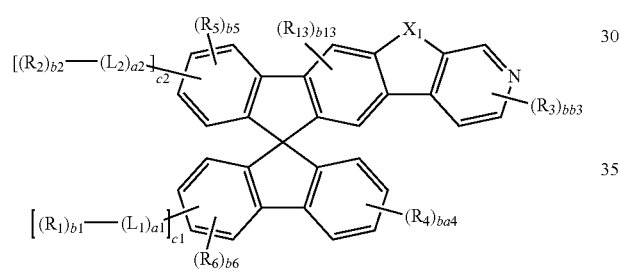
Formula 1(8)
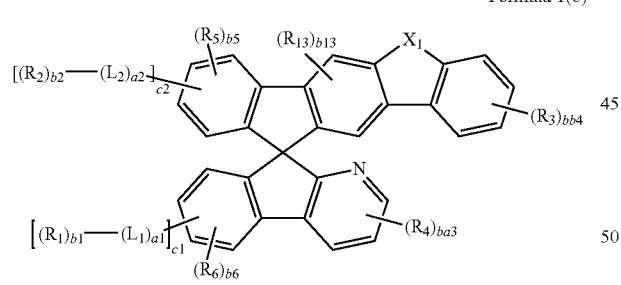
Formula 1(9)
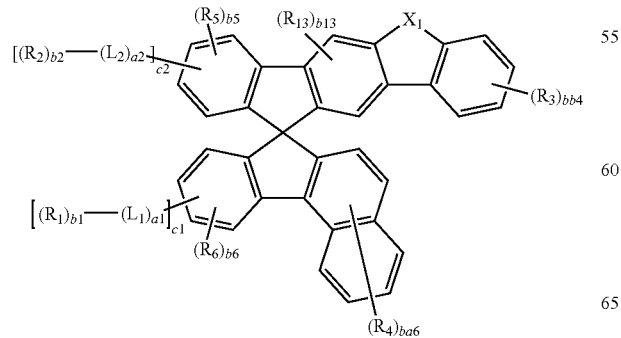
Formula 1(10)
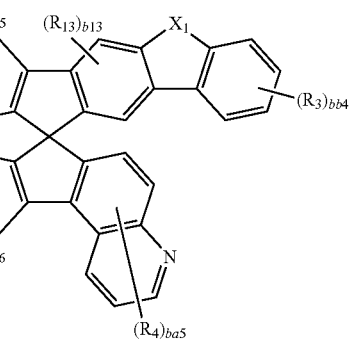
Formula 1(11)
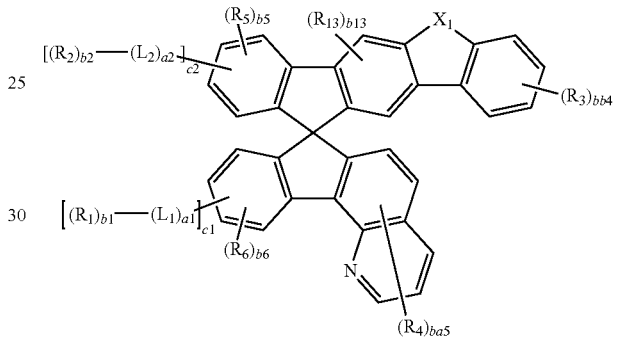
Formula 1(12)
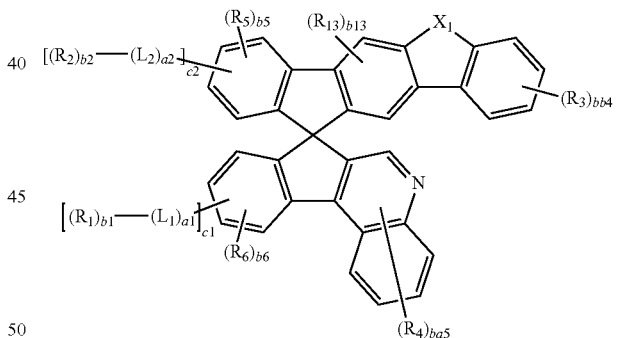
Formula 1(13)
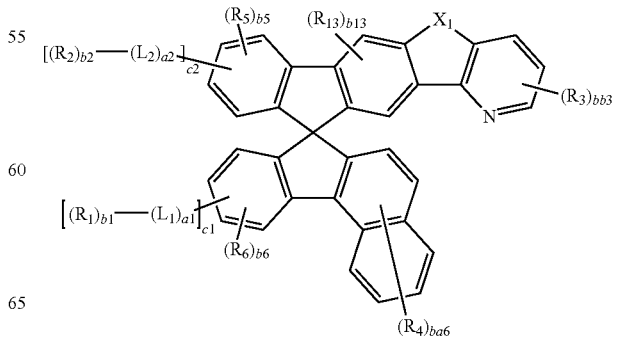

-continued
Formula 1(14)
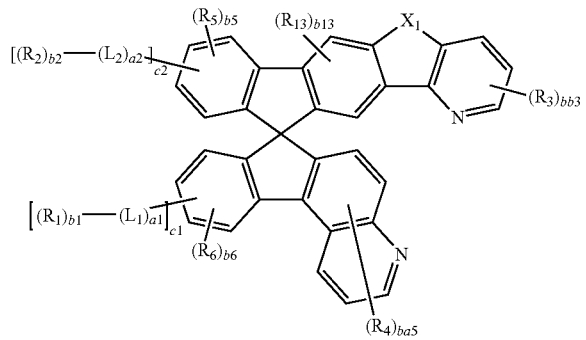
Formula 1(15)
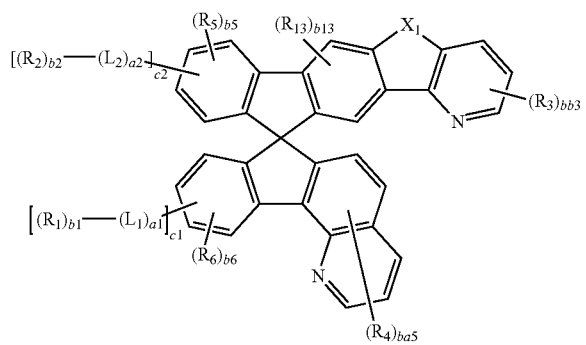
Formula 1(16)
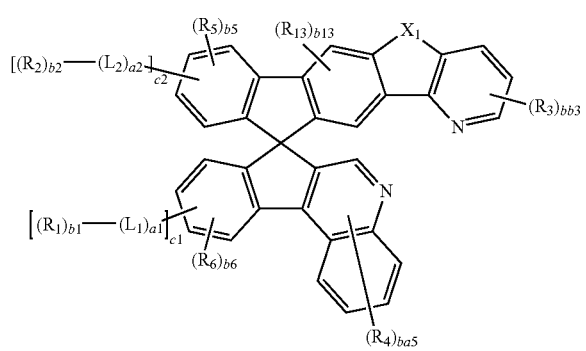
Formula 1(17)
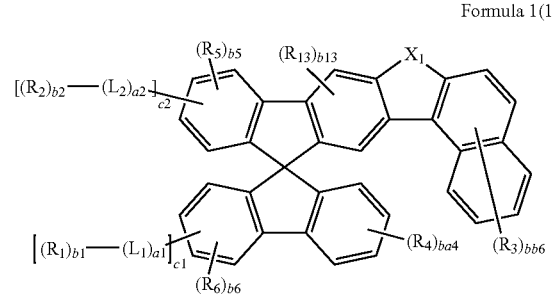
-continued
Formula 1(18)
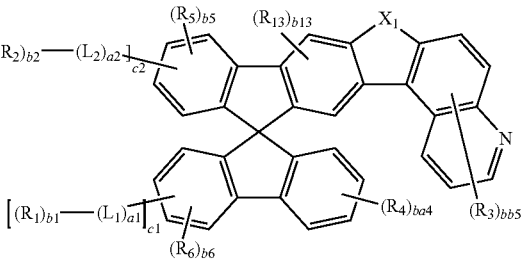
Formula 1(19)
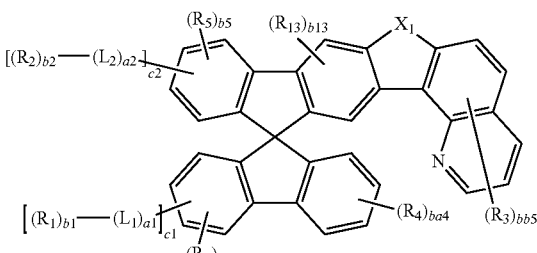
Formula 1(20)
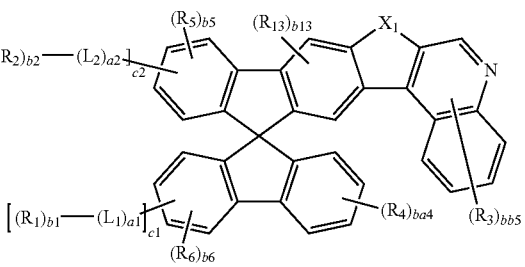
Formula 1(21)
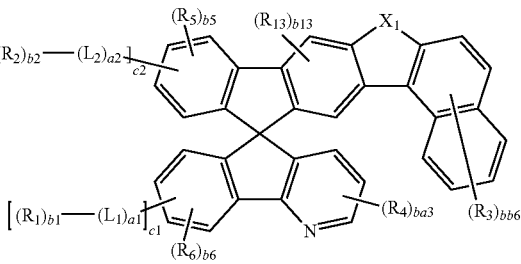
Formula 1(22)
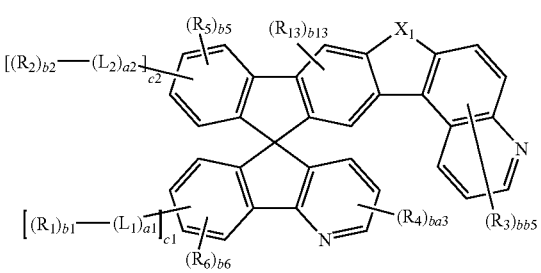

-continued

Formula 1(23)

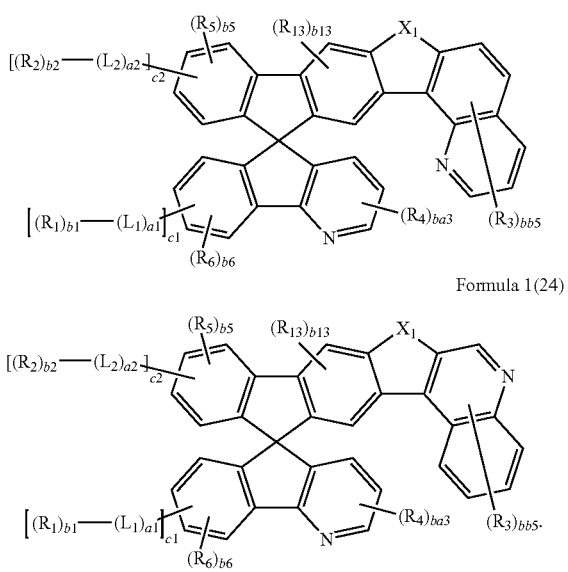

Formula 1(24)

In Formulae 1(1) to 1(24),
$X_1$, $L_1$, $L_2$, a1, a2, $R_1$ to $R_6$, $R_{13}$, b1 to b6, b13, c1, and c2 are the same as described above,
ba3 and bb3 may each independently be an integer selected from 0 to 3,
ba4 and bb4 may each independently be an integer selected from 0 to 4,
ba5 and bb5 may each independently be an integer selected from 0 to 5, and
ba6 and bb6 may each independently be an integer selected from 0 to 6.

In various embodiments, in Formulae 1(1) to 1(24),
$X_1$ and $X_2$ may each independently be O or S,
$L_1$ and $L_2$ may each independently be selected from groups represented by Formulae 3-8, 3-9, 3-25, and 3-35 to 3-41 (e.g., groups represented by Formulae 4-11, 4-13, 4-27, and 4-29 to 4-35),
a1 and a2 may each independently be 1 or 2,
$R_1$ and $R_2$ may be each independently be selected from groups represented by Formulae 5-1 to 5-75 (e.g., groups represented by Formulae 6-1 to 6-43 and 10-1 to 10-117),
b1 and b2 may each independently be 1 or 2,
$R_3$ to $R_6$ and $R_{13}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a naphthyl group, and —Si($Q_1$)($Q_2$)($Q_3$),
wherein $Q_1$ to $Q_3$ may each independently be selected from a $C_1$-$C_{10}$ alkyl group, a $C_1$-$C_{10}$ alkoxy group, a phenyl group, and a naphthyl group,
ba3, bb3, ba4, bb4, ba5, bb5, ba6, bb6, b5, and b6 may each independently be 0, 1, or 2, and
c1 may be 1 and c2 may be 0; c1 may be 1 and c2 may be 1; or c1 may be 0 and c2 may be 1, but embodiments are not limited thereto.

In various embodiments, the first compound may be represented by one selected from Formulae 1A-1 to 1A-3, but is not limited thereto:

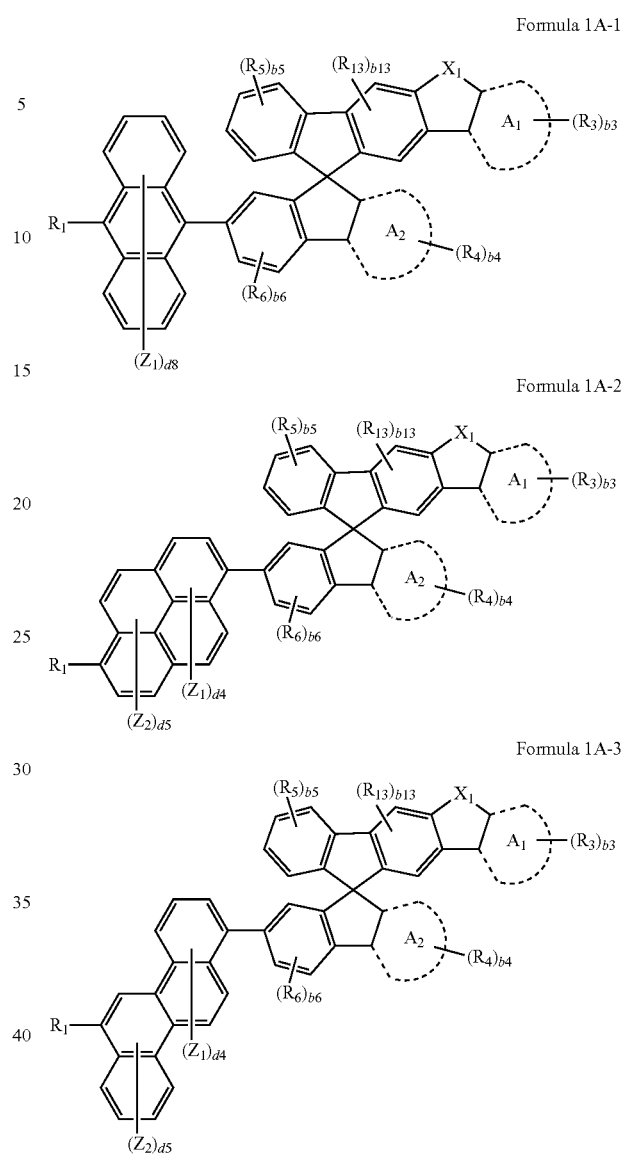

In Formulae 1A-1 to 1A-3, ring $A_1$, ring $A_2$, $X_1$, $L_{11}$, $L_{12}$, a11, a12, $R_1$, $R_3$ to $R_6$, $R_{11}$ to $R_{13}$, b3 to b6, b11 to b13, c1, and c2 are the same as described above.

For example, ring $A_1$ and ring $A_2$ in Formulae 1A-1 to 1A-3 may each independently be selected from a benzene ring, a naphthalene ring, a pyridine ring, a quinoline ring, and an isoquinoline ring,
$X_1$ may be O or S,
$R_1$ may be selected from groups represented by Formulae 5-1 to 5-75 (e.g., groups represented by Formulae 6-1 to 6-43 and 10-1 to 10-117),
$R_3$ to $R_6$, $R_{13}$, $Z_1$, and $Z_2$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, and a naphthyl group, and
b3 to b6, b13, d4, and d5 may each independently be 0, 1, or 2, but are not limited thereto.

In various embodiments, the second compound may be represented by one selected from Formulae 501-1 to 501-4:

Formula 501-1

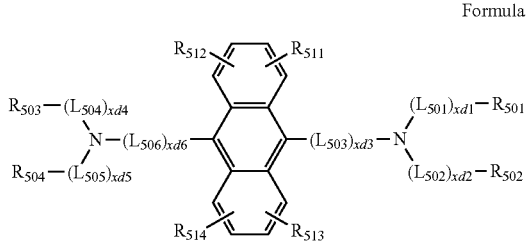

Formula 501-2

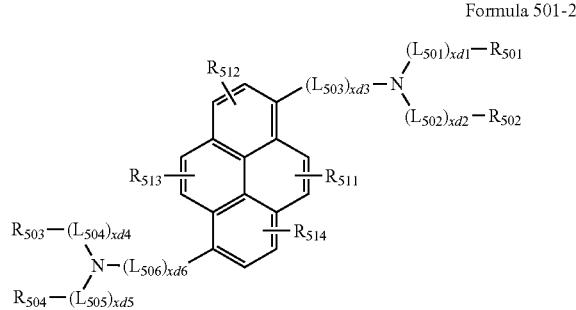

Formula 501-3

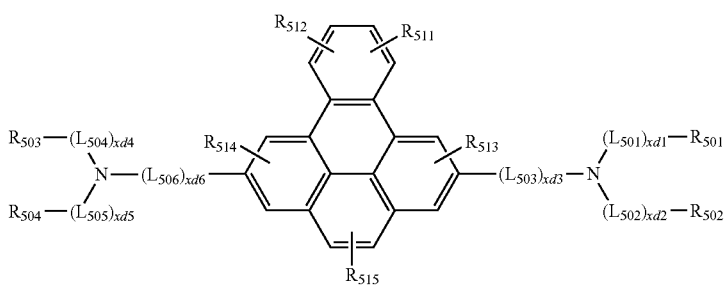

Formula 501-4

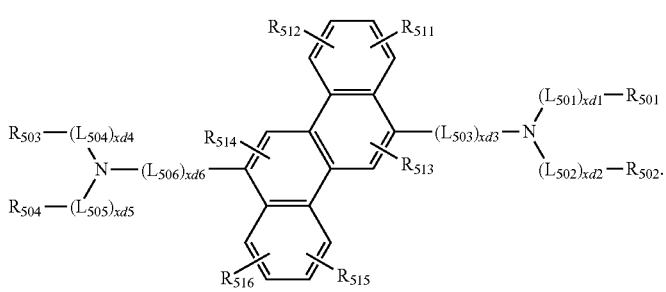

In Formulae 501-1 to 501-4, $L_{501}$ to $L_{503}$, xd1 to xd3, $R_{501}$, and $R_{502}$ are the same as described above, descriptions of $L_{504}$ to $L_{506}$ may each independently be the same as the description provided above in connection with $L_{501}$, descriptions of xd4 and xd5 may each independently be the same as the description provided above in connection with xd1, description of xd6 may be the same as the description provided above in connection with xd3, and descriptions of $R_{511}$ to $R_{516}$ may each independently be the same as the description provided above in connection with $R_3$.

For example, in Formulae 501-1 and 501-4, $L_{501}$ to $L_{506}$ may each independently be selected from groups represented by Formulae 3-1 to 3-41 (e.g., groups represented by Formulae 4-1 to 4-35), xd1 to xd6 may each independently be 0 or 1, $R_{501}$ and $R_{502}$ may each independently be selected from groups represented by Formulae 5-1 to 5-75 (e.g., groups represented by Formulae 6-1 to 6-43 and groups represented by Formulae 10-1 to 10-117), and $R_{511}$ to $R_{516}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{10}$ alkyl group, a $C_1$-$C_{10}$ alkoxy group, a phenyl group, a naphthyl group, and —Si($Q_1$)($Q_2$)($Q_3$), wherein $Q_1$ to $Q_3$ may each independently be selected from a $C_1$-$C_{10}$ alkyl group, a $C_1$-$C_{10}$ alkoxy group, a phenyl group, and a naphthyl group.

For example, the first compound may include at least one selected from Compounds 1 to 60, and the second compound may include at least one selected from Compounds 101 to 112, but the first compound and the second compound are not limited thereto:

1

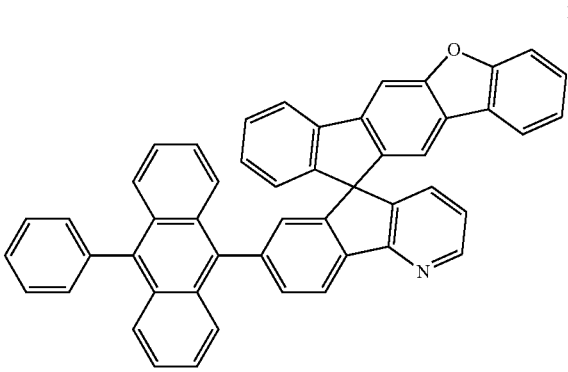

2
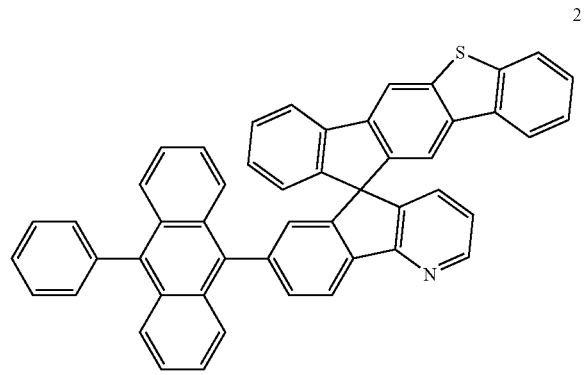
3
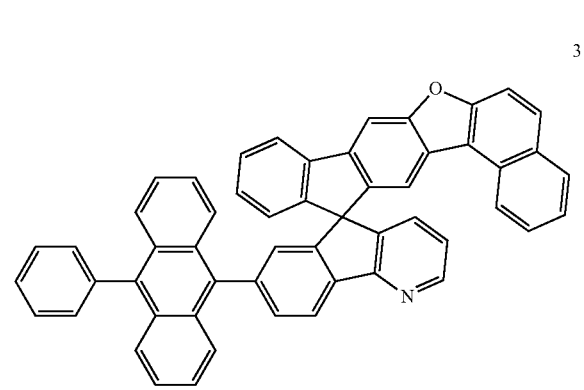
4
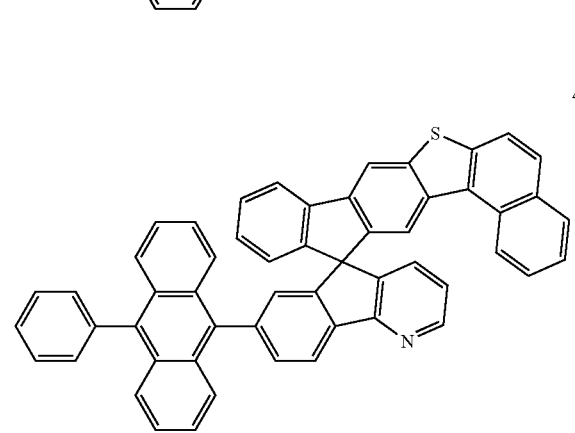
5
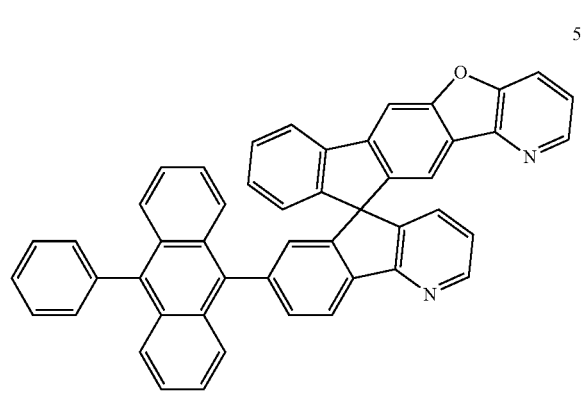
6
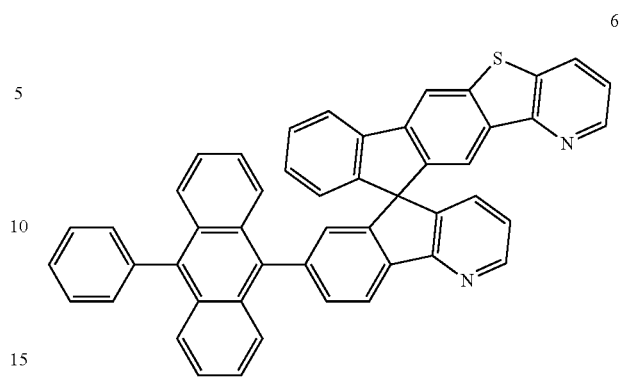
7
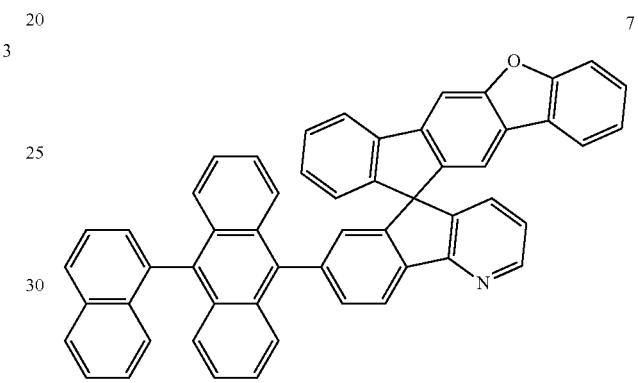
8
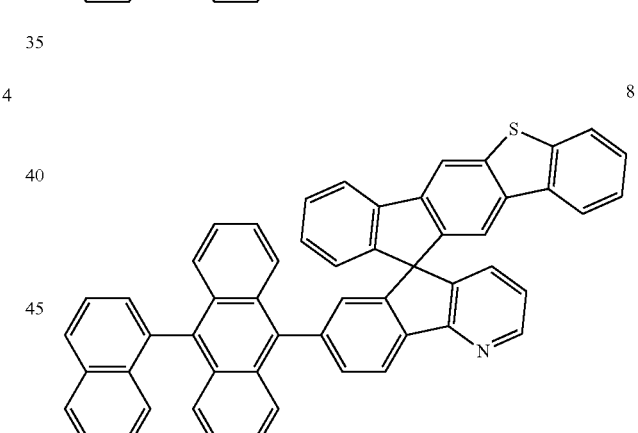
9
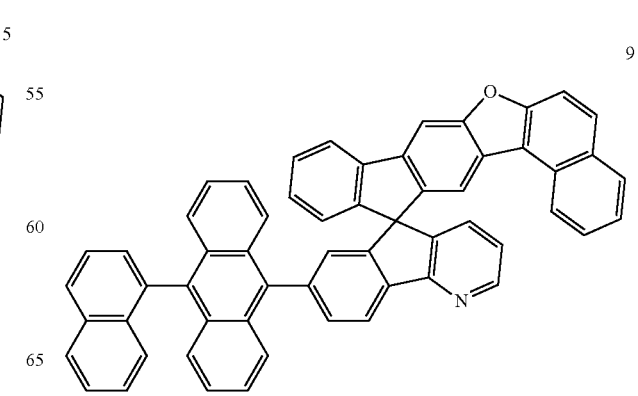

-continued
10
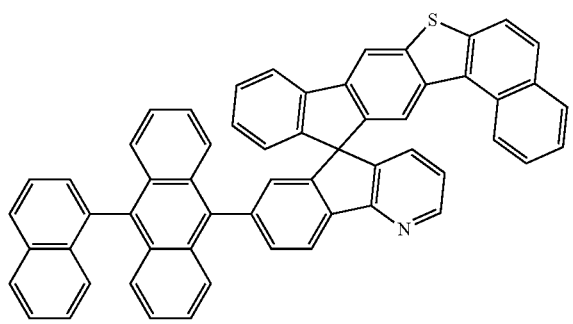
11
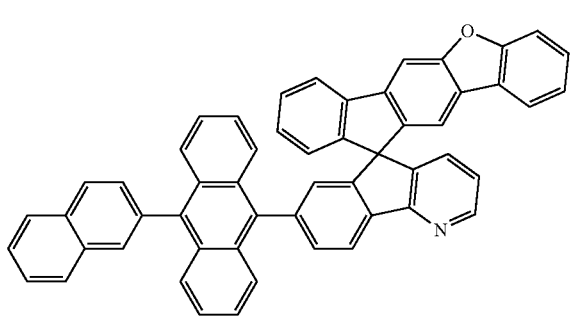
12
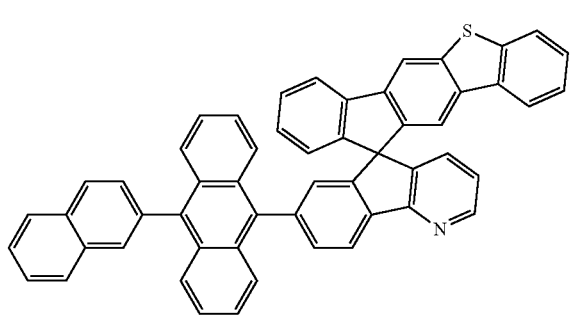
13
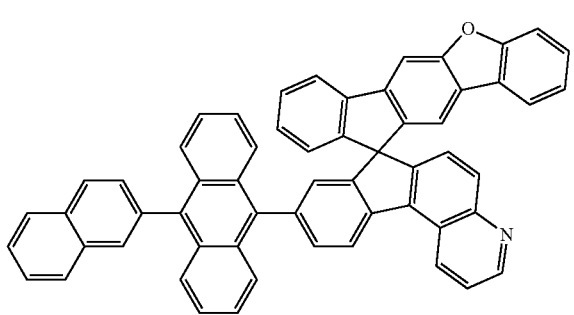
14
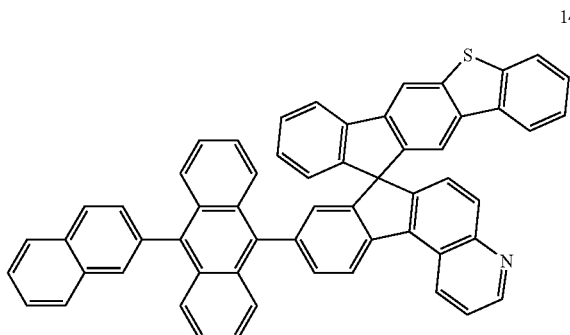
-continued
15
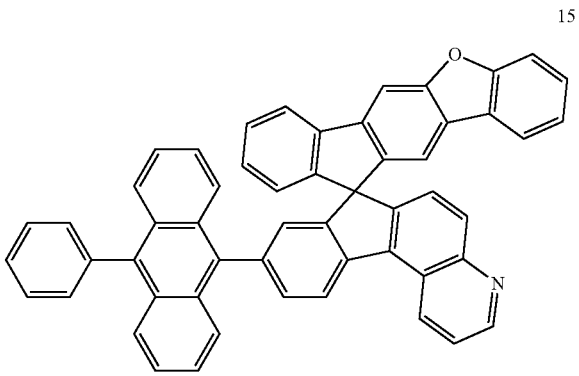
16
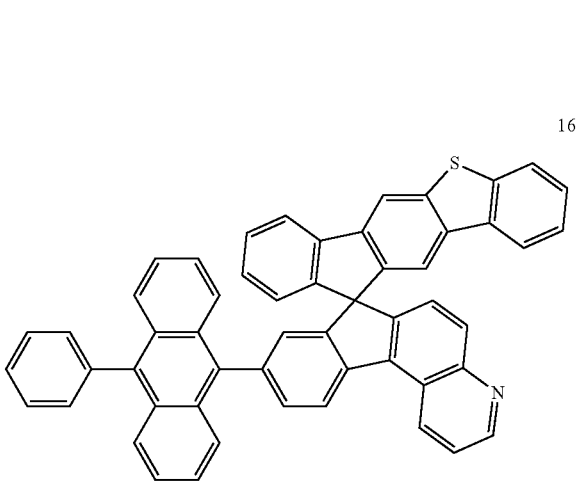
17
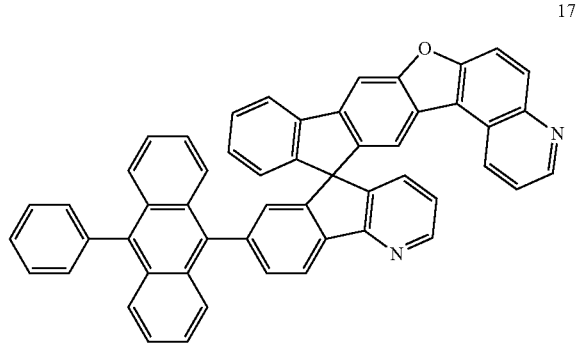
18
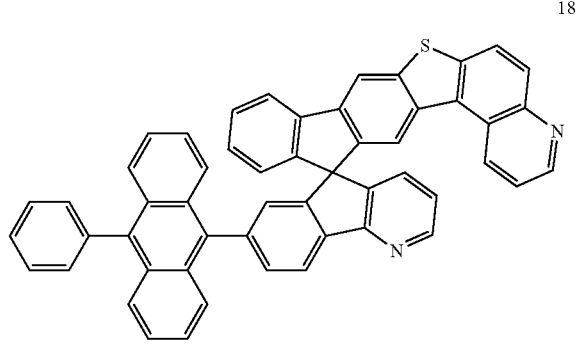

19
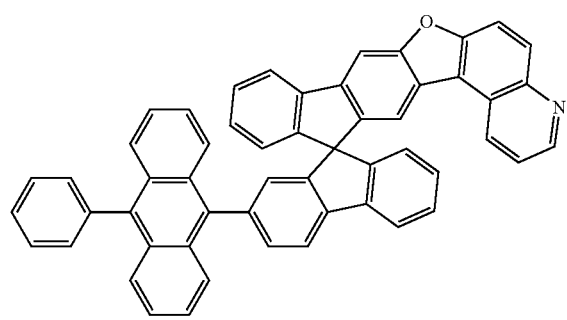
20
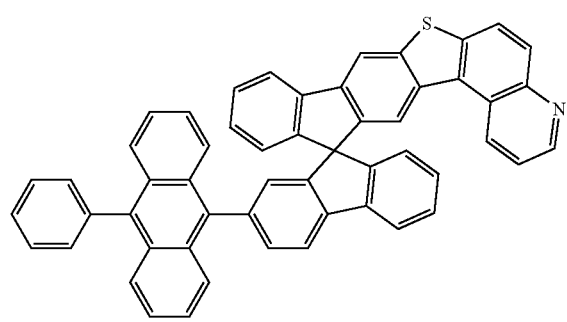
21
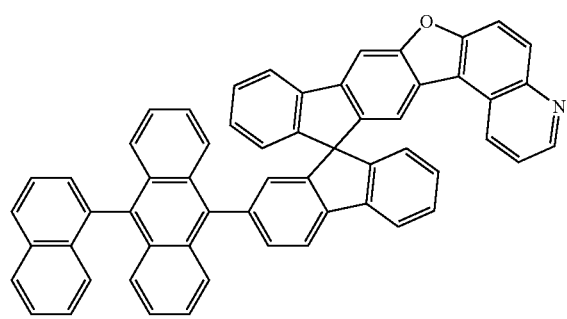
22
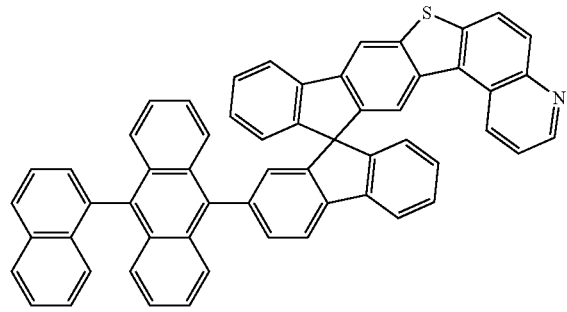
23
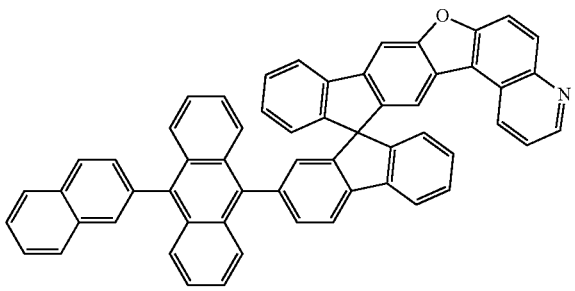
24
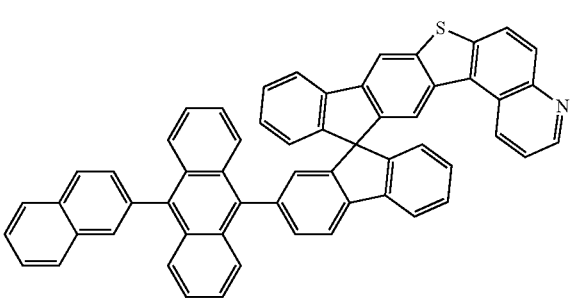
25
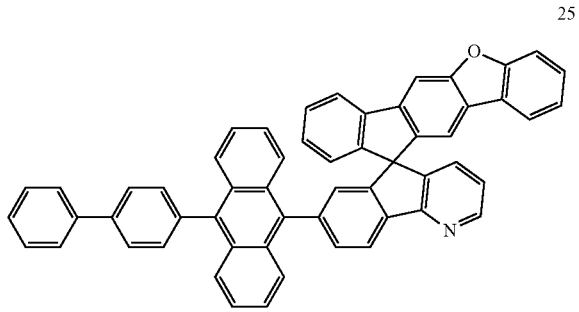
26
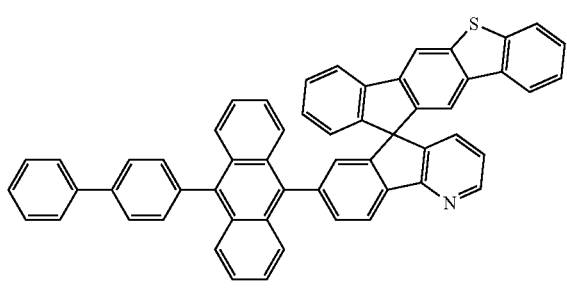
27
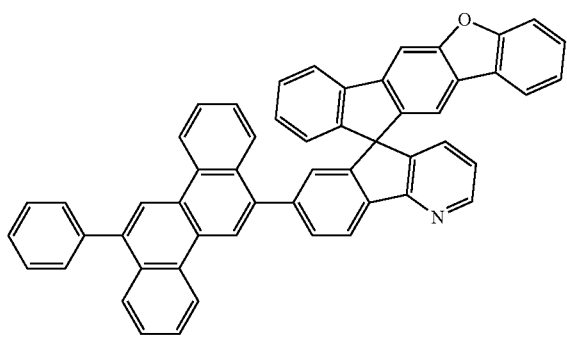
28
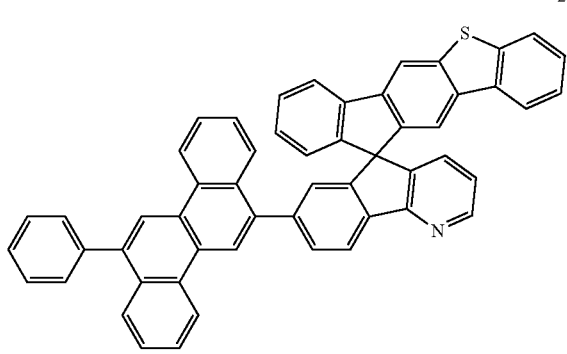

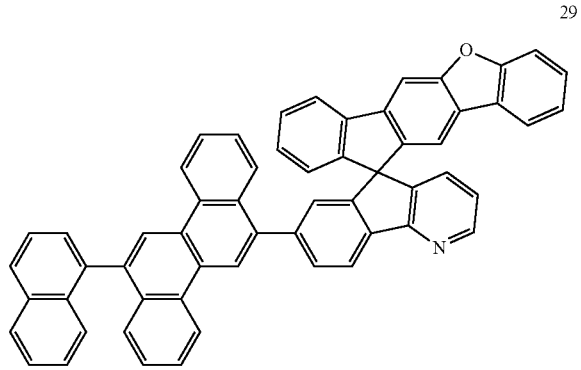
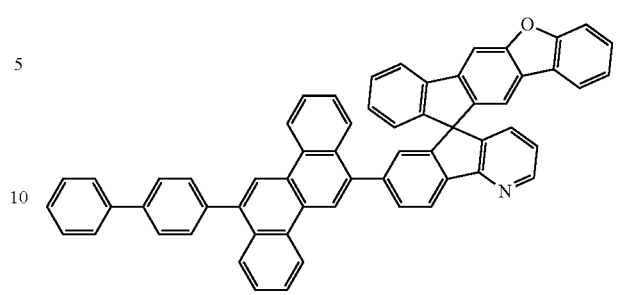
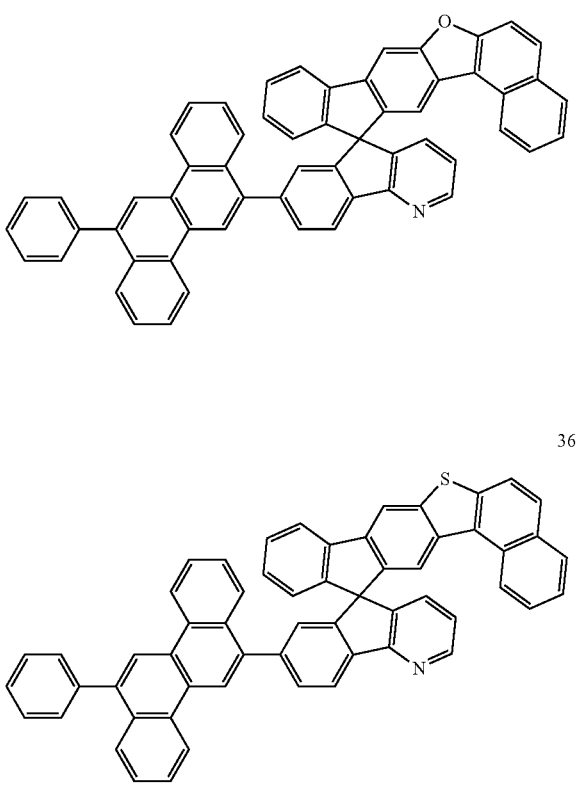

37
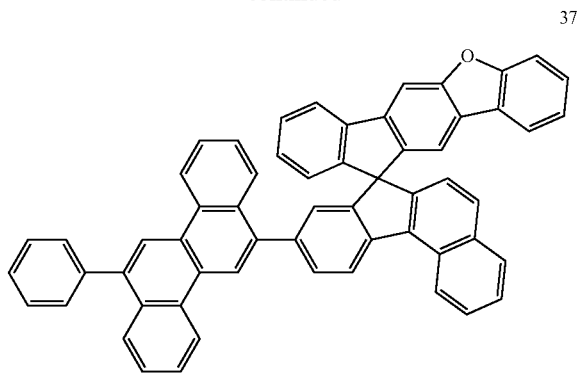
38
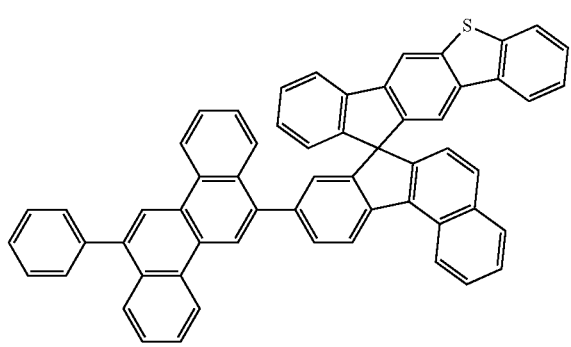
39
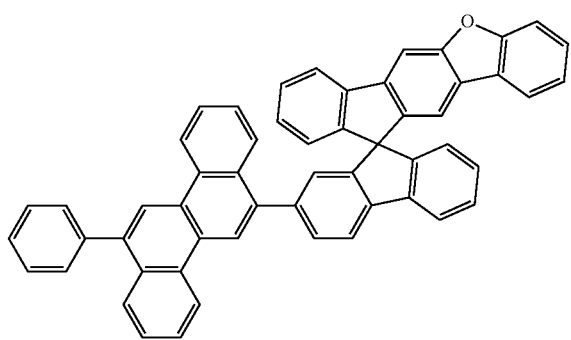
40
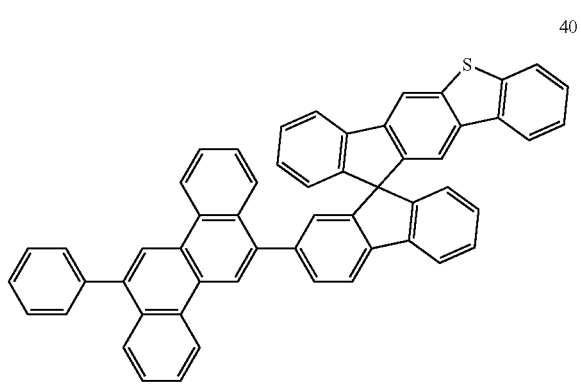
41
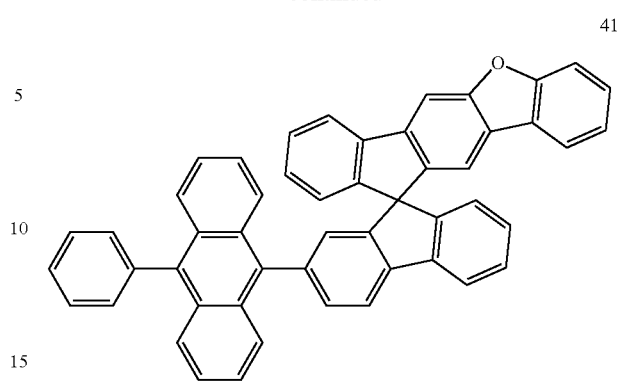
42
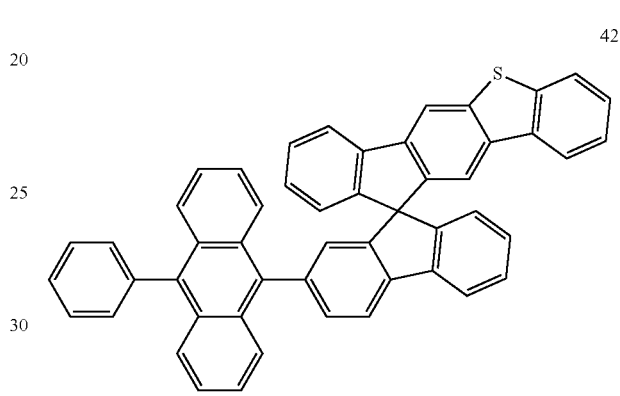
43
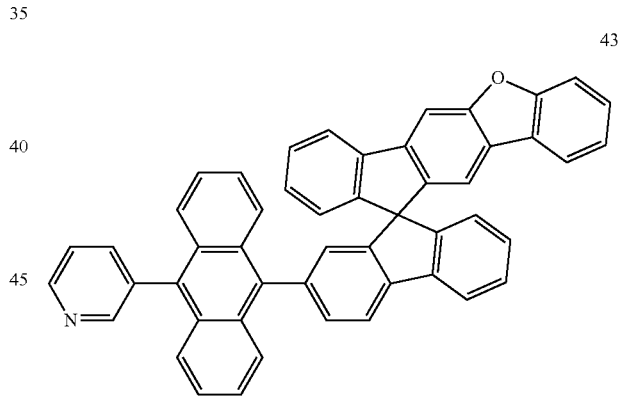
44
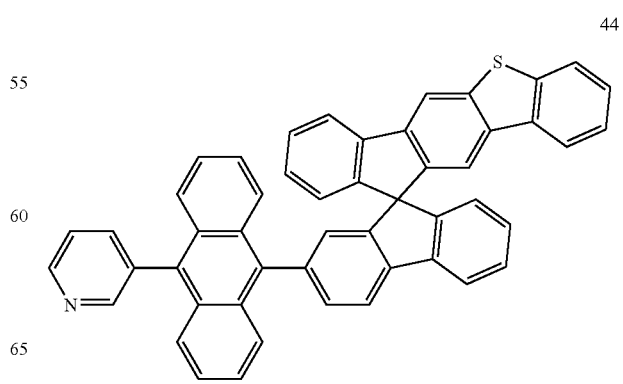

45
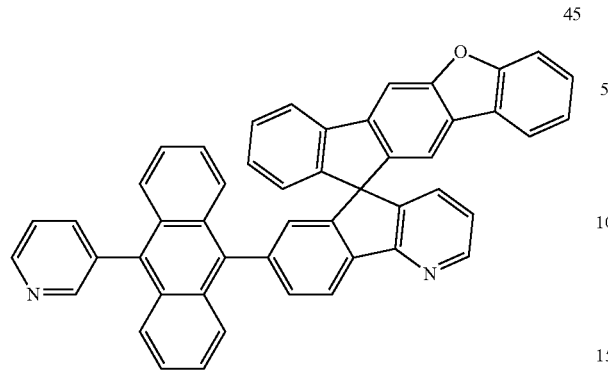
46
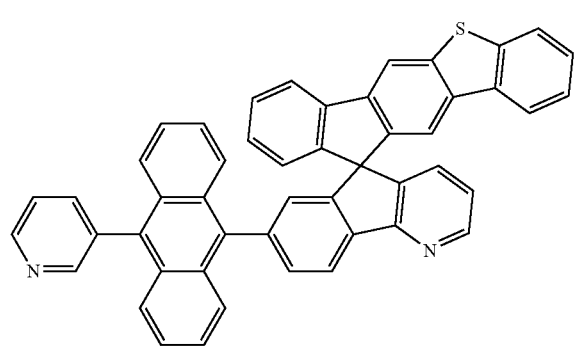
47
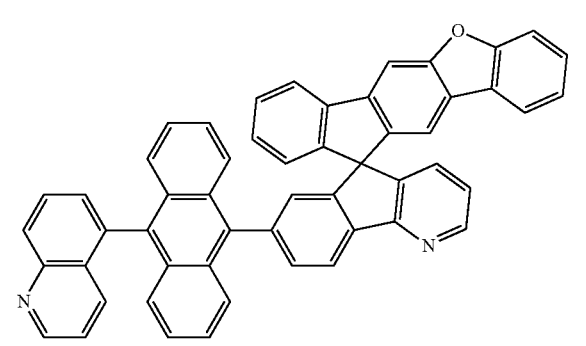
48
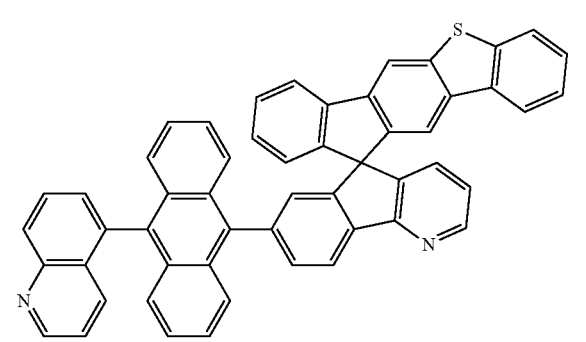
49
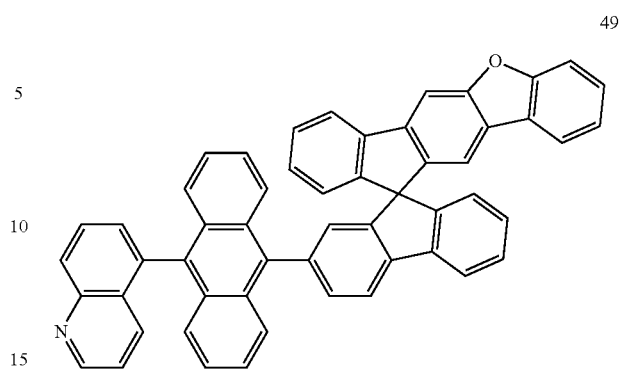
50
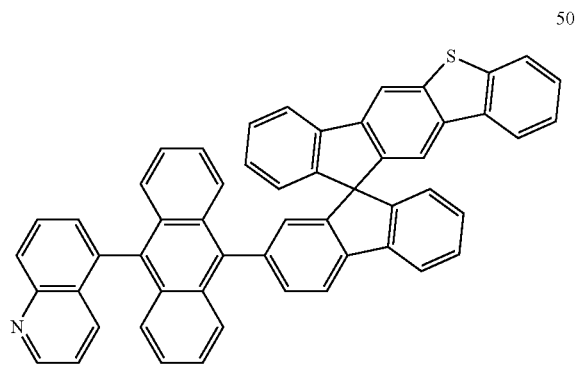
51
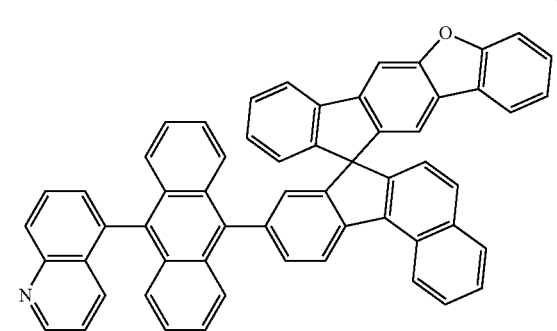
52
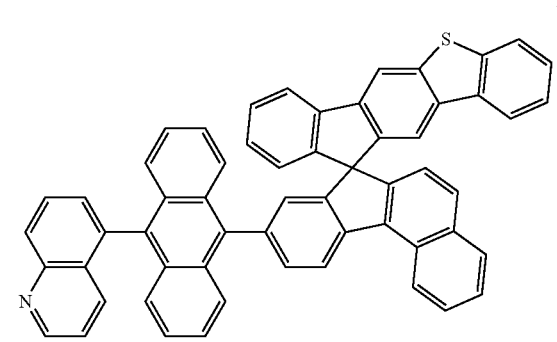

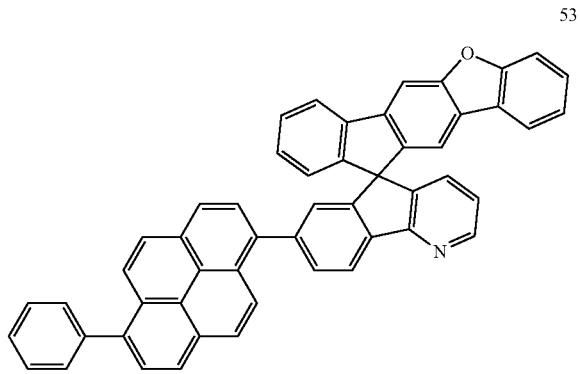
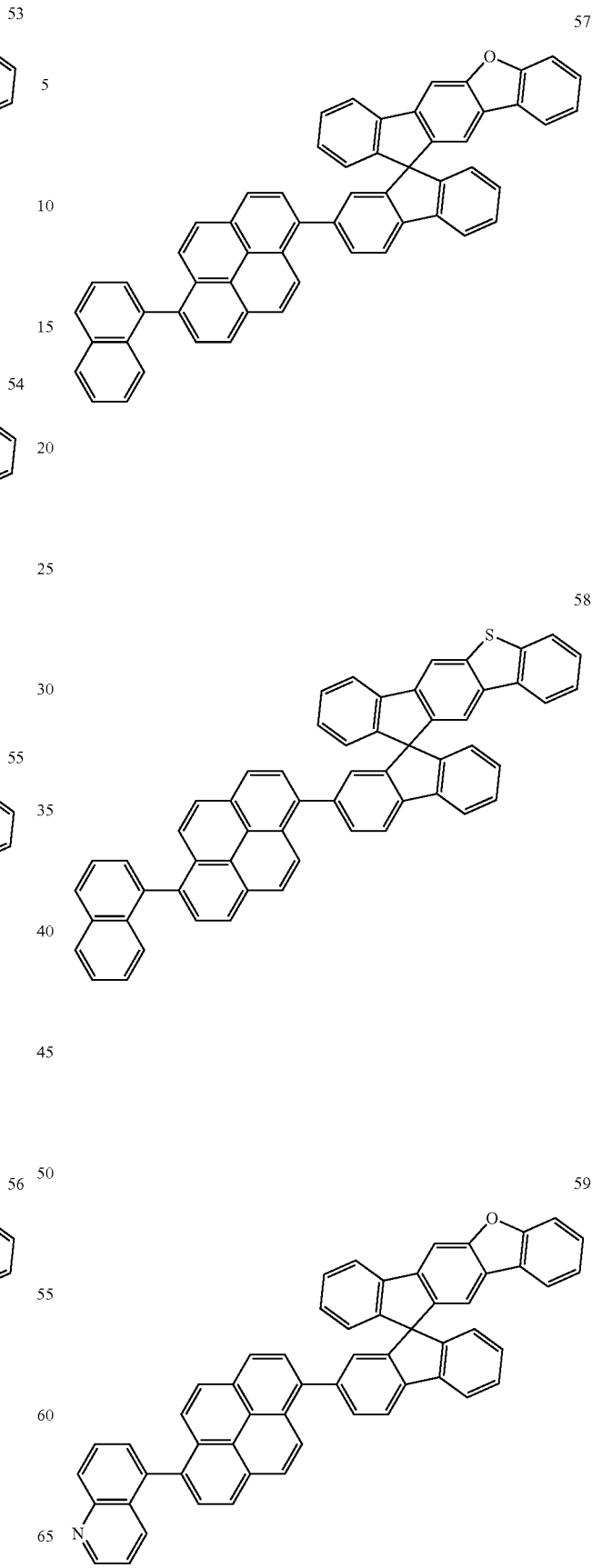

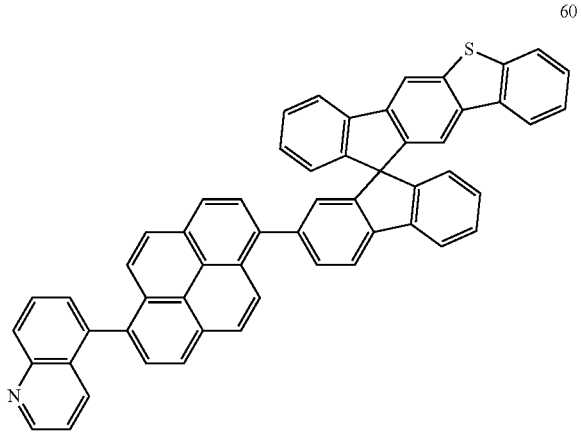
60
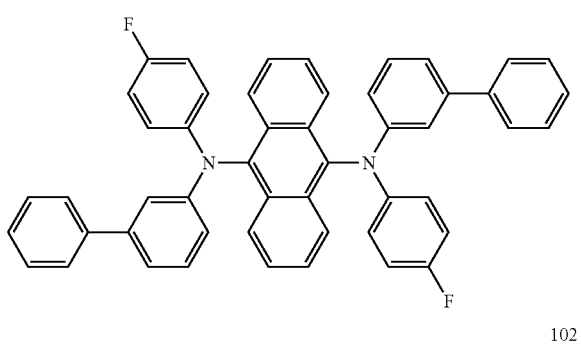
101
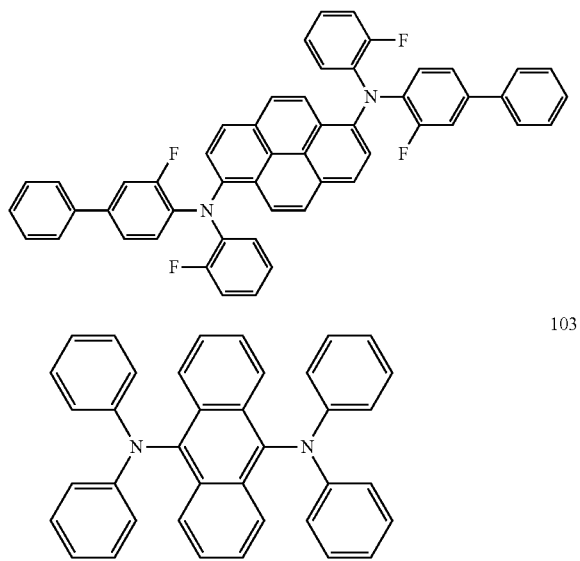
102
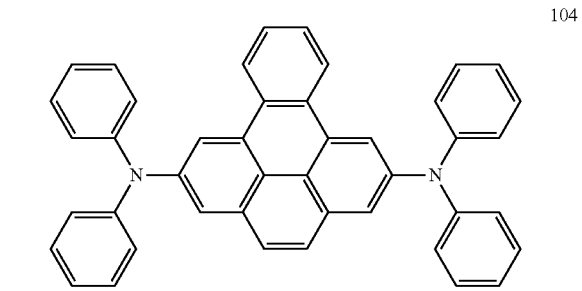
103
104
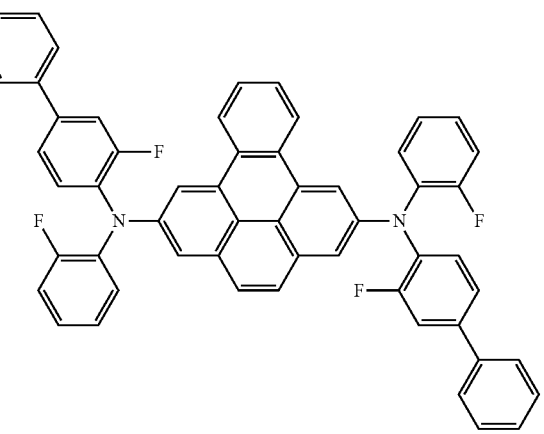
105
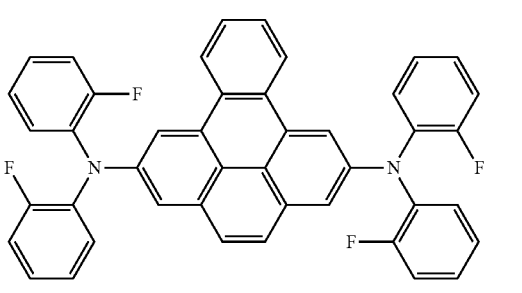
106
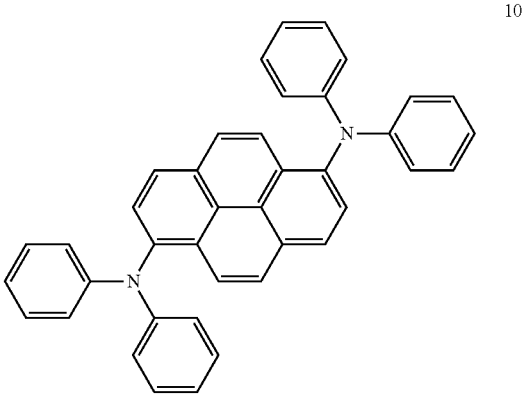
107
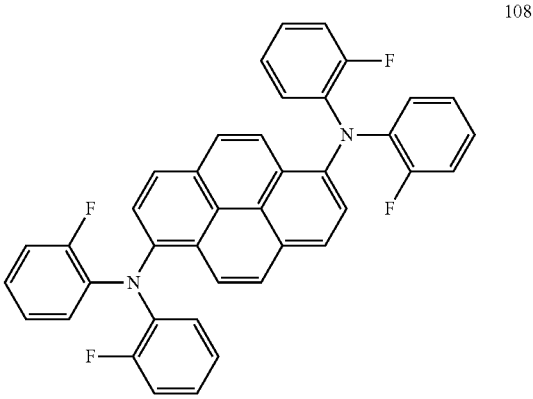
108

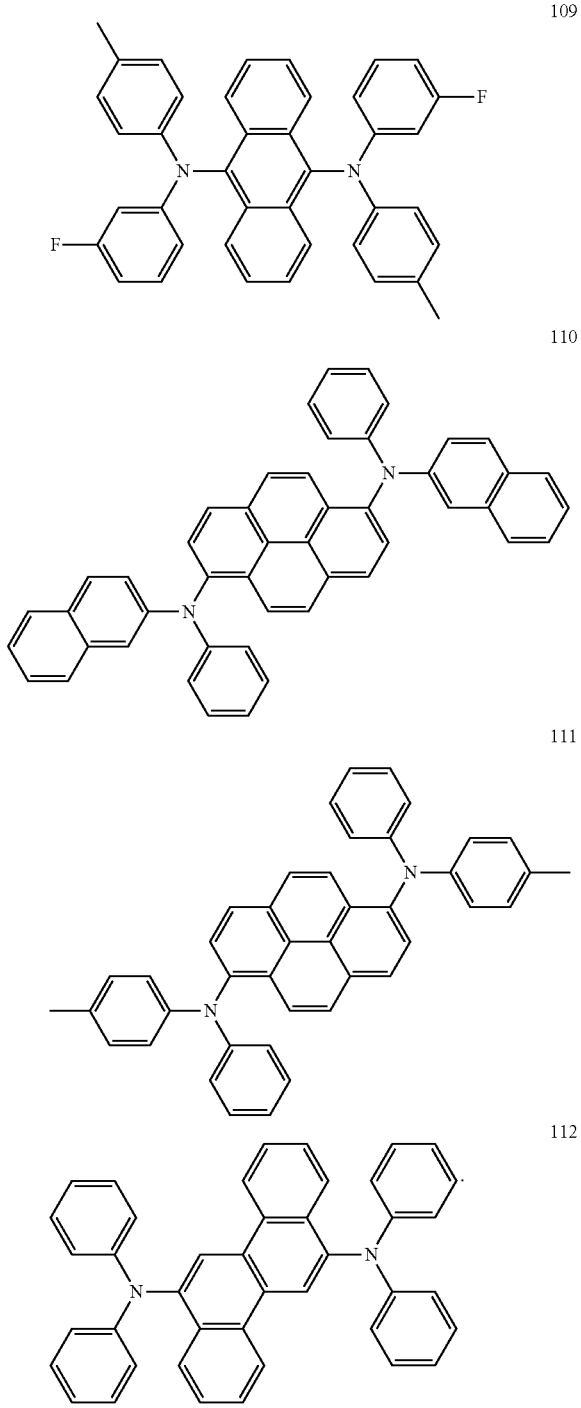

Since the first compound represented by Formula 1 has a spiro-bifluorene-based condensed-ring core, it may be possible to prevent or reduce degradation of the first compound that may be caused by electrons. Accordingly, an electronic device, for example, an organic light-emitting device, which includes the first compound represented by Formula 1, may have a long lifespan. Also, since the first compound represented by Formula 1 has a relatively high triplet energy (T1), a probability of annihilation between triplet excitons in the emission layer including the first compound represented by Formula 1 may increase, thereby increasing a triplet-triplet annihilation (TTA) effect. Accordingly, an electronic device, for example, an organic light-emitting device, which includes the first compound represented by Formula 1, may have high efficiency.

Also, in the first compound represented by Formula 1, $L_1$ and $L_2$ may each independently be a substituted or unsubstituted condensed polycyclic group that has three or more carbocyclic groups condensed with each other and does not include a heteroatom, and a1 and a2 (respectively indicating the number of $L_1$(s) and the number of L(s)) are not zero. That is, in Formula 1, "$L_1$" is included in the group represented by $*-[(L_1)_{a1}-(R_1)_{b1}]$ and "$L_2$" is included in the group represented by $*-[(L_2)_{a2}-(R_2)_{b2}]$. Also, in Formula 1, the sum of c1 and c2 (c1+c2) may be one or greater. That is, in Formula 1, at least one selected from the group represented by $*-[(L_1)_{a1}-(R_1)_{b1}]$ and the group represented by $*-[(L_2)_{a2}-(R_2)_{b2}]$ is present. Thus, for example, when the first compound represented by Formula 1 is used as the host in the emission layer of the organic light-emitting device, a suitable energy level between the host and the dopant may be effectively adjusted, thereby achieving an efficient energy transfer between the host and the dopant. Accordingly, an electronic device, for example, an organic light-emitting device, which includes the first compound represented by Formula 1, may have high efficiency.

Further, an organic light-emitting device including both the first compound and the second compound represented by Formula 501 may have high efficiency and high luminance. For example, both the first compound and the second compound may be included in the emission layer of the organic light-emitting device. In some embodiments, the first compound included in the emission layer may act as the host, and the second compound included in the emission layer may act as the dopant (e.g., a fluorescent dopant).

In various embodiments, an amount of the first compound in the emission layer may be greater than an amount of the second compound.

In various embodiments, an amount of the second compound in the emission layer may be in a range of about 0.01 to about 15 parts by weight based on 100 parts by weight of the first compound, but is not limited thereto. When the amount of the second compound is within the above range, it may be possible to implement an organic light-emitting device having high efficiency and high luminance without (or substantially without) emission quenching.

The first compound represented by Formula 1 may be synthesized by using any suitable organic synthesis method. Synthesis methods for the first compound should become apparent to one of ordinary skill in the art by referring to the examples described below.

In various embodiments, in the organic light-emitting device,
 the first electrode may be an anode,
 the second electrode may be a cathode, and
 the organic layer may include a hole transport region between the first electrode and the emission layer, and an electron transport region between the emission layer and the second electrode.

The hole transport region may include a hole injection layer, a hole transport layer, an emission auxiliary layer, an electron blocking layer, or a combination thereof, and the electron transport region may include a hole blocking layer, an electron transport layer, an electron injection layer, or a combination thereof.

The term "first compound", as used herein, may refer to i) a single compound represented by Formula 1 (e.g., Compound 1), or ii) a mixture of two or more different compounds represented by Formula 1 (e.g., a mixture of Compounds 1 and 2).

The term "second compound", as used herein, may refer to i) a single compound represented by Formula 501 (e.g., Compound 107), or ii) a mixture of two or more different compounds represented by Formula 501 (e.g., a mixture of Compound 107 and 111).

The term "organic layer", as used herein, may refer to a single layer and/or a plurality of layers between the first electrode and the second electrode of an organic light-emitting device. A material included in the "organic layer" is not limited to an organic material.

Description of FIG. 1

Figure 1:
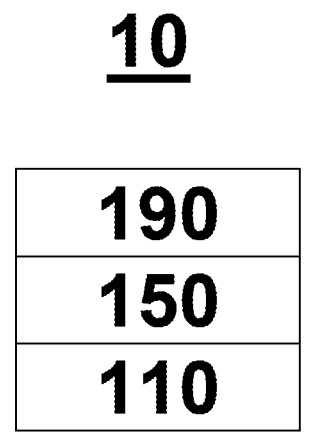

FIG. 1 is a schematic view of an organic light-emitting device 10 according to an embodiment. The organic light-emitting device 10 includes a first electrode 110, an organic layer 150, and a second electrode 190.

Hereinafter, the structure of the organic light-emitting device 10 according to an embodiment and a method of manufacturing the organic light-emitting device 10 will be described in connection with FIG. 1.

First Electrode 110

In FIG. 1, a substrate may be additionally disposed (e.g., positioned) under the first electrode 110 or above the second electrode 190. The substrate may be a glass substrate or a plastic substrate, each having excellent mechanical strength, thermal stability, transparency, surface smoothness, ease of handling, and/or water-resistance.

The first electrode 110 may be formed by depositing or sputtering a material for forming the first electrode 110 on the substrate. When the first electrode 110 is an anode, the material for forming the first electrode 110 may be selected from materials with a high work function to facilitate hole injection.

The first electrode 110 may be a reflective electrode, a semi-transmissive electrode, or a transmissive electrode. When the first electrode 110 is a transmissive electrode, a material for forming the first electrode 110 may be selected from indium tin oxide (ITO), indium zinc oxide (IZO), tin oxide ($SnO_2$), zinc oxide (ZnO), and a combination thereof, but is not limited thereto. When the first electrode 110 is a semi-transmissive electrode or a reflective electrode, as a material for forming the first electrode 110, magnesium (Mg), silver (Ag), aluminum (Al), aluminum-lithium (Al—Li), calcium (Ca), magnesium-indium (Mg—In), magnesium-silver (Mg—Ag), or a combination thereof may be used. However, the material for forming the first electrode 110 is not limited thereto.

The first electrode 110 may have a single-layered structure, or a multi-layered structure including two or more layers. For example, the first electrode 110 may have a three-layered structure of ITO/Ag/ITO, but the structure of the first electrode 110 is not limited thereto.

Organic Layer 150

The organic layer 150 may be disposed (e.g., positioned) on the first electrode 110. The organic layer 150 may include an emission layer.

The organic layer 150 may further include a hole transport region between the first electrode 110 and the emission layer, and an electron transport region between the emission layer and the second electrode 190.

Hole Transport Region in Organic Layer 150

The hole transport region may have i) a single-layered structure including a single layer including a single material, ii) a single-layered structure including a single layer including a plurality of different materials, or iii) a multi-layered structure having a plurality of layers including a plurality of different materials.

The hole transport region may include at least one layer selected from a hole injection layer (HIL), a hole transport layer (HTL), an emission auxiliary layer, and an electron blocking layer (EBL).

For example, the hole transport region may have a single-layered structure including a single layer including a plurality of different materials, or a multi-layered structure having a structure of hole injection layer/hole transport layer, hole injection layer/hole transport layer/emission auxiliary layer, hole injection layer/emission auxiliary layer, hole transport layer/emission auxiliary layer or hole injection layer/hole transport layer/electron blocking layer, wherein for each structure, constituting layers are sequentially stacked from the first electrode 110 in this stated order, but the structure of the hole transport region is not limited thereto.

The hole transport region may include at least one selected from m-MTDATA, TDATA, 2-TNATA, NPB (NPD), 8-NPB, TPD, Spiro-TPD, Spiro-NPB, methylated NPB, TAPC, HMTPD, TCTA (4,4',4"-tris(N-carbazolyl)triphenylamine), PANI/DBSA (polyaniline/dodecylbenzenesulfonic acid), PEDOT/PSS (poly(3,4-ethylenedioxythiophene)/poly(4-styrenesulfonate)), PANI/CSA (polyaniline/camphor sulfonic acid), PANI/PSS (polyaniline/poly(4-styrenesulfonate)), a compound represented by Formula 201, and a compound represented by Formula 202:

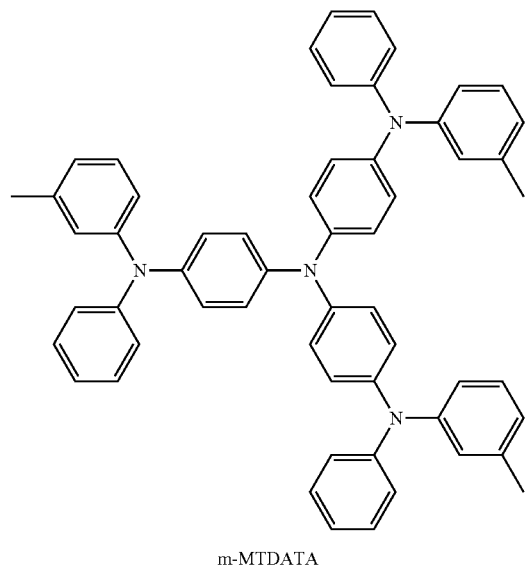

m-MTDATA

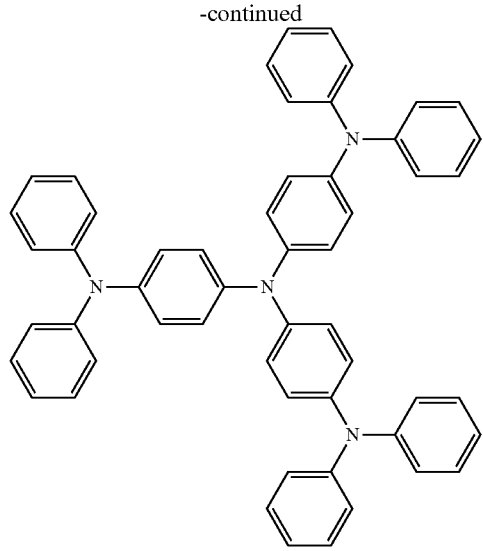
TDATA
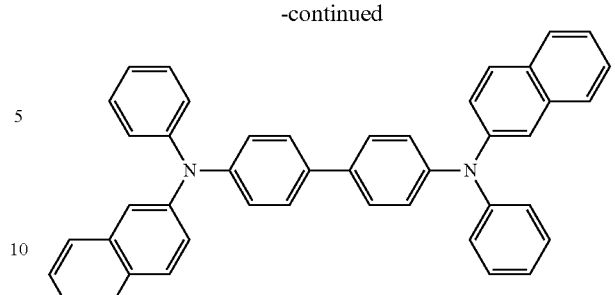
β-NPB
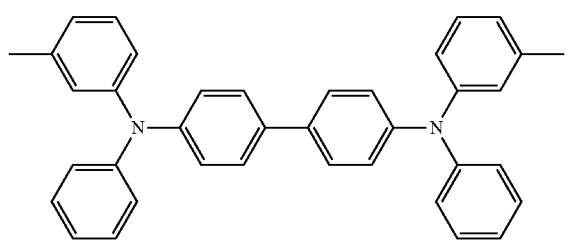
TPD
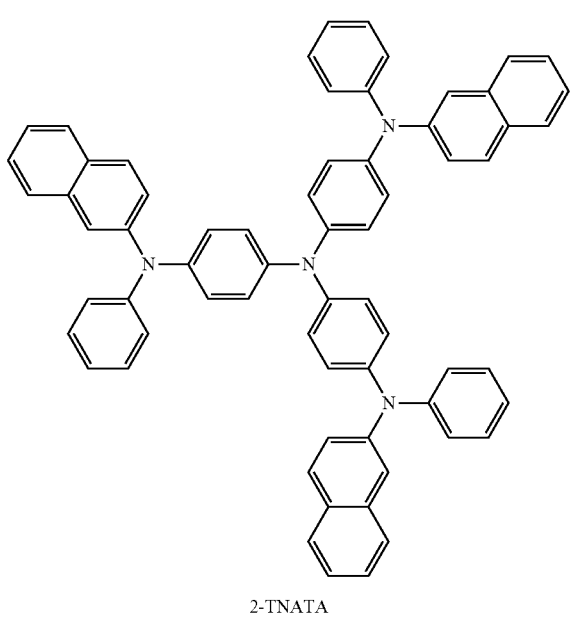
2-TNATA
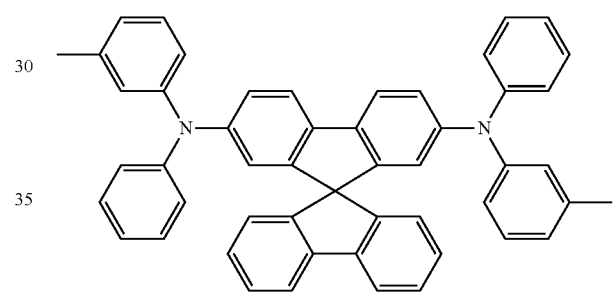
Spiro-TPD
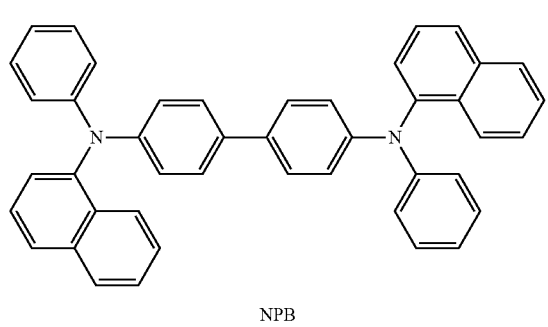
NPB
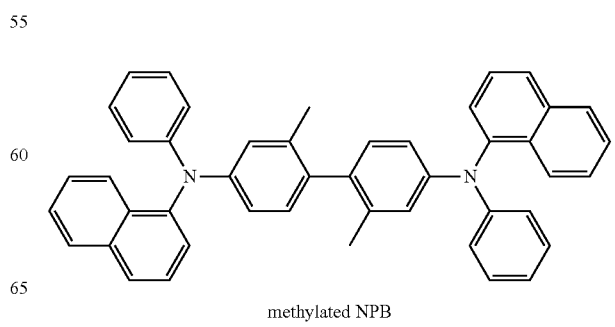
Spiro-NPB
methylated NPB

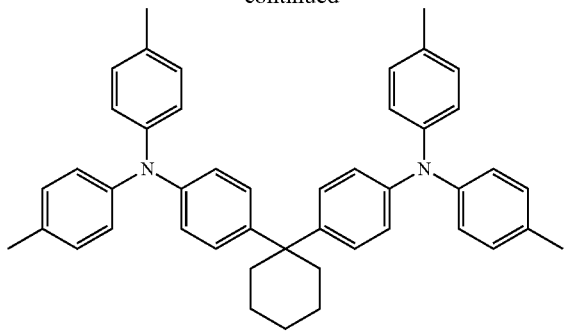

TAPC

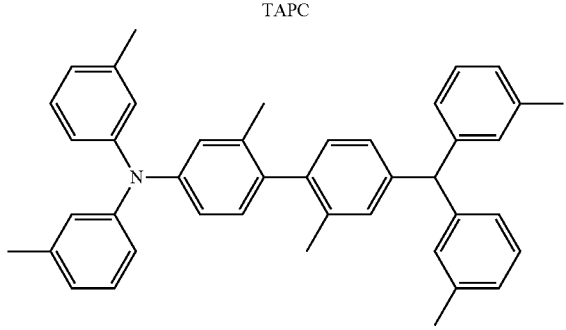

HMPTD

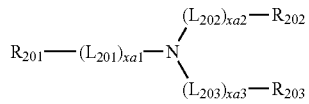

Formula 201

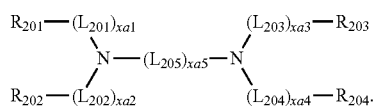

Formula 202

In Formulae 201 and 202, $L_{201}$ to $L_{204}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_{205}$ may be selected from *—O—*', *—S—*', *—N($Q_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently be an integer selected from 0 to 3, xa5 may be an integer selected from 1 to 10, and $R_{201}$ to $R_{204}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, in Formula 202, $R_{201}$ and $R_{202}$ may optionally be linked to each other via a single bond, a dimethyl-methylene group, or a diphenyl-methylene group, and $R_{203}$ and $R_{204}$ may optionally be linked to each other via a single bond, a dimethyl-methylene group, or a diphenyl-methylene group.

In various embodiments, in Formulae 201 and 202, $L_{201}$ to $L_{205}$ may each independently be selected from the group consisting of:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In various embodiments, xa1 to xa4 may each independently be 0, 1, or 2.

In various embodiments, xa5 may be 1, 2, 3, or 4.

In various embodiments, $R_{201}$ to $R_{204}$ and $Q_{201}$ may each independently be selected from the group consisting of:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), wherein $Q_{31}$ to $Q_{33}$ are the same as described above.

In various embodiments, at least one selected from $R_{201}$ to $R_{203}$ in Formula 201 may each independently be selected from the group consisting of:

a fluorenyl group, a spiro-bifluorenyl group, a carbazolyl group, a dibenzofuranyl group, and a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments of the present disclosure are not limited thereto.

In various embodiments, in Formula 202, i) $R_{201}$ and $R_{202}$ may be connected (e.g., linked) to each other via a single bond, and/or ii) $R_{203}$ and $R_{204}$ may be connected (e.g., linked) to each other via a single bond.

In various embodiments, at least one selected from $R_{201}$ to $R_{204}$ in Formula 202 may be selected from the group consisting of:

a carbazolyl group; and a carbazolyl group substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group;

but embodiments of the present disclosure are not limited thereto.

The compound represented by Formula 201 may be represented by Formula 201A:

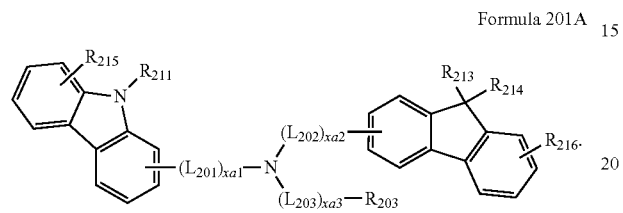

Formula 201A

For example, the compound represented by Formula 201 may be represented by Formula 201A(1), but is not limited thereto:

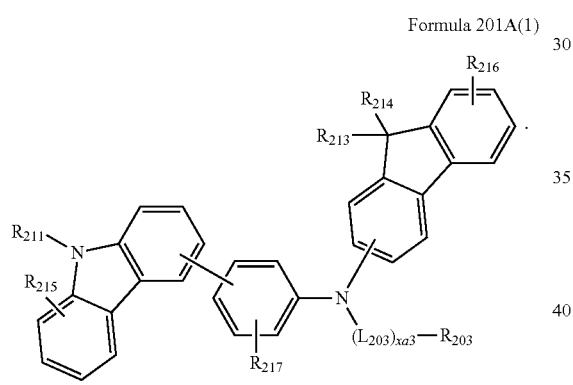

Formula 201A(1)

For example, the compound represented by Formula 201 may be represented by Formula 201A-1, but is not limited thereto:

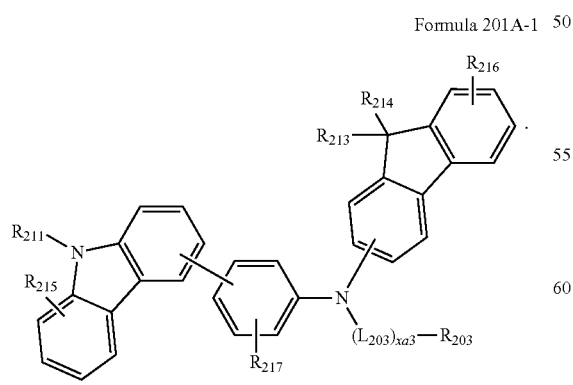

Formula 201A-1

In various embodiments, the compound represented by Formula 202 may be represented by Formula 202A:

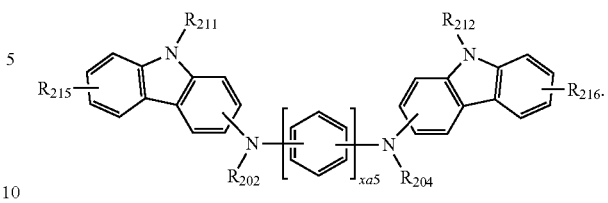

Formula 202A

In various embodiments, the compound represented by Formula 202 may be represented by Formula 202A-1:

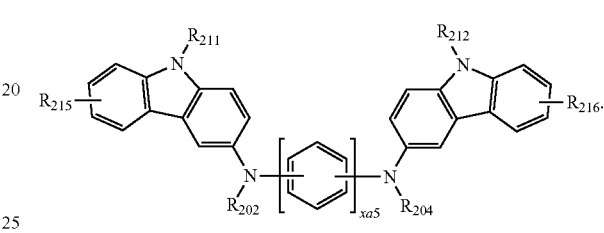

Formula 202A-1

In Formulae 201A, 201A(1), 201A-1, 202A, and 202A-1, $L_{201}$ to $L_{203}$, xa1 to xa3, xa5, and $R_{202}$ to $R_{204}$ are the same as described above.

descriptions of $R_{211}$ and $R_{212}$ may each independently be the same as the description provided above in connection with $R_{203}$.

$R_{213}$ to $R_{217}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

The hole transport region may include at least one compound selected from Compounds HT1 to HT39, but is not limited thereto:

HT1
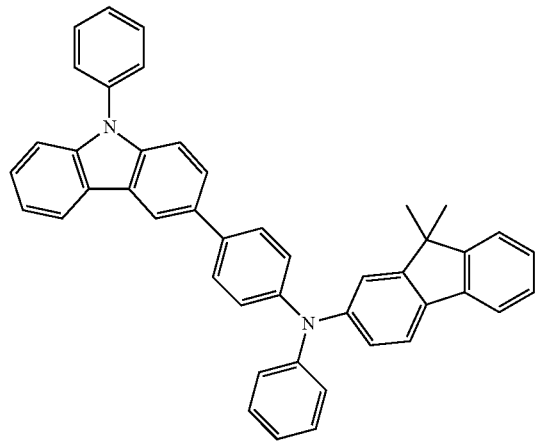
HT2
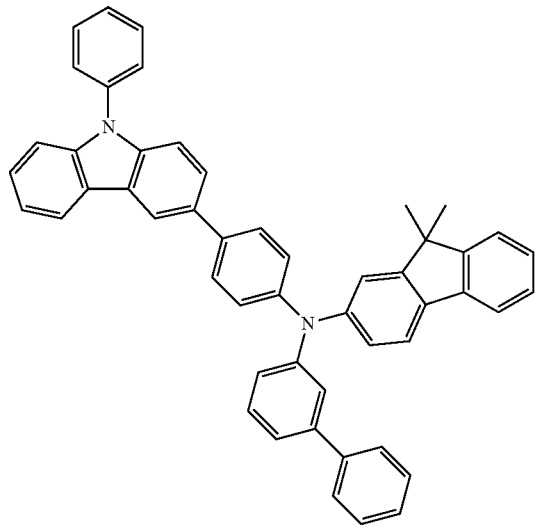
HT3
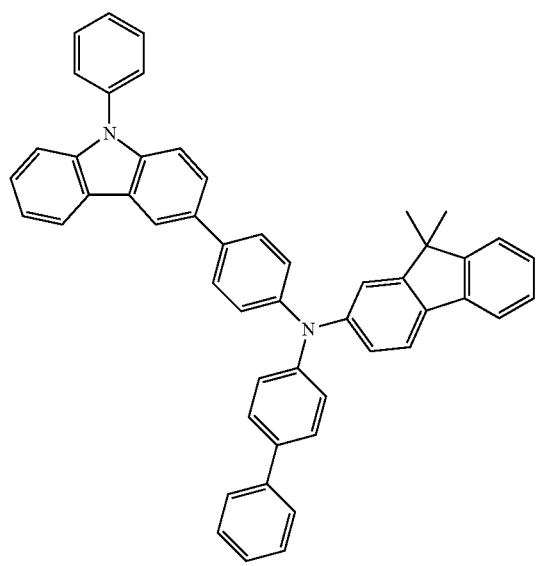
HT4
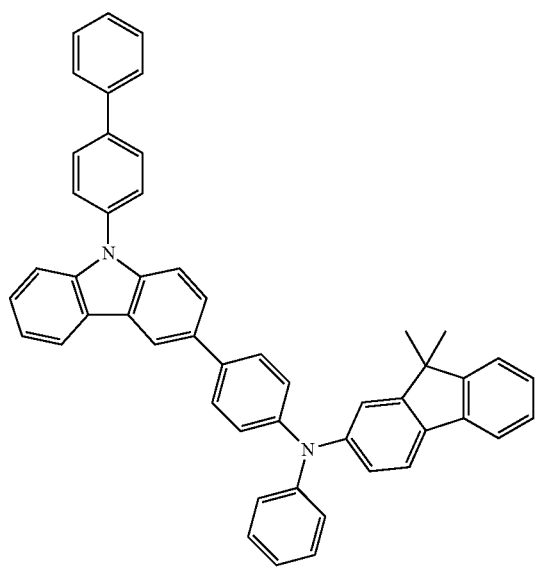

-continued
HT5
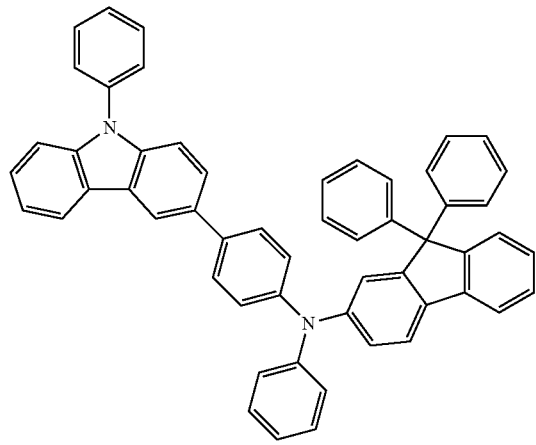
HT6
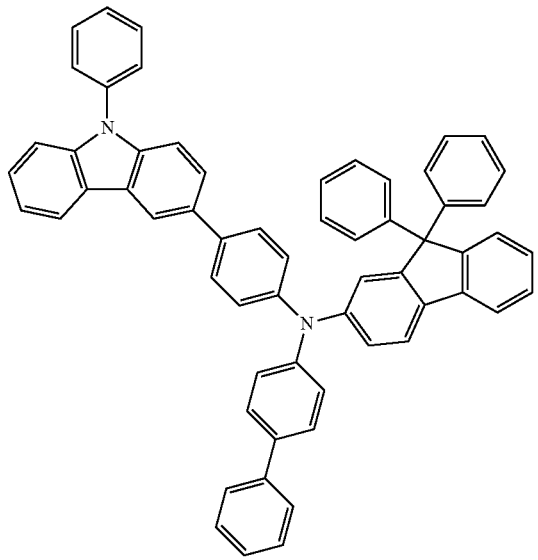
HT7
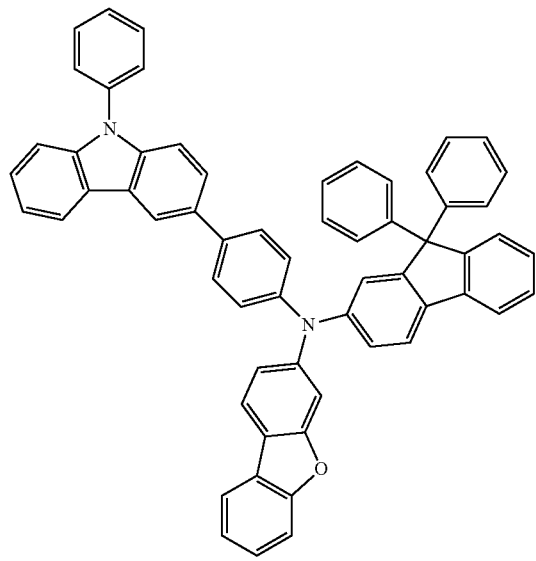
HT8
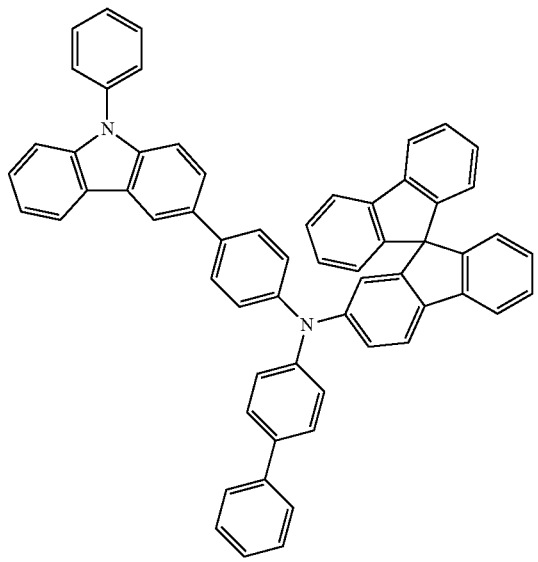

-continued
HT9
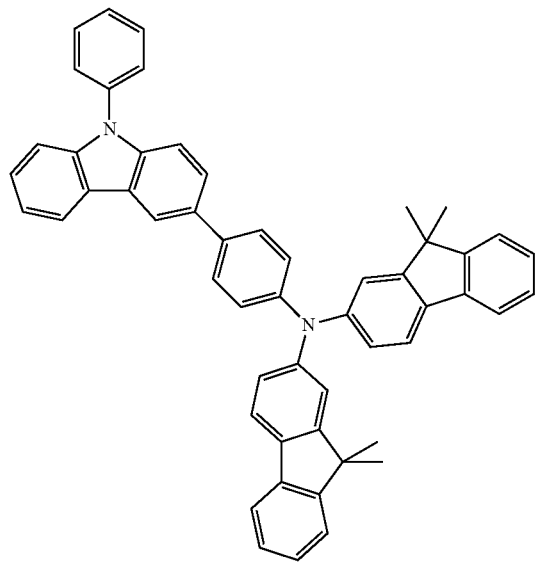
HT10
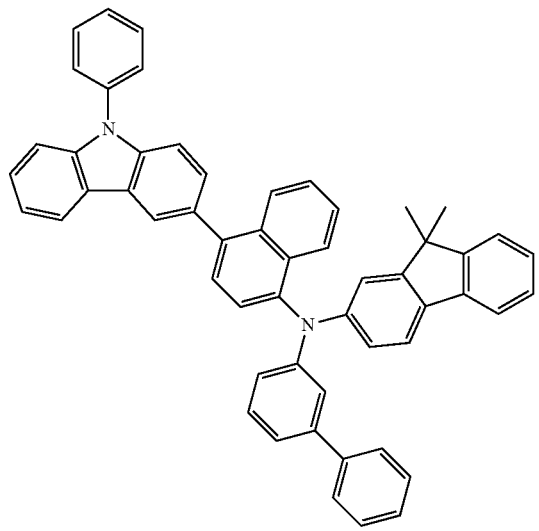
HT11
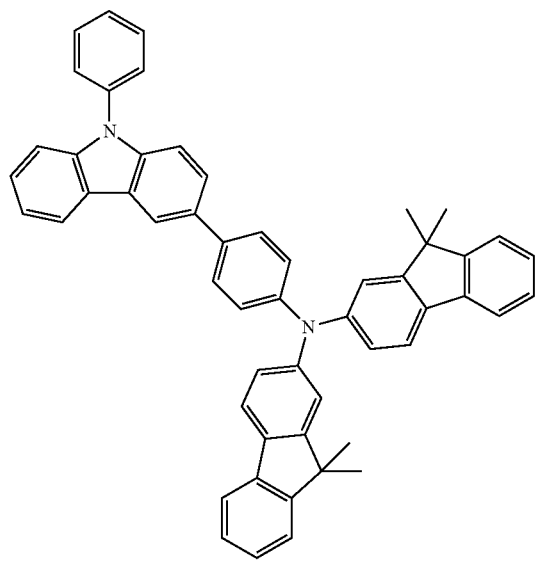
HT12
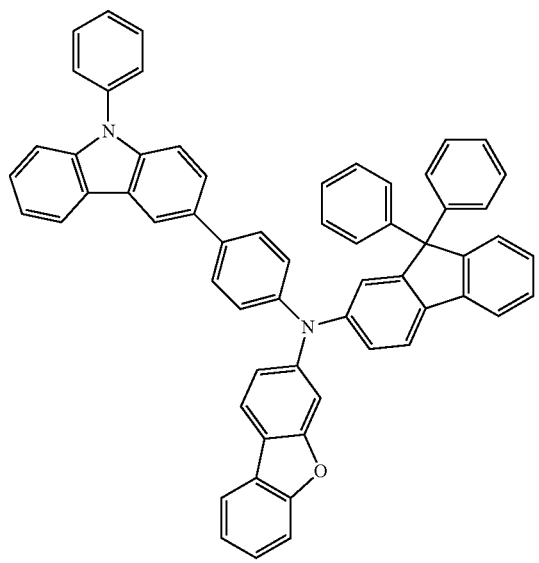

-continued
HT13
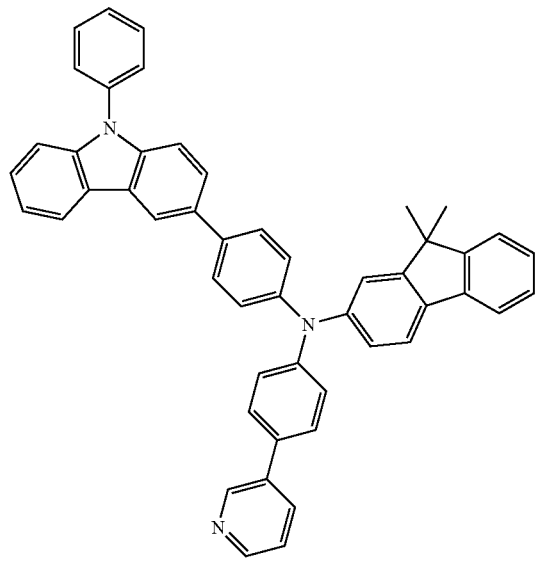
HT14
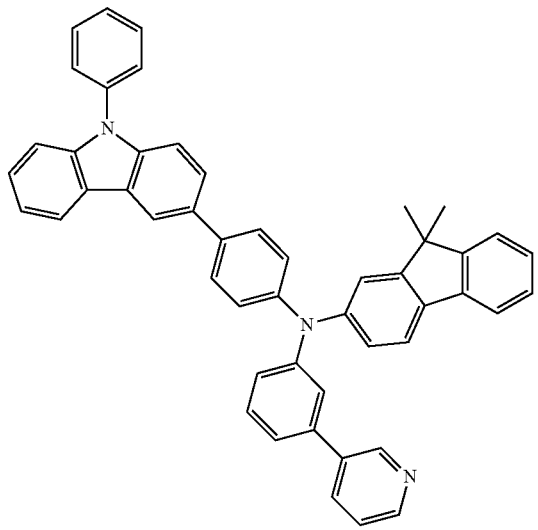
HT15
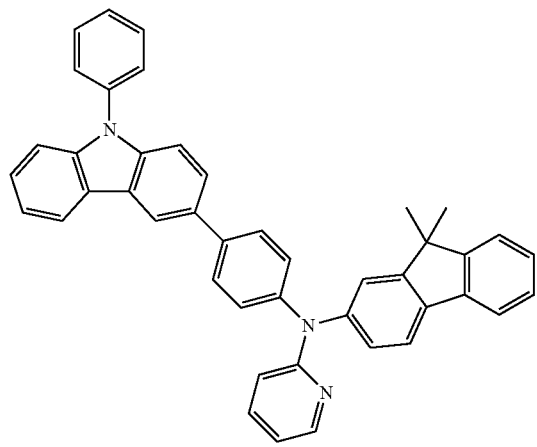
HT16
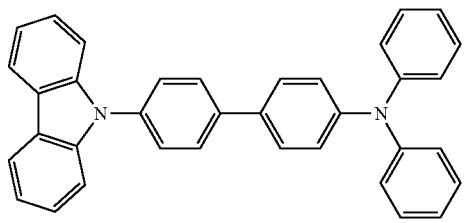
HT17
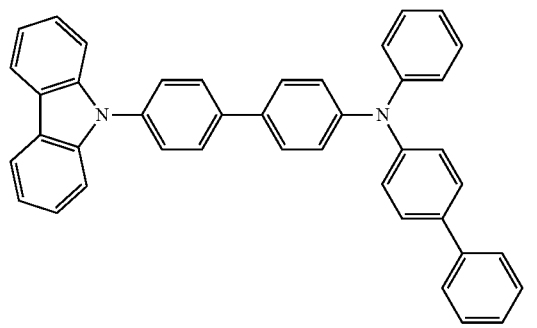
HT18
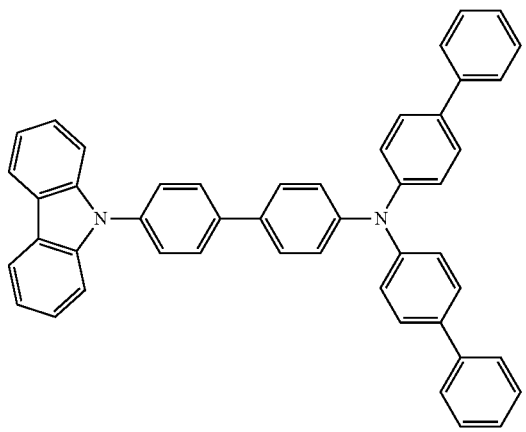

-continued
HT19
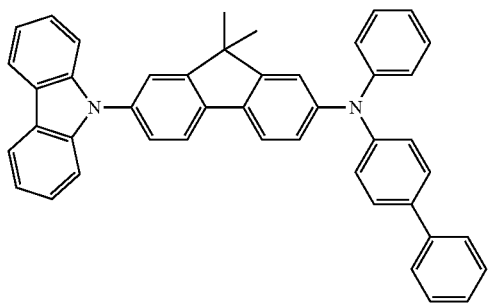
HT20
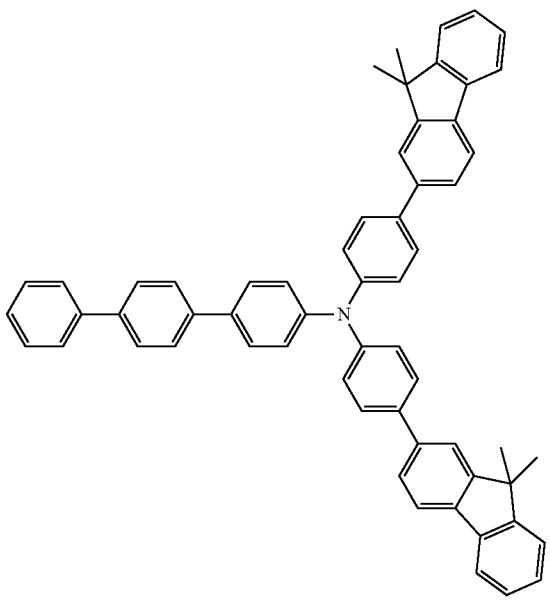
HT21
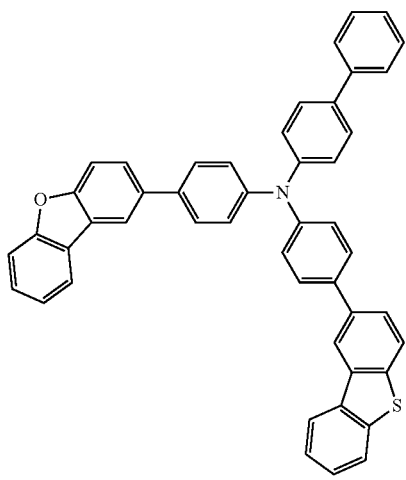
HT22
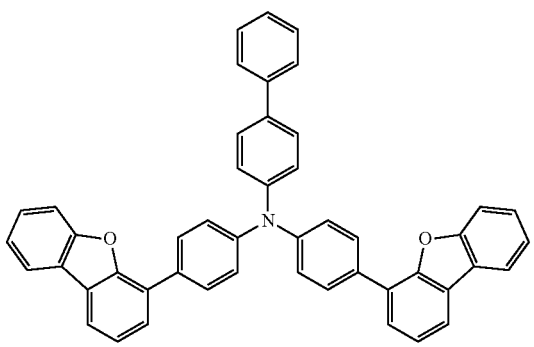
HT23
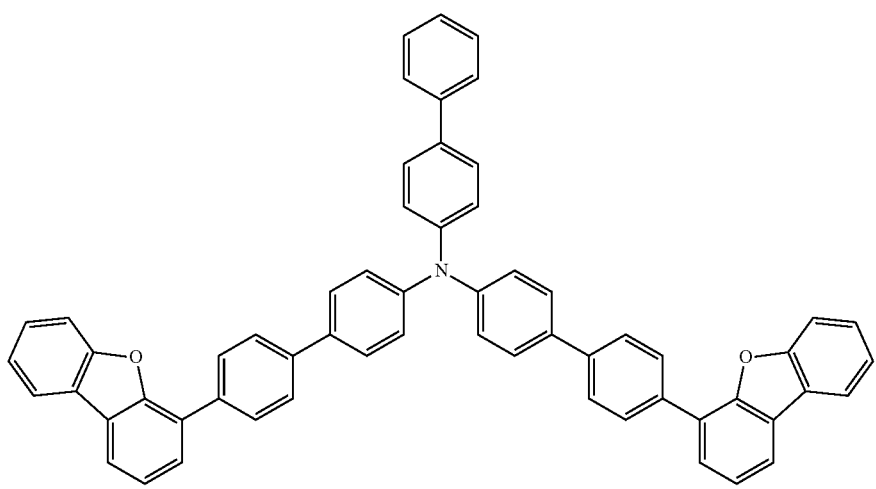

-continued
HT24
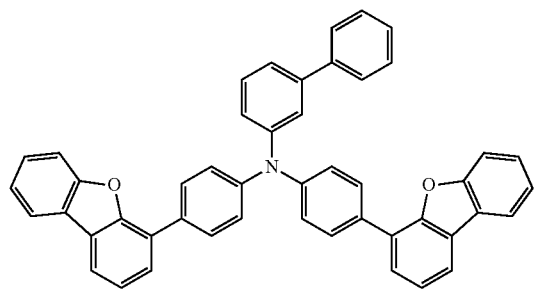
HT25
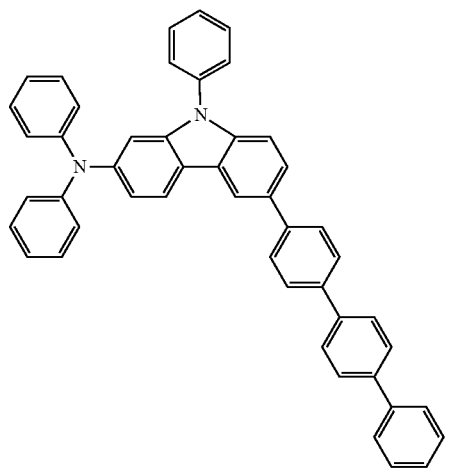
HT26
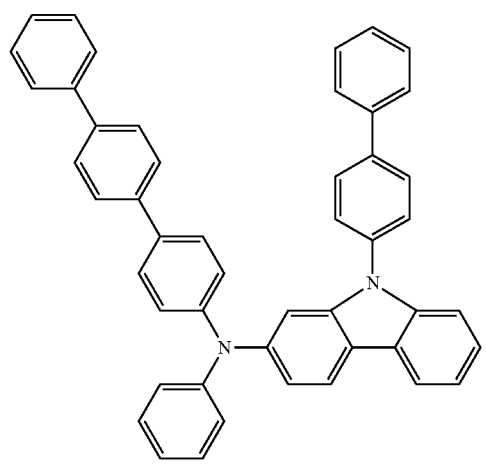
HT27
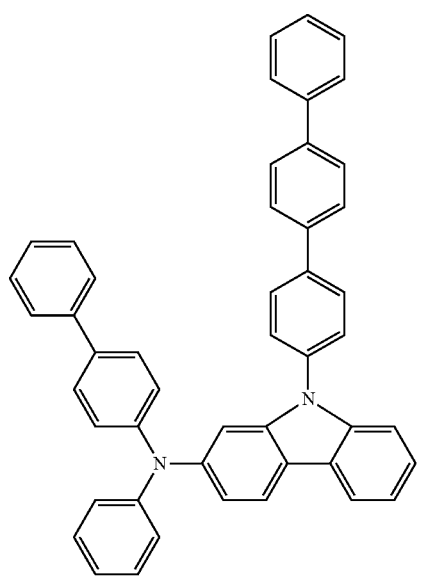
HT28
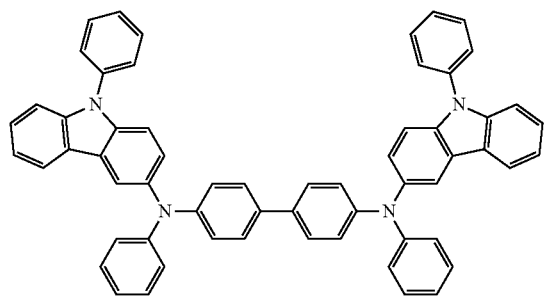
HT29
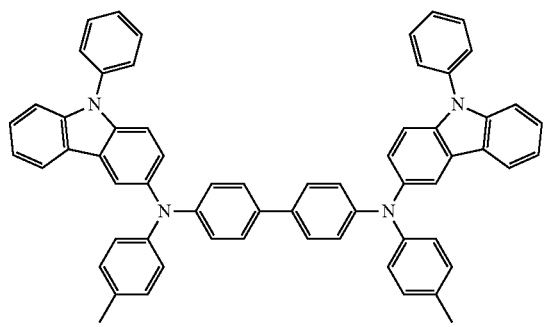

-continued
HT30
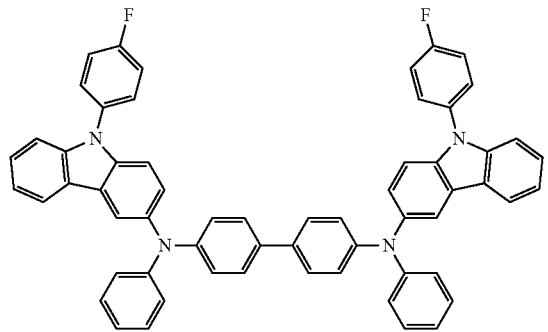
HT31
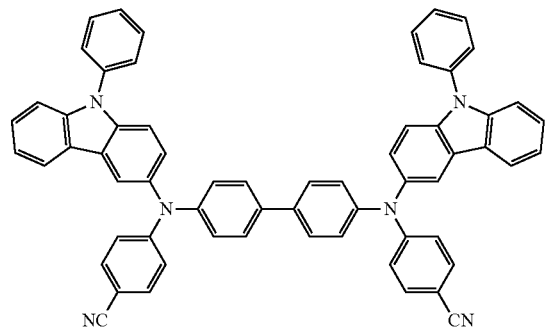
HT32
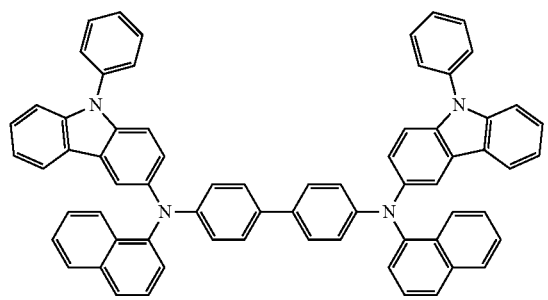
HT33
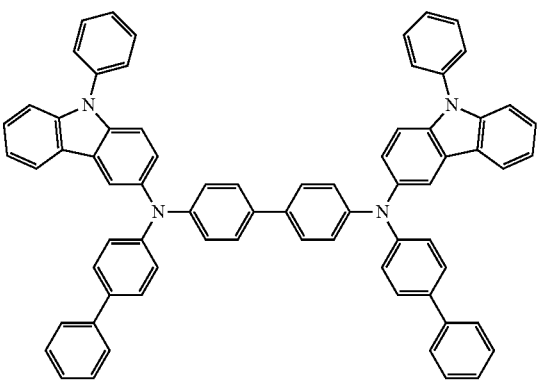
HT34
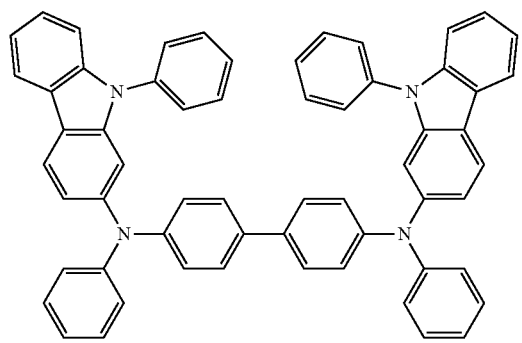
HT35
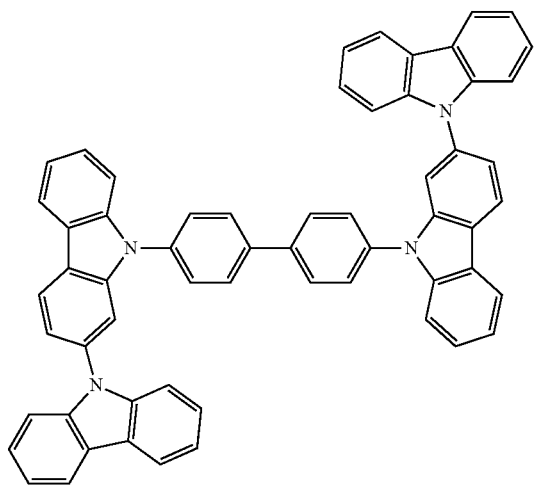

111                                                                          112

HT36
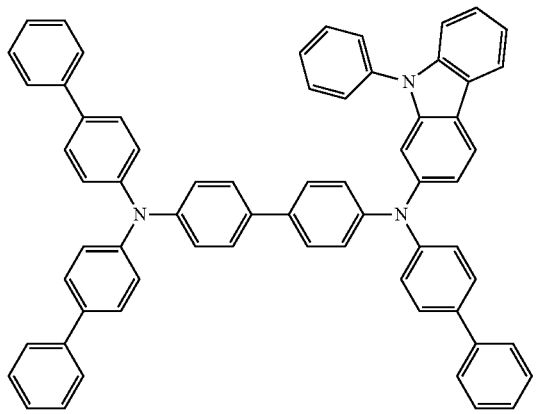

HT37
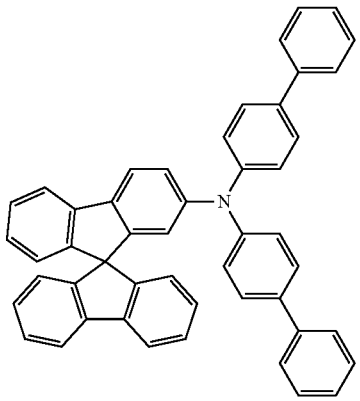

HT38
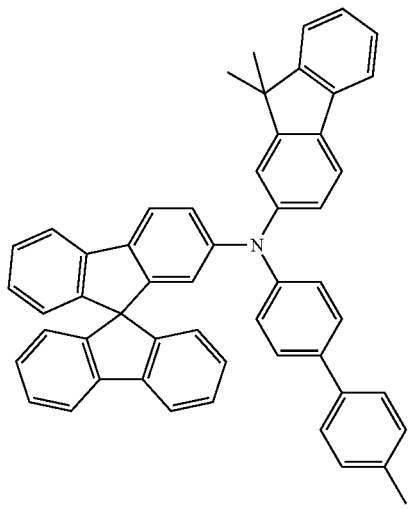

HT39
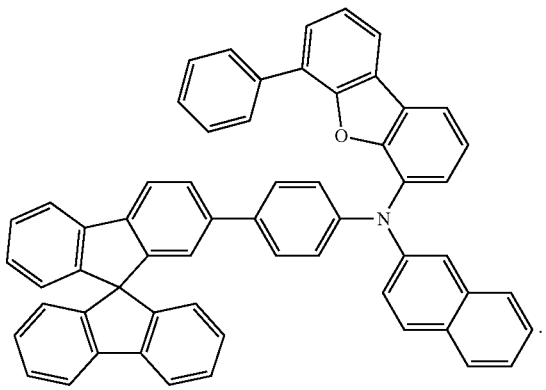

A thickness of the hole transport region may be in a range of about 100 Å to about 10,000 Å, for example, about 100 Å to about 1,000 Å. When the hole transport region includes at least one selected from a hole injection layer and a hole transport layer, the thickness of the hole injection layer may be in a range of about 100 Å to about 9,000 Å, for example, about 100 Å to about 1,000 Å, and the thickness of the hole transport layer may be in a range of about 50 Å to about 2,000 Å, for example, about 100 Å to about 1,500 Å. When the thicknesses of the hole transport region, the hole injection layer, and the hole transport layer are within any of these ranges, satisfactory (or suitable) hole transporting characteristics may be obtained without a substantial increase in driving voltage.

The emission auxiliary layer may increase light-emission efficiency by compensating for an optical resonance distance according to the wavelength of light emitted by an emission layer, and the electron blocking layer may block or reduce the flow of electrons from an electron transport region. The emission auxiliary layer and the electron blocking layer may include any of the materials as described above.

P-Dopant

The hole transport region may further include, in addition to the materials described above, a charge-generation material for the improvement of conductive properties. The charge-generation material may be homogeneously or non-homogeneously dispersed in the hole transport region.

The charge-generation material may be, for example, a p-dopant.

In one embodiment, the p-dopant may have a lowest unoccupied molecular orbital (LUMO) of −3.5 eV or less.

The p-dopant may include at least one selected from a quinone derivative, a metal oxide, and a cyano group-containing compound, but embodiments are not limited thereto.

For example, the p-dopant may include at least one selected from the group consisting of:
  quinone derivatives, such as TCNQ (tetracyanoquinodimethane) and/or F4-TCNQ (2,3,5,6-tetrafluoro-7,7,8,8-tetracyanoquinodimethane);
  metal oxides, such as tungsten oxide and/or molybdenum oxide;
  HAT-CN (1,4,5,8,9,11-hexaazatriphenylene-hexacarbonitrile); and
  a compound represented by Formula 221, but is not limited thereto:

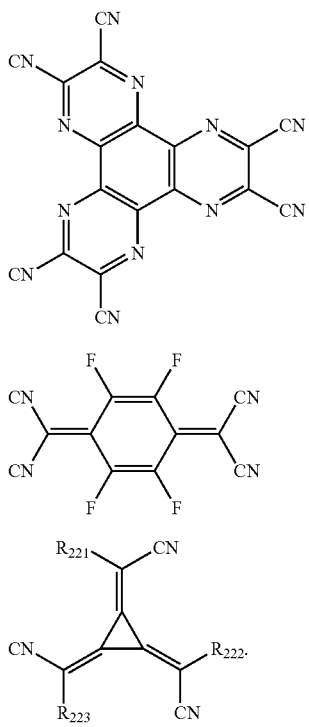

HAT-CN

F4-TCNQ

Formula 221

In Formula 221, $R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, wherein at least one selected from $R_{221}$ to $R_{223}$ may have a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and/or a $C_1$-$C_{20}$ alkyl group substituted with I.

Emission Layer in Organic Layer 150

When the organic light-emitting device 10 is a full color organic light-emitting device, the emission layer may be patterned into a red emission layer, a green emission layer, and/or a blue emission layer, according to a sub pixel. In various embodiments, the emission layer may have a stacked structure of two or more layers selected from a red emission layer, a green emission layer, and a blue emission layer, in which the two or more layers contact each other or are separated from each other. In various embodiments, the emission layer may include two or more materials selected from a red-light emission material, a green-light emission material, and a blue-light emission material, in which the two or more materials are mixed with each other in a single layer to emit white light. The emission layer may include a host and a dopant. The host may include the first compound represented by Formula 1 and the dopant may include the second compound represented by Formula 501. In various embodiments, the host may be the first compound and the dopant may be the second compound.

An amount of the dopant in the emission layer may be, for example, in a range of about 0.01 to about 15 parts by weight based on 100 parts by weight of the host, but is not limited thereto.

A thickness of the emission layer may be in a range of about 100 Å to about 1,000 Å, for example, about 200 Å to about 600 Å. When the thickness of the emission layer is within any of these ranges, excellent (or suitable) light-emission characteristics may be obtained without a substantial increase in driving voltage.

Electron Transport Region in Organic Layer 150

The electron transport region may have i) a single-layered structure including a single layer including a single material, ii) a single-layered structure including a single layer including a plurality of different materials, or iii) a multi-layered structure having a plurality of layers including a plurality of different materials.

The electron transport region may include at least one selected from a buffer layer, a hole blocking layer, an electron control layer, an electron transport layer (ETL), and an electron injection layer, but is not limited thereto.

For example, the electron transport region may have a structure of electron transport layer/electron injection layer, a structure of hole blocking layer/electron transport layer/electron injection layer, a structure of electron control layer/electron transport layer/electron injection layer, or a structure of buffer layer/electron transport layer/electron injection layer, wherein in each of these structures, constituting layers are sequentially stacked in this stated order from an emission layer. However, the structure of the electron transport layer is not limited thereto.

The electron transport region (e.g., a buffer layer, a hole blocking layer, an electron control layer, and/or an electron transport layer in the electron transport region) may include a metal-free compound containing at least one π electron-depleted nitrogen-containing ring.

The "π electron-depleted nitrogen-containing ring" as used herein may refer to a $C_1$-$C_{60}$ heterocyclic group having at least one *—N=*' moiety as a ring-forming moiety.

For example, the "π electron-depleted nitrogen-containing ring" may be i) a 5-membered to 7-membered hetero-monocyclic group having at least one *—N=*' moiety, ii) a hetero-polycyclic group in which two or more 5-membered to 7-membered hetero-monocyclic groups each having at least one *—N=*' moiety are condensed (e.g., fused) with each other, or iii) a hetero-polycyclic group in which at least one selected from 5-membered to 7-membered hetero-monocyclic groups, each having at least one *—N=*' moiety, is condensed (e.g., fused) with at least one $C_5$-$C_{60}$ carbocyclic group.

Non-limiting examples of the π electron-depleted nitrogen-containing ring are an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzoimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group, but are not limited thereto.

For example, the electron transport region may include a compound represented by Formula 601:

$$[Ar_{601}]_{xe11}-[(L_{601})_{xe1}-R_{601}]_{xe21}.$$   Formula 601

In Formula 601,
Ar$_{601}$ may be a substituted or unsubstituted $C_5$-$C_{60}$ carbocyclic group or a substituted or unsubstituted $C_1$-$C_{60}$ heterocyclic group,
xe11 may be 1, 2, or 3,
$L_{601}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group,
xe1 may be an integer selected from 0 to 5,
$R_{601}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $-Si(Q_{601})(Q_{602})(Q_{603})$, $-C(=O)(Q_{601})$, $-S(=O)_2(Q_{601})$, and $-P(=O)(Q_{601})(Q_{602})$,
wherein $Q_{601}$ to $Q_{603}$ may each independently be selected from a $C_1$-$C_{10}$ alkyl group, a $C_1$-$C_{10}$ alkoxy group, a phenyl group, a biphenyl group, a terphenyl group, and a naphthyl group, and
xe21 may be an integer selected from 1 to 5.

In various embodiments, at least one selected from xe11 number of Ar$_{601}$(s) and xe21 number of R$_{601}$ (s) may include the π electron-depletion nitrogen-containing ring described above.

In various embodiments, ring Ar$_{601}$ in Formula 601 may be selected from the group consisting of:
a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, phenanthroline group, a phenazine group, a benzoimidazole group, an iso-benzothiazole group, a benzoxazole group, an isobenzoxazole group, a triazole group, a tetrazole group, an oxadiazole group, a triazine group, a thiadiazol group, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzoimidazole group, an iso-benzothiazole group, a benzoxazole group, an isobenzoxazole group, a triazole group, a tetrazole group, an oxadiazole group, a triazine group, a thiadiazol group, an imidazopyridine group, an imidazopyrimidine group and an azacarbazole group, each substituted with at least one selected from deuterium, $-F$, $-Cl$, $-Br$, $-I$, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, $-Si(Q_{31})(Q_{32})(Q_{33})$, $-S(=O)_2(Q_{31})$, and $-P(=O)(Q_{31})(Q_{32})$,
wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xe11 in Formula 601 is two or more, two or more Ar$_{601}$(s) may be connected (e.g., linked) to each other via a single bond.

In various embodiments, Ar$_{601}$ in Formula 601 may be an anthracene group.

In various embodiments, Compound represented by Formula 601 may be represented by Formula 601-1:

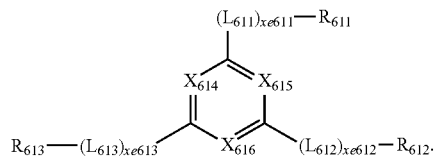

Formula 601-1

In Formula 601-1,
$X_{614}$ may be N or $C(R_{614})$; $X_{615}$ may be N or $C(R_{615})$; $X_{616}$ may be N or $C(R_{616})$; and at least one selected from $X_{614}$ to $X_{616}$ may be N,
descriptions of $L_{611}$ to $L_{613}$ may each independently be the same as the description provided above in connection with $L_{601}$,
descriptions of xe611 to xe613 may each independently be the same as the description provided above in connection with xe1, descriptions of $R_{611}$ to $R_{613}$ may each independently be the same as the description provided above in connection with $R_{601}$, and $R_{614}$ to $R_{616}$ may each independently be selected from hydrogen, deuterium, —F, —Cl, —Br, —I, a hydroxyl group, a cyano group, a nitro group, an am idino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In various embodiments, $L_{601}$ and $L_{611}$ to $L_{613}$ in Formulae 601 and 601-1 may each independently be selected from the group consisting of:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzoimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzoimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an am idino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, but embodiments are not limited thereto.

In various embodiments, xe1 and xe611 to xe613 in Formulae 601 and 601-1 may each independently be 0, 1, or 2.

In various embodiments, $R_{601}$ and $R_{611}$ to $R_{613}$ in Formulae 601 and 601-1 may each independently be selected from the group consisting of:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and —S(═O)$_2$(Q$_{601}$) and —P(═O)(Q$_{601}$)(Q$_{602}$), wherein Q$_{601}$ and Q$_{602}$ are the same as described above.

The electron transport region may include at least one compound selected from Compounds ET1 to ET36, but is not limited thereto:

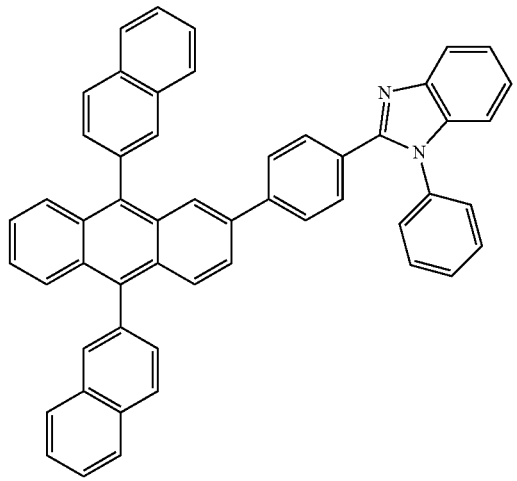

ET1

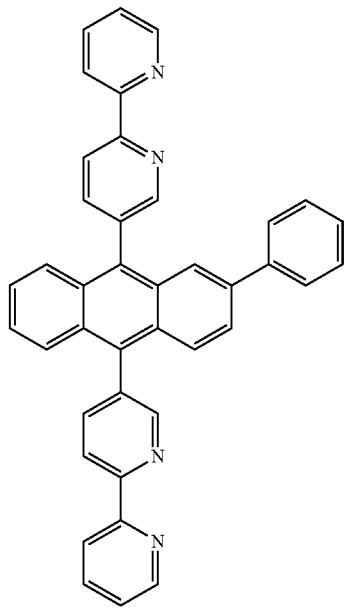

ET2

-continued
ET3
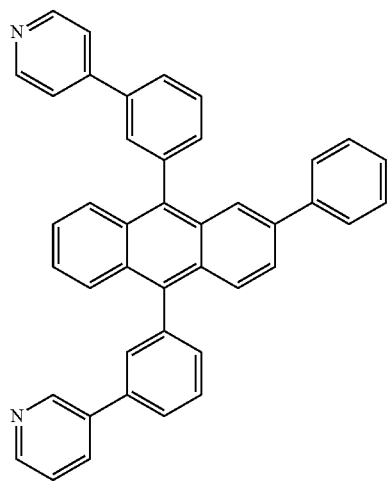
ET4
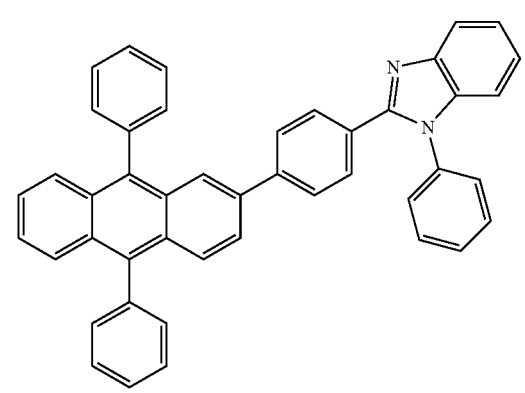
ET5
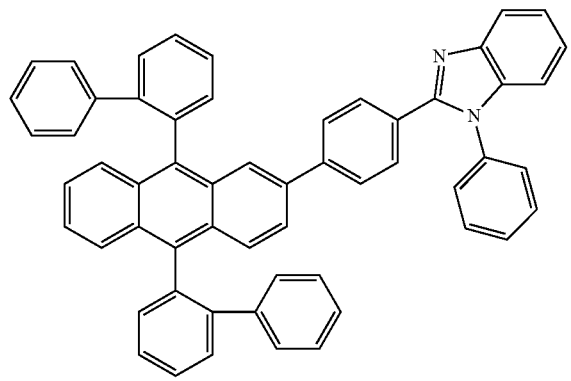
-continued
ET6
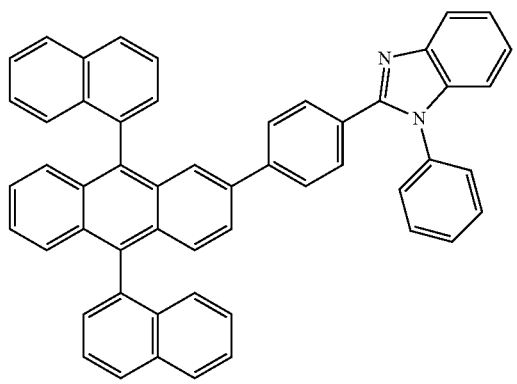
ET7
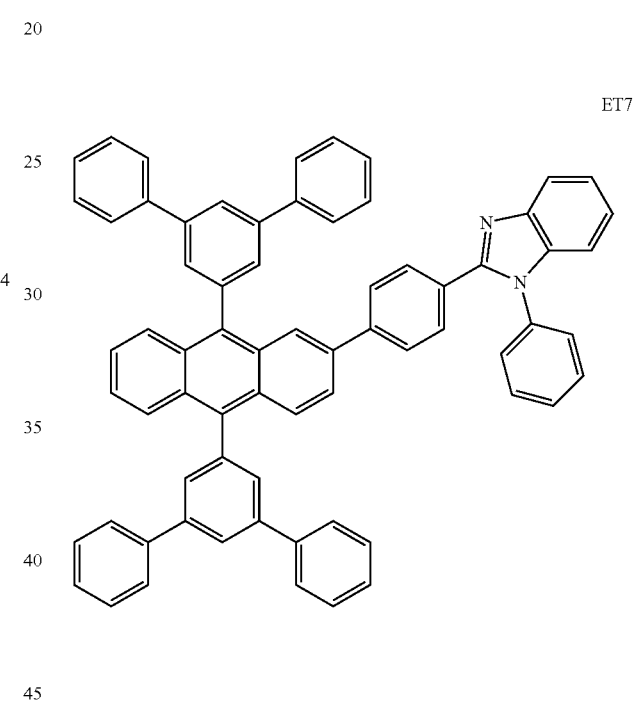
ET8
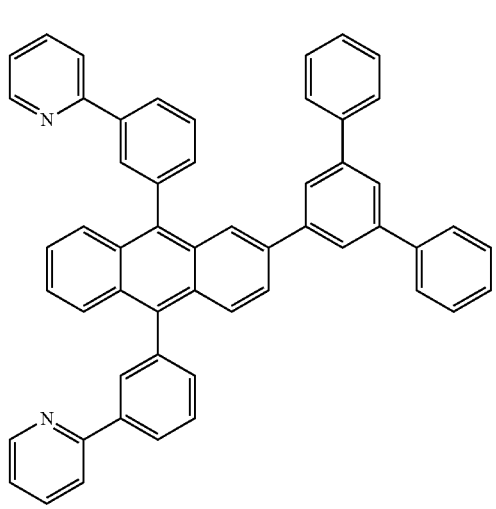

ET9
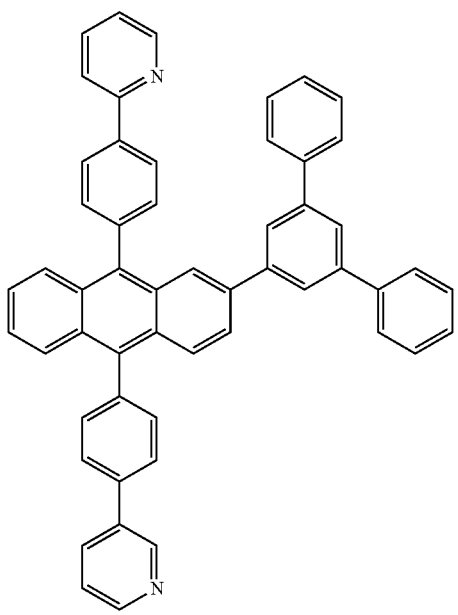
ET11
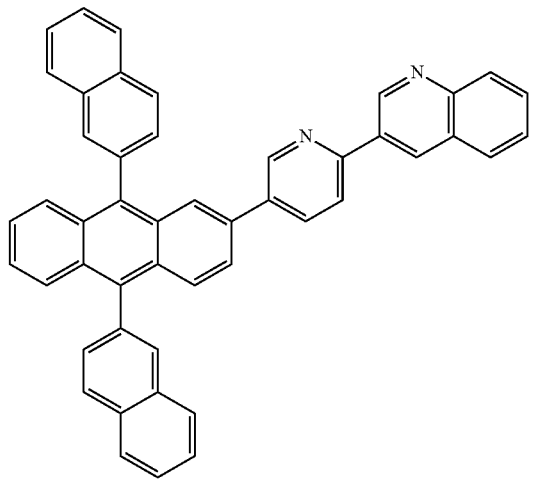
ET12
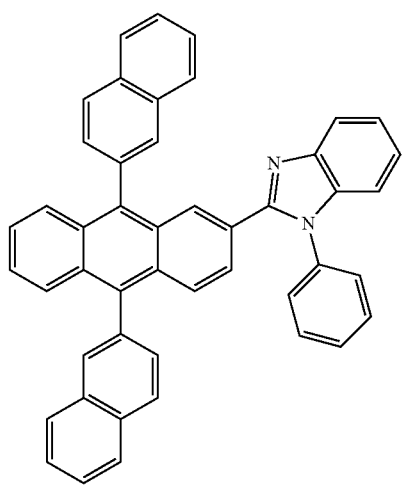
ET10
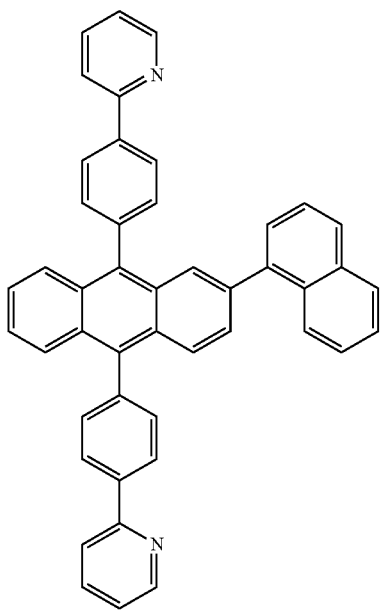
ET13
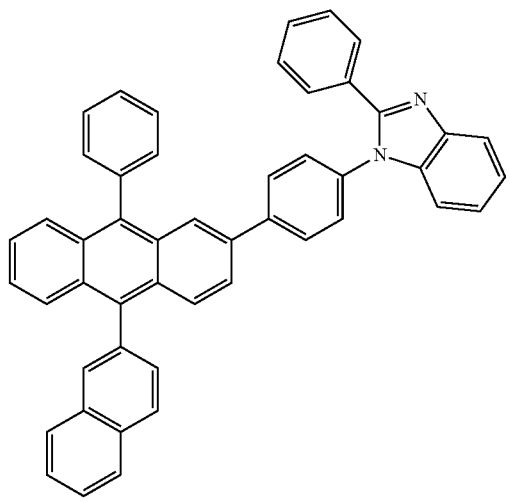

ET14
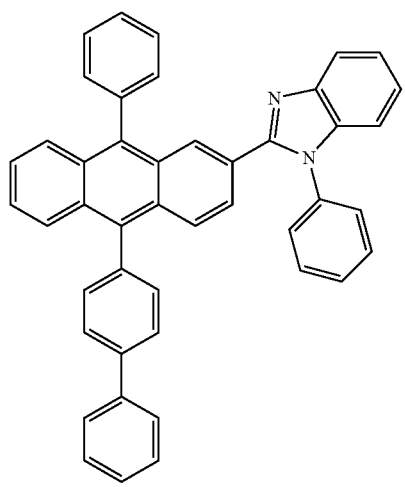
ET15
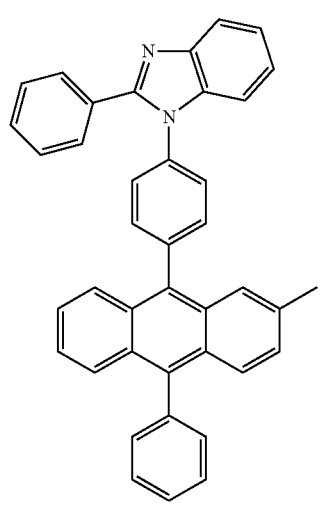
ET16
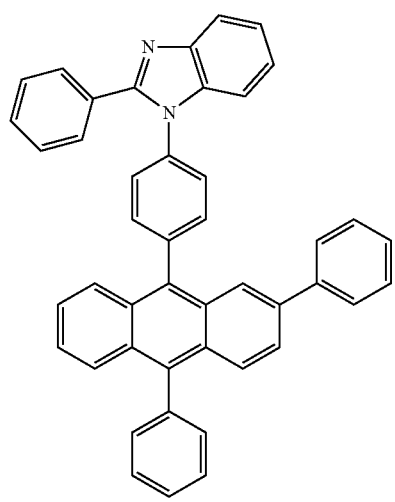
ET17
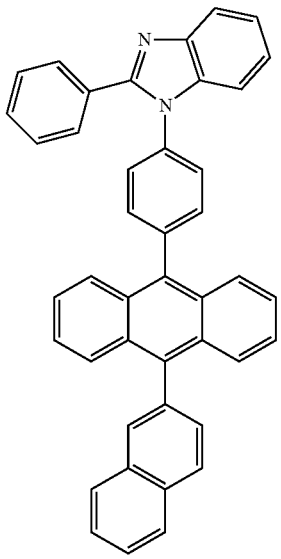
ET18
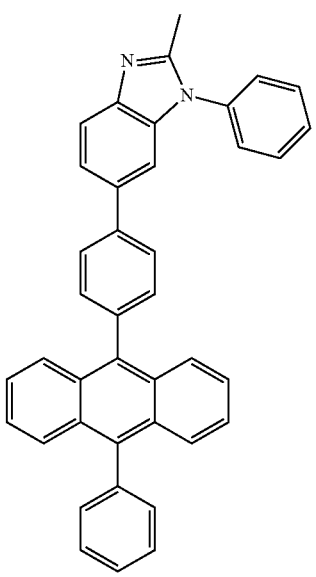
ET19

ET20
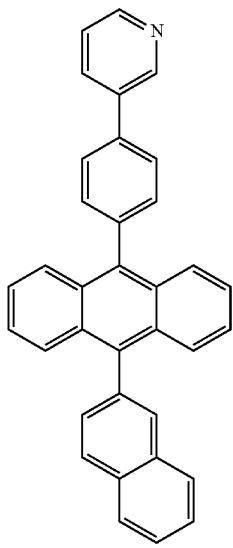
ET21
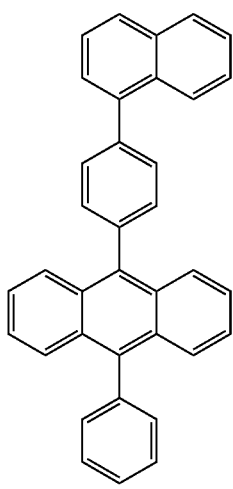
ET22
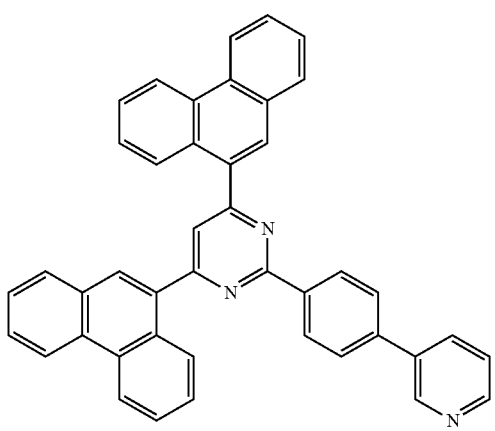
ET23
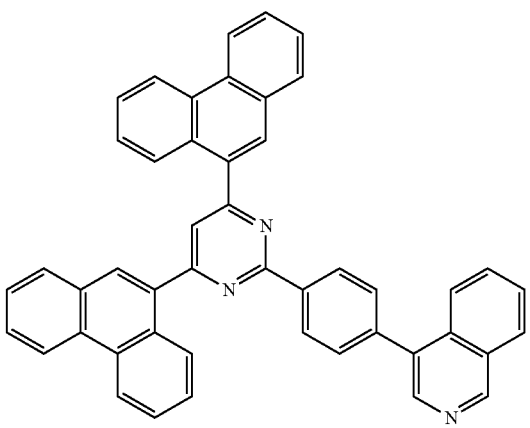
ET24
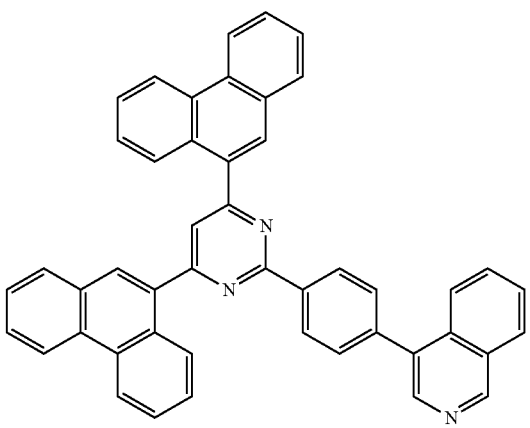
ET25
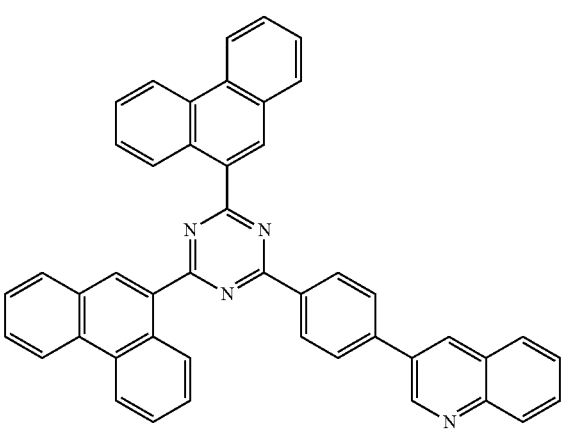

-continued
ET26
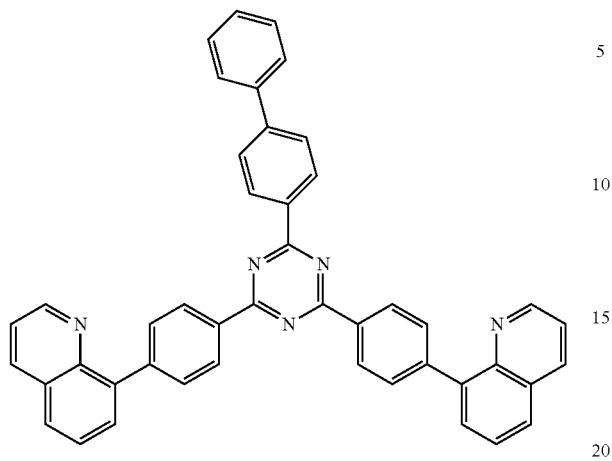
ET27
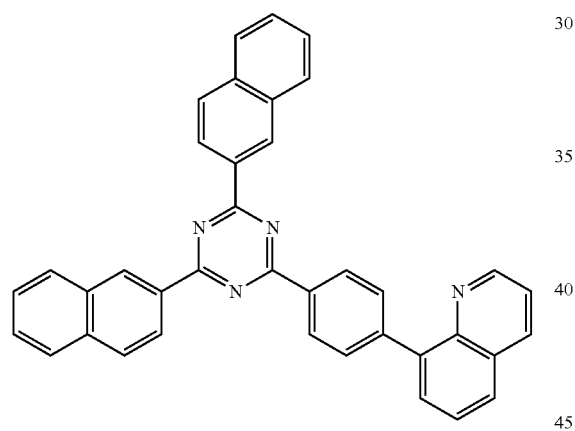
ET28
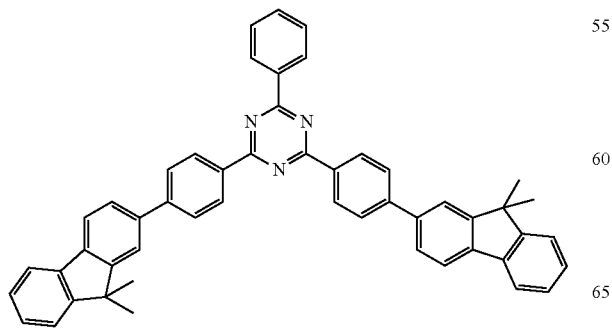
-continued
ET29
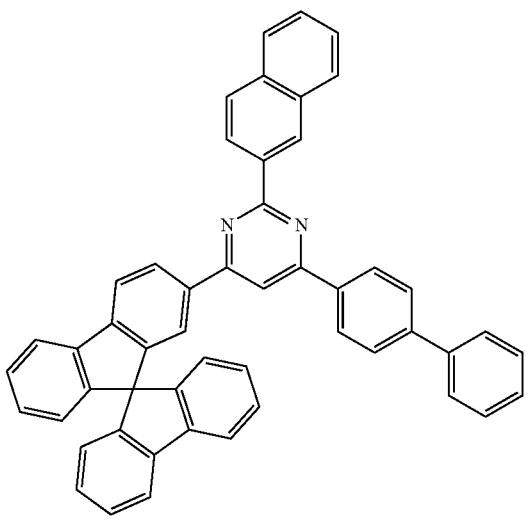
ET30
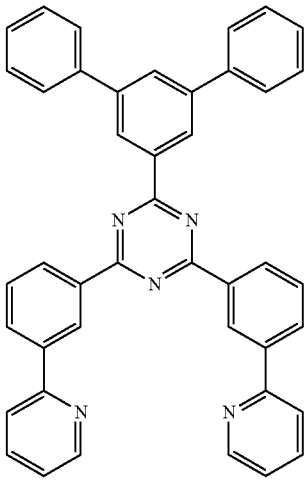
ET31
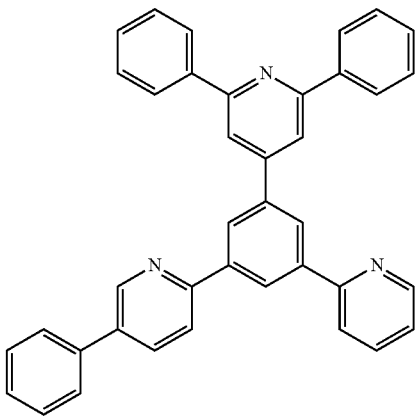

ET32
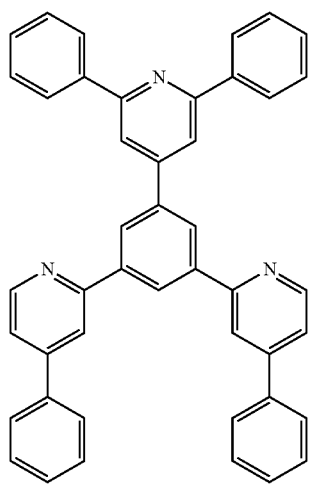
ET35
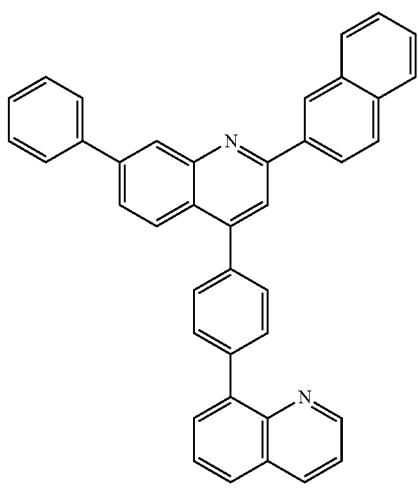
ET36
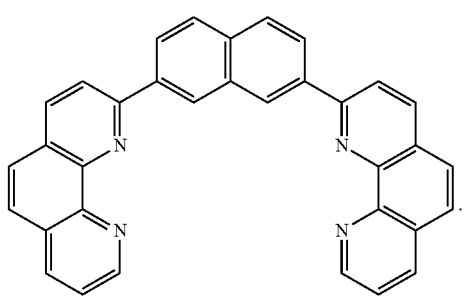
ET33
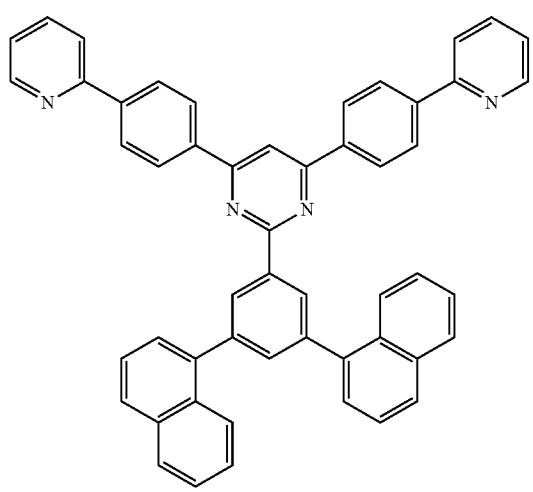
In various embodiments, the electron transport region may include at least one compound selected from BCP (2,9-dimethyl-4,7-diphenyl-1,10-phenanthroline), Bphen (4,7-diphenyl-1,10-phenanthroline), Alq$_3$, BAlq, TAZ (3-(biphenyl-4-yl)-5-(4-tert-butylphenyl)-4-phenyl-4H-1,2,4-triazole), and NTAZ.
Alq$_3$
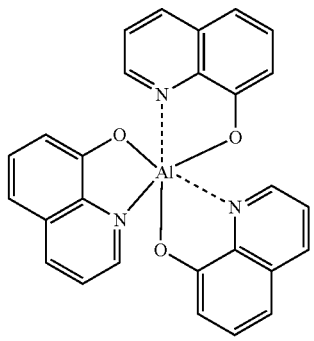
BAlq
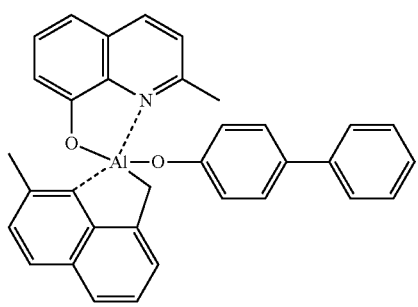
ET34
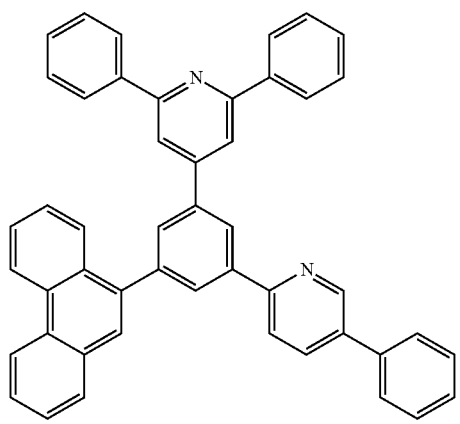

TAZ

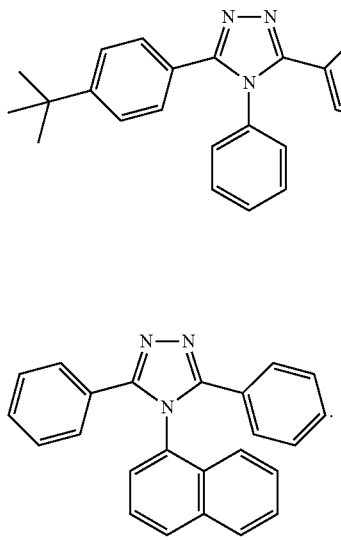

NTAZ

ET-D1

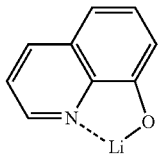

ET-D2

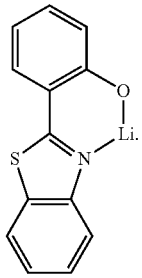

The thickness of the buffer layer, the hole blocking layer, and the electron control layer may each independently be in a range of about 20 Å to about 1,000 Å, for example, about 30 Å to about 300 Å. When the thicknesses of the buffer layer, the hole blocking layer, and/or the electron control layer are within any of these ranges, excellent (or suitable) hole blocking characteristics or electron control characteristics may be obtained without a substantial increase in driving voltage.

A thickness of the electron transport layer may be in a range of about 100 Å to about 1,000 Å, for example, about 150 Å to about 500 Å. When the thickness of the electron transport layer is within any of the ranges described above, the electron transport layer may have satisfactory (or suitable) electron transport characteristics without a substantial increase in driving voltage.

The electron transport region (e.g., the electron transport layer in the electron transport region) may further include, in addition to the materials described above, a metal-containing material.

The metal-containing material may include at least one selected from alkaline metal complex and alkaline earth-metal complex. The alkaline metal complex may include a metal ion selected from a Li ion, a Na ion, a K ion, a Rb ion, and a Cs ion; and the alkaline earth-metal complex may include a metal ion selected from a Be ion, a Mg ion, a Ca ion, a Sr ion, and a Ba ion. A ligand coordinated with the metal ion of the alkaline metal complex and the alkaline earth-metal complex may each independently be selected from a hydroxy-quinoline, a hydroxy-isoquinoline, a hydroxy-benzoquinoline, a hydroxy-acridine, a hydroxy-phenanthridine, a hydroxy-phenylan oxazole, a hydroxy-phenylthiazole, a hydroxy-diphenylan oxadiazole, a hydroxy-diphenylthiadiazole, a hydroxy-phenylpyridine, a hydroxy-phenylbenzoimidazole, a hydroxy-phenylbenzothiazole, a bipyridine, a phenanthroline, and a cyclopentadiene, but is not limited thereto.

For example, the metal-containing material may include a Li complex. The Li complex may include, for example, Compound ET-D1 (LiQ) and/or Compound ET-D2:

The electron transport region may include an electron injection layer that facilitates injection of electrons from the second electrode 190. The electron injection layer may directly contact the second electrode 190.

The electron injection layer may have i) a single-layered structure including a single layer including a single material, ii) a single-layered structure including a single layer including a plurality of different materials, or iii) a multi-layered structure having a plurality of layers including a plurality of different materials.

The electron injection layer may include alkaline metal, alkaline earth metal, rare-earth-metal, alkaline metal compound, alkaline earth-metal compound, rare-earth metal compound, alkaline metal complex, alkaline earth-metal complex, rare-earth metal complex or a combination thereof.

The alkaline metal may be selected from Li, Na, K, Rb, and Cs. In one embodiment, the alkaline metal may be Li, Na, or Cs. In various embodiments, the alkaline metal may be Li or Cs, but is not limited thereto.

The alkaline earth metal may be selected from Mg, Ca, Sr, and Ba.

The rare-earth metal may be selected from Sc, Y, Ce, Tb, Yb, and Gd.

The alkaline metal compound, the alkaline earth-metal compound, and the rare-earth metal compound may be selected from oxides and halides (e.g., fluorides, chlorides, bromides, and/or iodides) of the alkaline metal, the alkaline earth-metal and rare-earth metal, respectively.

The alkaline metal compound may be selected from alkaline metal oxides (such as $Li_2O$, $Cs_2O$, and/or $K_2O$), and alkaline metal halides (such as LiF, NaF, CsF, KF, LiI, NaI, CsI, and/or KI). In one embodiment, the alkaline metal compound may be selected from LiF, $Li_2O$, NaF, LiI, NaI, CsI, and KI, but is not limited thereto.

The alkaline earth-metal compound may be selected from alkaline earth-metal oxides (such as BaO, SrO, CaO, $Ba_xSr_{1-x}O$ (0<x<1), and/or $Ba_xCa_{1-x}O$ (0<x<1)). In one embodiment, the alkaline earth-metal compound may be selected from BaO, SrO, and CaO, but is not limited thereto.

The rare-earth metal compound may be selected from $YbF_3$, $ScF_3$, $ScO_3$, $Y_2O_3$, $Ce_2O_3$, $GdF_3$, and $TbF_3$. In one embodiment, the rare-earth metal compound may be selected from $YbF_3$, $ScF_3$, $TbF_3$, $YbI_3$, $ScI_3$, and $TbI_3$, but is not limited thereto.

The alkaline metal complex, the alkaline earth-metal complex, and the rare-earth metal complex may include ions of alkaline metal, alkaline earth-metal, and rare-earth metal, respectively, as described above; a ligand coordinated with a metal ion of the alkaline metal complex, the alkaline earth-metal complex, or the rare-earth metal complex may each independently be selected from a hydroxy-quinoline, a hydroxy-isoquinoline, a hydroxy-benzoquinoline, a hydroxy-acridine, a hydroxy-phenanthridine, a hydroxy-phenyl oxazole, a hydroxy-phenylthiazole, a hydroxy-diphenyl oxadiazole, a hydroxy-diphenylthiadiazole, a hydroxy-phenylpyridine, a hydroxy-phenylbenzoimidazole, a hydroxy-phenylbenzothiazole, a bipyridine, a phenanthroline, and a cyclopentadiene, but is not limited thereto.

The electron injection layer may include alkaline metal, alkaline earth metal, rare-earth-metal, alkaline metal compound, alkaline earth-metal compound, rare-earth metal compound, alkaline metal complex, alkaline earth-metal complex, rare-earth metal complex or a combination thereof, as described above. In various embodiments, the electron injection layer may further include an organic material. When the electron injection layer further includes an organic material, alkaline metal, alkaline earth metal, rare-earth-metal, alkaline metal compound, alkaline earth-metal compound, rare-earth metal compound, alkaline metal complex, alkaline earth-metal complex, rare-earth metal complex, or a combination thereof may be homogeneously or non-homogeneously dispersed in a matrix including the organic material.

A thickness of the electron injection layer may be in a range of about 1 Å to about 100 Å, for example, about 3 Å to about 90 Å. When the thickness of the electron injection layer is within any of the ranges described above, the electron injection layer may have satisfactory (or suitable) electron injection characteristics without a substantial increase in driving voltage.

Second Electrode 190

The second electrode 190 may be disposed (e.g., positioned) on the organic layer 150 having such the structure according to embodiments of the present disclosure. The second electrode 190 may be a cathode (that is an electron injection electrode), and in this regard, a material for forming the second electrode 190 may be a material having a low work function, for example, a metal, an alloy, an electrically conductive compound, or a mixture thereof.

The second electrode 190 may include at least one selected from lithium (Li), silver (Ag), magnesium (Mg), aluminum (Al), aluminum-lithium (Al—Li), calcium (Ca), magnesium-indium (Mg—In), magnesium-silver (Mg—Ag), ITO, and IZO, but is not limited thereto. The second electrode 190 may be a transmissive electrode, a semi-transmissive electrode, or a reflective electrode.

The second electrode 190 may have a single-layered structure, or a multi-layered structure including two or more layers.

Figure 3:
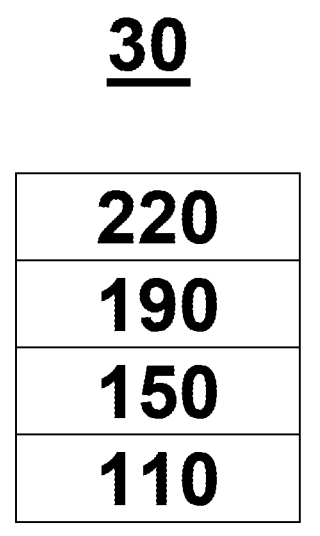
Figure 4:
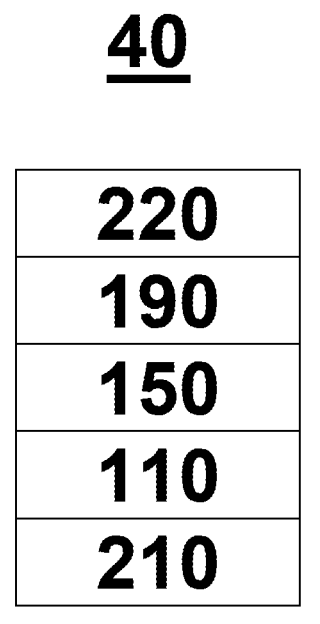

Description of FIGS. 2 to 4

Figure 2:
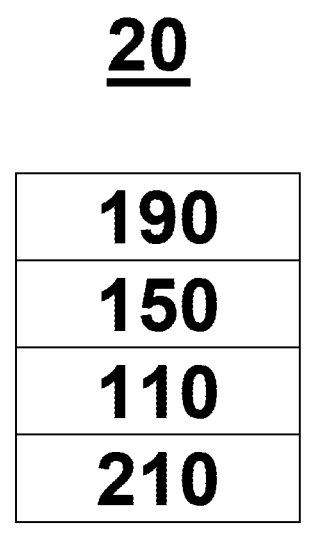

An organic light-emitting device 20 of FIG. 2 includes a first capping layer 210, a first electrode 110, an organic layer 150, and a second electrode 190 which are sequentially stacked in this stated order; an organic light-emitting device 30 of FIG. 3 includes a first electrode 110, an organic layer 150, a second electrode 190, and a second capping layer 220 which are sequentially stacked in this stated order; and an organic light-emitting device 40 of FIG. 4 includes a first capping layer 210, a first electrode 110, an organic layer 150, a second electrode 190, and a second capping layer 220 which are sequentially stacked in this stated order.

Regarding FIGS. 2 to 4, descriptions of the first electrode 110, the organic layer 150, and the second electrode 190 may be understood by referring to the descriptions thereof presented in connection with FIG. 1.

In the organic layer 150 of each of the organic light-emitting devices 20 and 40, light generated in an emission layer may pass through the first electrode 110 (which may be a semi-transmissive electrode or a transmissive electrode) and the first capping layer 210 toward the outside; and in the organic layer 150 of each of the organic light-emitting devices 30 and 40, light generated in an emission layer may pass through the second electrode 190 (which may be a semi-transmissive electrode or a transmissive electrode) and the second capping layer 220 toward the outside.

The first capping layer 210 and/or the second capping layer 220 may increase external luminescent efficiency according to the principle of constructive interference.

The first capping layer 210 and the second capping layer 220 may each independently be an organic capping layer including an organic material, an inorganic capping layer including an inorganic material, or a composite capping layer including an organic material and an inorganic material.

At least one selected from the first capping layer 210 and the second capping layer 220 may each independently include at least one material selected from carbocyclic compounds, heterocyclic compounds, amine-based compounds, porphine derivatives, phthalocyanine derivatives, naphthalocyanine derivatives, alkaline metal complexes, and alkaline earth metal-based complexes. The carbocyclic compound, the heterocyclic compound, and the amine-based compound may each independently be optionally substituted with a substituent containing at least one element selected from O, N, S, Se, Si, F, Cl, Br, and I. In various embodiments, at least one selected from the first capping layer 210 and the second capping layer 220 may each independently include an amine-based compound.

In various embodiments, at least one selected from the first capping layer 210 and the second capping layer 220 may each independently include the compound represented by Formula 201 or the compound represented by Formula 202.

In various embodiments, at least one selected from the first capping layer 210 and the second capping layer 220 may each independently include a compound selected from Compounds HT28 to HT33 and Compounds CP1 to CP5, but is not limited thereto:

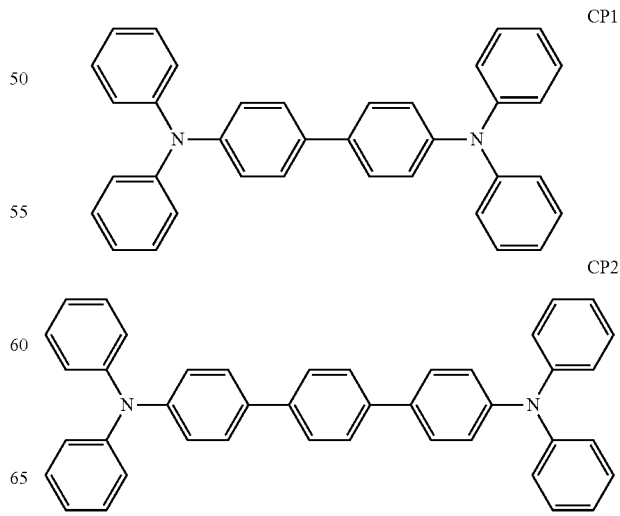

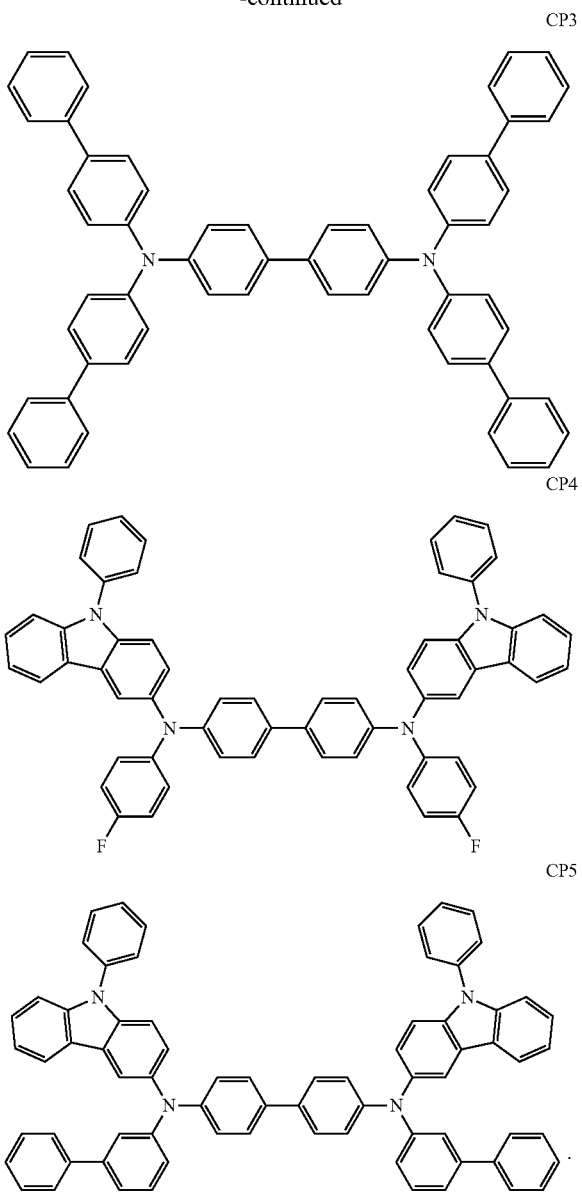

Hereinbefore, the organic light-emitting device according to an embodiment has been described in connection with FIGS. 1-4. However, embodiments of the present disclosure are not limited thereto.

Layers constituting the hole transport region, the emission layer, and layers constituting the electron transport region may each independently be formed by using one or more suitable methods such as vacuum deposition, spin coating, casting, a Langmuir-Blodgett (LB) method, ink-jet printing, laser-printing, and/or laser-induced thermal imaging.

When the respective layers of the hole transport region, the emission layer, and the respective layers of the electron transport region are formed by deposition, the deposition may be performed at a deposition temperature of about 100 to about 500° C., at a vacuum degree of about $10^{-8}$ to about $10^{-3}$ torr, and at a deposition rate of about 0.01 to about 100 Å/sec, by taking into account a compound for forming the layer to be deposited, and the structure of the layer to be formed.

When layers constituting the hole transport region, the emission layer, and layers constituting the electron transport region are formed by spin coating, the spin coating may be performed at a coating speed of about 2,000 rpm to about 5,000 rpm and at a heat treatment temperature of about 80° C. to 200° C., by taking into account a compound to be included in the to-be-formed layer, and the structure of the to-be-formed layer.

General Definition of Substituents

The term "$C_1$-$C_{60}$ alkyl group," as used herein, may refer to a linear or branched aliphatic saturated hydrocarbon monovalent group having 1 to 60 carbon atoms, and non-limiting examples thereof include a methyl group, an ethyl group, a propyl group, an isobutyl group, a sec-butyl group, a tert-butyl group, a pentyl group, an iso-amyl group, and a hexyl group. The term "$C_1$-$C_{60}$ alkylene group," as used herein, may refer to a divalent group having the same structure as the $C_1$-$C_{60}$ alkyl group.

The term "$C_2$-$C_{60}$ alkenyl group," as used herein, may refer to a hydrocarbon group having at least one carbon-carbon double bond at one or more positions along the hydrocarbon chain of the $C_2$-$C_{60}$ alkyl group (e.g., in the middle and/or at the terminus of the $C_2$-$C_{60}$ alkyl group), and non-limiting examples thereof include an ethenyl group, a propenyl group, and a butenyl group. The term "$C_2$-$C_{60}$ alkenylene group," as used herein, may refer to a divalent group having the same structure as the $C_2$-$C_{60}$ alkenyl group.

The term "$C_2$-$C_{60}$ alkynyl group," as used herein, may refer to a hydrocarbon group having at least one carbon-carbon triple bond at one or more positions along the hydrocarbon chain of the $C_2$-$C_{60}$ alkyl group (e.g., in the middle and/or at the terminus of the $C_2$-$C_{60}$ alkyl group), and non-limiting examples thereof include an ethynyl group and a propynyl group. The term "$C_2$-$C_{60}$ alkynylene group," as used herein, may refer to a divalent group having the same structure as the $C_2$-$C_{60}$ alkynyl group.

The term "$C_1$-$C_{60}$ alkoxy group," as used herein, may refer to a monovalent group represented by —$OA_{101}$ (wherein $A_{101}$ is the $C_1$-$C_{60}$ alkyl group), and non-limiting examples thereof include a methoxy group, an ethoxy group, and an isopropoxy group.

The term "$C_3$-$C_{10}$ cycloalkyl group," as used herein, may refer to a monovalent monocyclic saturated hydrocarbon group having 3 to 10 carbon atoms, and non-limiting examples thereof include a cyclopropyl group, a cyclobutyl group, a cyclopentyl group, a cyclohexyl group, and a cycloheptyl group. The term "$C_3$-$C_{10}$ cycloalkylene group," as used herein, may refer to a divalent group having the same structure as the $C_3$-$C_{10}$ cycloalkyl group.

The term "$C_1$-$C_{10}$ heterocycloalkyl group," as used herein, may refer to a monovalent saturated monocyclic group having at least one heteroatom selected from N, O, Si, P, and S as a ring-forming atom, and 1 to 10 carbon atoms, and non-limiting examples thereof include a tetrahydrofuranyl group and a tetrahydrothiophenyl group.

The term "$C_1$-$C_{10}$ heterocycloalkylene group," as used herein, may refer to a divalent group having the same structure as the $C_1$-$C_{10}$ heterocycloalkyl group.

The term "$C_3$-$C_{10}$ cycloalkenyl group," as used herein, may refer to a monovalent monocyclic group that has 3 to 10 carbon atoms and at least one double bond in the ring thereof and does not have aromaticity, and non-limiting examples thereof include a cyclopentenyl group, a cyclohexenyl group, and a cycloheptenyl group. The term "$C_3$-$C_{10}$ cycloalkenylene group," as used herein, may refer to a divalent group having the same structure as the $C_3$-$C_{10}$ cycloalkenyl group.

The term "$C_1$-$C_{10}$ heterocycloalkenyl group," as used herein, may refer to a monovalent monocyclic group that has at least one heteroatom selected from N, O, Si, P, and S as a ring-forming atom, 1 to 10 carbon atoms, and at least one double bond in its ring. Non-limiting examples of the $C_1$-$C_{10}$ heterocycloalkenyl group include a 4,5-dihydro-1,2,3,4-oxatriazolylgroup, a 2,3-dihydrofuranyl group, and a 2,3-dihydrothiophenyl group. The term "$C_1$-$C_{10}$ heterocycloalkenylene group," as used herein, may refer to a divalent group having the same structure as the $C_1$-$C_{10}$ heterocycloalkenyl group.

The term "$C_6$-$C_{60}$ aryl group," as used herein, may refer to a monovalent group having an aromatic carbocyclic system having 6 to 60 carbon atoms, and the term "$C_6$-$C_{60}$ arylene group," as used herein, may refer to a divalent group having an aromatic carbocyclic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each independently include two or more rings, the respective rings may be fused to each other.

The term "$C_1$-$C_{60}$ heteroaryl group," as used herein, may refer to a monovalent group having an aromatic heterocyclic system that has at least one heteroatom selected from N, O, Si, P, and S as a ring-forming atom, and 1 to 60 carbon atoms. The term "$C_1$-$C_{60}$ heteroarylene group," as used herein, may refer to a divalent group having an aromatic heterocyclic system that has at least one heteroatom selected from N, O, Si, P, and S as a ring-forming atom, and 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each independently include two or more rings, the respective rings may be fused to each other.

The term "$C_6$-$C_{60}$ aryloxy group," as used herein, may refer to a group represented by —$OA_{102}$ (wherein $A_{102}$ is the $C_6$-$C_{60}$ aryl group), and the term $C_6$-$C_{60}$ arylthio group used herein may refer to a group represented by —$SA_{103}$ (wherein $A_{103}$ is the $C_6$-$C_{60}$ aryl group).

The term "monovalent non-aromatic condensed polycyclic group," as used herein, may refer to a monovalent group that has two or more rings condensed (e.g., fused) with each other, only carbon atoms as ring-forming atoms (e.g., 8 to 60 carbon atoms), and non-aromaticity in the entire molecular structure (e.g., does not have overall aromaticity). A non-limiting example of the monovalent non-aromatic condensed polycyclic group is a fluorenyl group. The term "divalent non-aromatic condensed polycyclic group," used herein, may refer to a divalent group having the same structure as the monovalent non-aromatic condensed polycyclic group.

The term "monovalent non-aromatic condensed heteropolycyclic group," as used herein, may refer to a monovalent group that has two or more rings condensed (e.g., fused) to each other, has at least one heteroatom selected from N, O, Si, P, and S, other than carbon atoms (e.g., 1 to 60 carbon atoms), as a ring-forming atom, and has non-aromaticity in the entire molecular structure (e.g., does not have overall aromaticity). A non-limiting example of the monovalent non-aromatic condensed heteropolycyclic group is a carbazolyl group. The term "divalent non-aromatic condensed heteropolycyclic group," used herein, may refer to a divalent group having the same structure as the monovalent non-aromatic condensed heteropolycyclic group.

The term "$C_5$-$C_{60}$ carbocyclic group," as used herein, may refer to a monocyclic or polycyclic group having 5 to 60 carbon atoms in which only carbon atoms are ring-forming atoms. The term "$C_5$-$C_{60}$ carbocyclic group," as used herein may refer to an aromatic carbocyclic group or a non-aromatic carbocyclic group. The term "$C_5$-$C_{60}$ carbocyclic group," as used herein, may refer to a ring (such as a benzene ring), a monovalent group (such as a phenyl group), or a divalent group (such as a phenylene group). In various embodiments, depending on the number of substituents connected to the $C_5$-$C_{60}$ carbocyclic group, the $C_5$-$C_{60}$ carbocyclic group may be a trivalent group or a quadrivalent group.

The term "$C_1$-$C_{60}$ heterocyclic group," as used herein, may refer to a group having the same structure as the $C_1$-$C_{60}$ carbocyclic group, except that as a ring-form ing atom, at least one heteroatom selected from N, O, Si, P, and S is used, in addition to carbon atoms (e.g., the number of carbon atoms may be in a range of 1 to 60).

It will be understood that if a substituent that appears in the present disclosure is not expressly defined above, the definition of the substituent is consistent with a general definition thereof, unless stated otherwise.

At least one substituent of the substituted $C_5$-$C_{60}$ carbocyclic group, substituted $C_1$-$C_{60}$ heterocyclic group, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, a substituted divalent non-aromatic condensed polycyclic group, a substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from the group consisting of:

deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$) and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

The term "Ph", as used herein, may refer to a phenyl group; the term "Me", as used herein, may refer to a methyl group; the term "Et", as used herein, may refer to an ethyl group; the terms "ter-Bu" or "But", as used herein, may refer to a tert-butyl group; the term "OMe," as used herein may refer to a methoxy group, and "D" as used herein may refer to deuterium.

The term "biphenyl group" used therein may refer to a monovalent group having two benzene rings linked to each other via a single bond. For example, "biphenyl group" may refer to "a phenyl group substituted with a phenyl group." The "biphenyl group" may be "a substituted phenyl group" having "a $C_6$-$C_{60}$ aryl group" as a substituent.

The "terphenyl group" used herein may refer to a monovalent group having three benzene rings in which adjacent benzenes are linked to each other via a single bond. For example, "terphenyl group" may refer to "a phenyl group substituted with a biphenyl group." The "terphenyl group" may be "a substituted phenyl group" having "a $C_6$-$C_{60}$ aryl group substituted with a $C_6$-$C_{60}$ aryl group" as a substituent.

* and *' used herein, unless defined otherwise, each independently refer to a binding site to a neighboring atom in a corresponding formula.

Hereinafter, a compound according to embodiments of the present disclosure and an organic light-emitting device according to embodiments will be described in more detail with reference to Synthesis Examples and Examples. However, these examples are provided for illustrative purposes only, and should not in any sense be interpreted as limiting the scope of the present disclosure. The expression "B was used instead of A" used in describing Synthesis Examples may refer to a molar equivalent of A being identical (or substantially identical) to a molar equivalent of B.

EXAMPLES

Synthesis Example 1: Synthesis of Compound 1

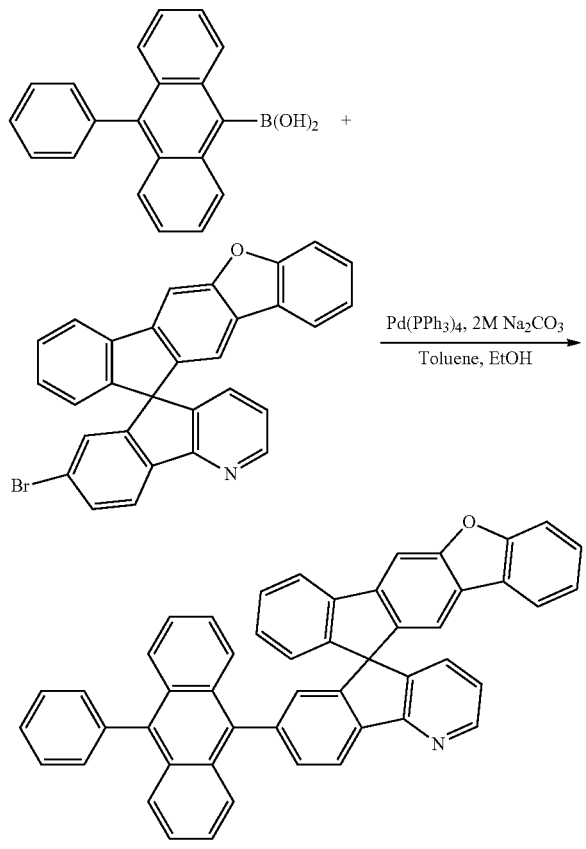

Compound 1

0.63 g (1 equivalent (eq), 1.30 mmol) of 7'-bromospiro[fluoreno[3,2-b]benzofuran-11,5'-indeno[1,2-c]pyridine], 0.43 g (1.1 eq, 1.43 mmol) of (10-phenylanthracen-9-yl) boronic acid, and 0.06 g (0.04 eq, 0.052 mmol) of tetrakis(triphenylphosphine)palladium(0) were added to a flask. The obtained mixed solution was vacuum dried, and then, the flask was filled with a nitrogen gas. 13 ml of toluene was added to the flask to dissolve the starting materials. Then, 6.5 ml of ethanol, 2.0 M of sodium carbonate, and 6.5 ml (10 eq, 13.0 mmol) of water were added thereto. The resulting mixed solution was stirred under reflux at a temperature of 80° C. for 3 hours. After the reaction was completed, a washing process was performed thereon using distilled water, and an organic layer was extracted therefrom using ethyl acetate. The resulting solution was dried using magnesium sulfate, and the residual was filtered using Celite. The resulting product was purified by column chromatography, thereby completing the preparation of Compound 1 (0.67 g of 7'-(10-phenylanthracen-9-yl)spiro[fluoreno[3,2-b]benzofuran-11,5'-indeno[1,2-c]pyridine]) (yield=75%).

¹H NMR: 9.24 (1H), 8.06 (2H), 7.91 (6H), 7.73 (3H), 7.51 (5H), 7.40 (6H), 7.35 (3H), 7.24 (1H), 7.03 (2H). APCI-MS (m/z): 659 [M⁺]

Synthesis Example 2: Synthesis of Compound 2

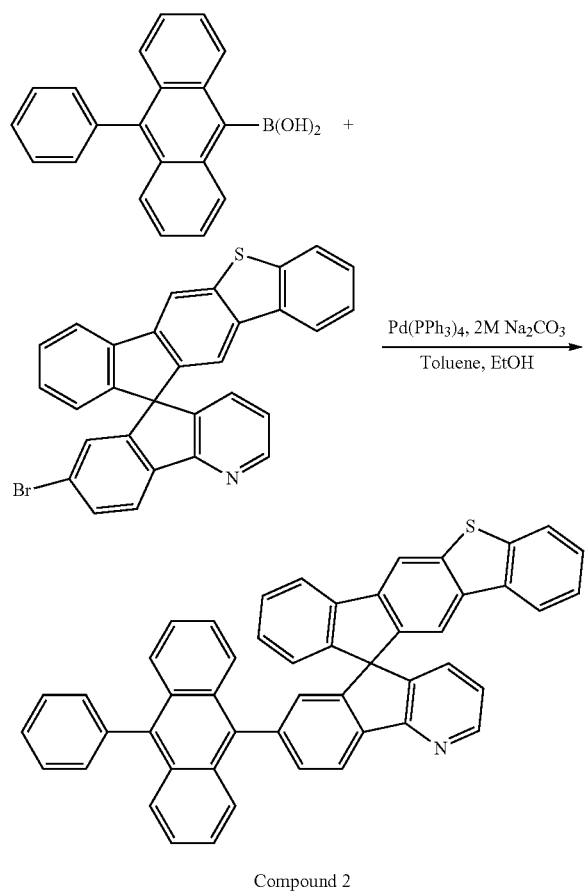

Compound 2

0.65 g (yield=70%) of Compound 2 (7'-(10-phenylanthracen-9-yl)spiro[benzo[b]fluoreno[2,3-d]thiophene-11,5'-indeno[1,2-c]pyridine]) was prepared in the same (or substantially the same) manner as in Synthesis Example 1, except that 7'-bromospiro[benzo[b]fluoreno[2,3-d]thiophene-11,5'-indeno[1,2-c]pyridine] was used instead of 7'-bromospiro[fluoreno[3,2-b]benzofuran-11,5'-indeno[1,2-c]pyridine].

¹H NMR: 9.24 (1H), 8.45 (1H), 7.98 (2H), 9.91 (4H), 7.85 (1H), 7.73 (1H), 7.67 (1H), 7.51 (6H), 7.40 (5H), 7.24 (1H), 7.06 (2H). APCI-MS (m/z): 675 [M⁺]

Synthesis Example 3: Synthesis of Compound 7

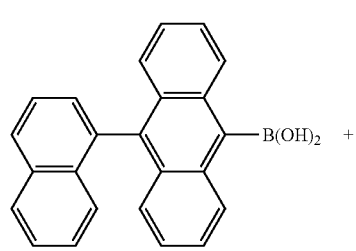

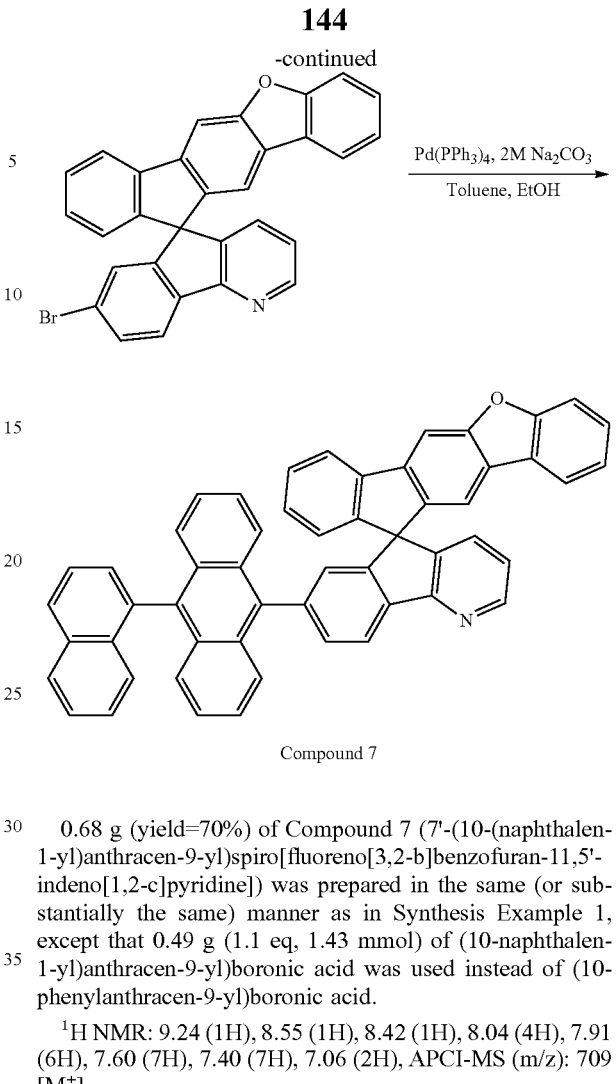

Compound 7

0.68 g (yield=70%) of Compound 7 (7'-(10-(naphthalen-1-yl)anthracen-9-yl)spiro[fluoreno[3,2-b]benzofuran-11,5'-indeno[1,2-c]pyridine]) was prepared in the same (or substantially the same) manner as in Synthesis Example 1, except that 0.49 g (1.1 eq, 1.43 mmol) of (10-naphthalen-1-yl)anthracen-9-yl)boronic acid was used instead of (10-phenylanthracen-9-yl)boronic acid.

¹H NMR: 9.24 (1H), 8.55 (1H), 8.42 (1H), 8.04 (4H), 7.91 (6H), 7.60 (7H), 7.40 (7H), 7.06 (2H), APCI-MS (m/z): 709 [M⁺]

Synthesis Example 4: Synthesis of Compound 8

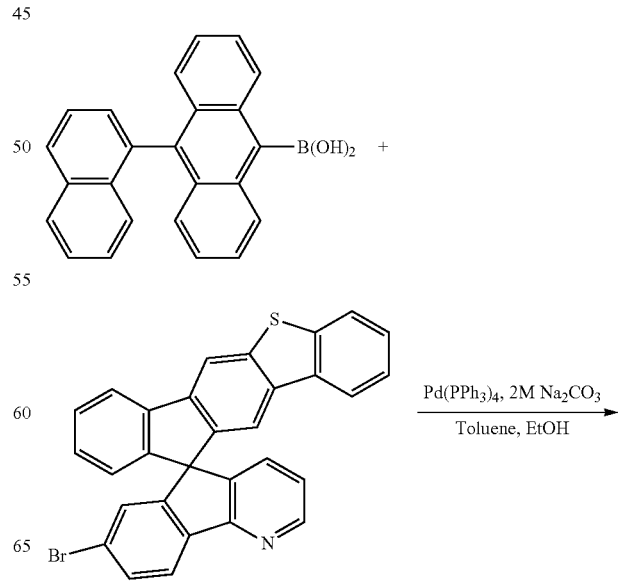

-continued

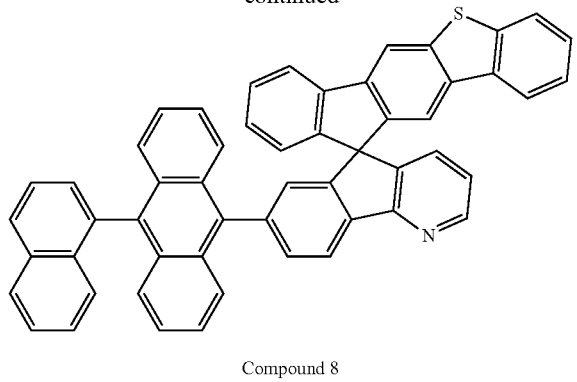

Compound 8

0.70 g (yield=70%) of Compound 8 (7'-(10-(naphthalen-1-yl)anthracen-9-yl)spiro[benzo[b]fluoreno[2,3-d]thiophene-11,5'-indeno[1,2-c]pyridine]) was prepared in the same (or substantially the same) manner as in Synthesis Example 2, except that 0.49 g (1.1 eq, 1.43 mmol) of (10-naphthalene-1-yl)anthracen-9-yl)boronic acid was used instead of (10-phenylanthracen-9-yl)boronic acid.

$^1$H NMR: 9.24 (1H), 8.55 (1H), 8.42 (2H), 8.04 (4H), 7.91 (7H), 7.73 (3H), 7.60 (5H), 7.40 (5H), 7.06 (2H), APCI-MS (m/z): 725 [M$^+$]

Example 1

As a substrate and an anode, a Corning 150/cm$^2$ (1,200 Å) ITO glass substrate was cut to a size of 50 mm×50 mm×0.7 mm, and then, sonicated with isopropyl alcohol and pure water, each for 5 minutes, and then washed by irradiation of ultraviolet ray for 30 minutes and ozone, and the resultant glass substrate was placed in a vacuum deposition apparatus.

2-TNATA was vacuum-deposited on the ITO anode to form a hole injection layer having a thickness of 600 Å, and 4,4'-bis[N-(1-naphthyl)-N-phenylamino]biphenyl (NPB) was vacuum-deposited on the hole injection layer to form a hole transport layer having a thickness of 300 Å.

Compound 1 (as a host) and Compound 107 (as a dopant) were co-deposited on the hole transport layer at a weight ratio of 97:3 to form an emission layer having a thickness of 20 nm.

Compound ET1 was deposited on the emission layer to form an electron transport layer having a thickness of 300 Å, LiF was deposited on the electron transport layer to form an electron injection layer having a thickness of 10 Å, and Al was vacuum-deposited on the electron injection layer to form a cathode having a thickness of 3,000 Å, thereby completing the manufacture of an organic light-emitting device.

Examples 2 to 6 and Comparative Examples 1 to 4

Organic light-emitting devices were manufactured in the same (or substantially the same) manner in Example 1, except that compounds as shown in Table 1 were respectively used as a host and a dopant in forming an emission layer, instead of Compound 1 and/or Compound 107.

Evaluation Example 1

The driving voltage, current density, luminance, and efficiency of the organic light-emitting devices of Examples 1 to 6 and Comparative Examples 1 to 4 were evaluated by using Keithley SMU 236 meter and a PR650 luminance measuring meter. Results thereof are shown in Table 1.

TABLE 1

| | Host | Dopant | Weight ratio of host to dopant | Driving voltage (V) | Current Density (mA/cm$^2$) | Brightness (cd/m$^2$) | Efficiency (cd/A) |
|---|---|---|---|---|---|---|---|
| Example 1 | Compound 1 | Compound 107 | 97:3 | 3.5 | 10 | 537 | 5.37 |
| Example 2 | Compound 2 | Compound 107 | 97:3 | 3.6 | 10 | 512 | 5.12 |
| Example 3 | Compound 7 | Compound 107 | 97:3 | 3.5 | 10 | 509 | 5.09 |
| Example 4 | Compound 8 | Compound 107 | 97:3 | 3.7 | 10 | 485 | 4.85 |
| Example 5 | Compound 1 | Compound 110 | 97:3 | 3.4 | 10 | 515 | 5.15 |
| Example 6 | Compound 1 | Compound 112 | 97:3 | 3.5 | 10 | 490 | 4.90 |
| Comparative Example 1 | Compound A | DPAVBi | 95:5 | 4.6 | 10 | 311 | 3.11 |
| Comparative Example 2 | Compound B | DPAVBi | 95:5 | 4.3 | 10 | 367 | 3.67 |
| Comparative Example 3 | Compound C | DPAVBi | 95:5 | 4.2 | 10 | 416 | 4.16 |
| Comparative Example 4 | Compound D | DPAVBi | 95:5 | 3.8 | 10 | 256 | 2.56 |

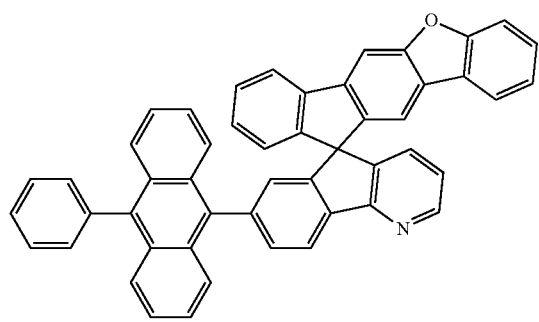
1
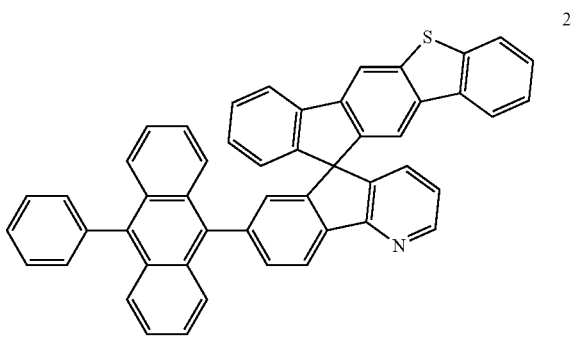
2
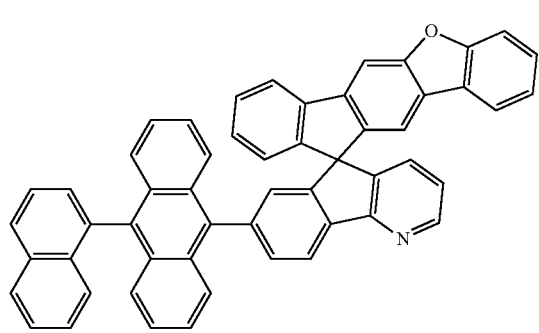
7
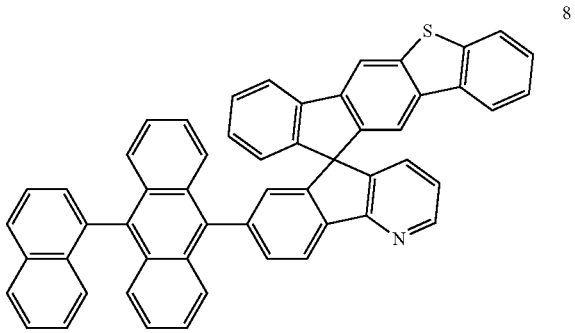
8
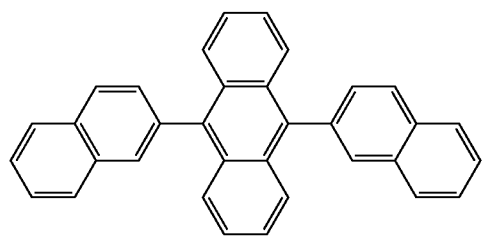
Compound A
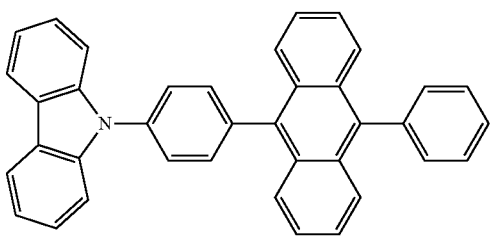
Compound B
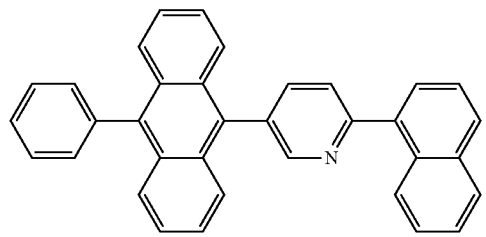
Compound C
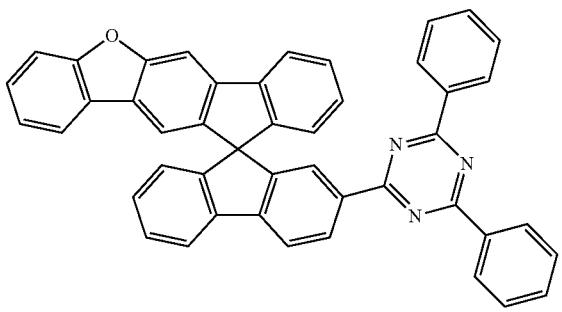
Compound D
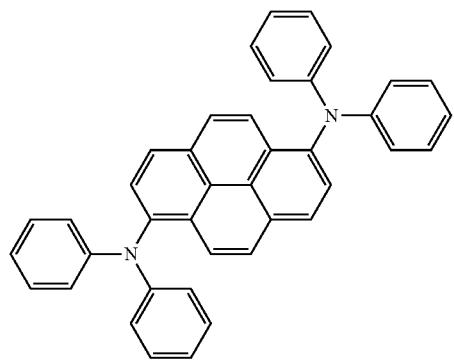
107
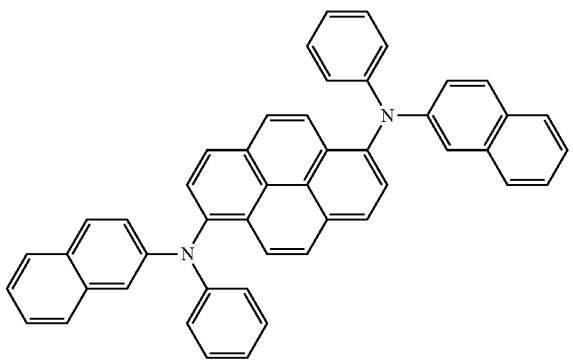
110

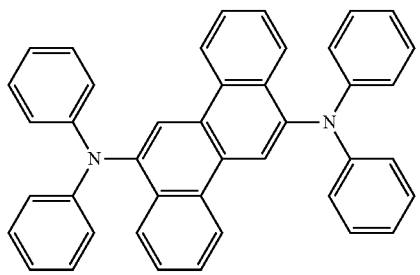

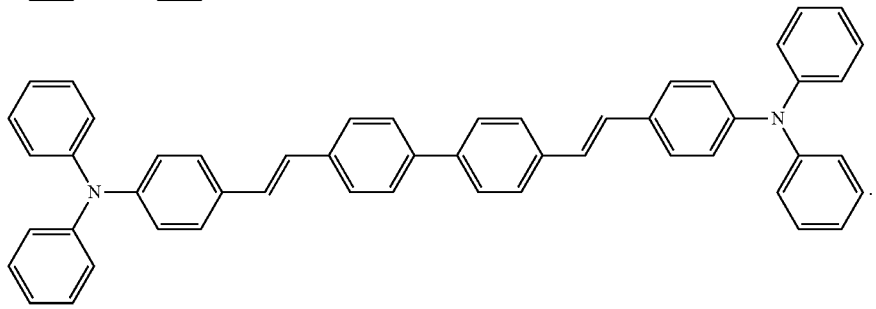

DPAVBi

Referring to the results shown in Table 1, it can be seen that the organic light-emitting devices of Examples 1 to 6 had low driving voltage, high luminance, and high efficiency, compared to those of the organic light-emitting devices of Comparative Examples 1 to 4.

According to embodiments of the present disclosure, an organic light-emitting device including the first compound and the second compound may have low driving voltage, high efficiency, and high luminance.

As used herein, the terms "use," "using," and "used" may be considered synonymous with the terms "utilize," "utilizing," and "utilized," respectively.

In addition, the terms "substantially," "about," and similar terms are used as terms of approximation and not as terms of degree, and are intended to account for the inherent deviations in measured or calculated values that would be recognized by those of ordinary skill in the art.

It will be understood that when an element such as a layer, film, region, or substrate is referred to as being "on" another element, it can be directly on the other element or intervening elements may also be present. In contrast, when an element is referred to as being "directly on" or "directly contacting" another element, there are no intervening elements present.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present disclosure as defined by the following claims and equivalents thereof.

What is claimed is:

1. An organic light-emitting device comprising:

a first electrode;

a second electrode facing the first electrode; and an organic layer between the first electrode and the second electrode, the organic layer comprising an emission layer, wherein the organic layer comprises a first compound represented by one selected from Formulae 1-1 to 1-7, and a second compound represented by Formula 501:

Formula 1-1

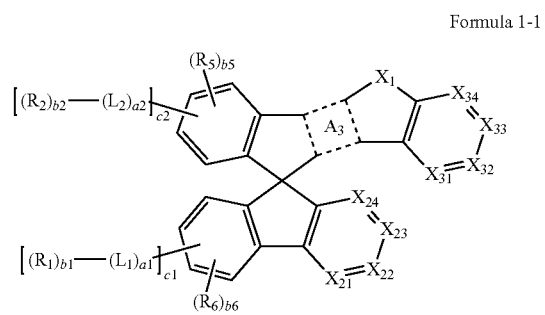

-continued

Formula 1-2
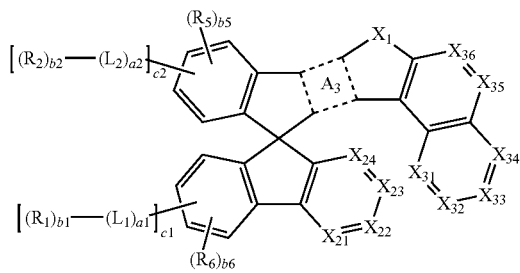

Formula 1-3
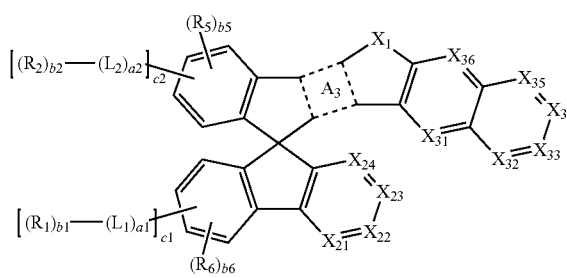

Formula 1-4
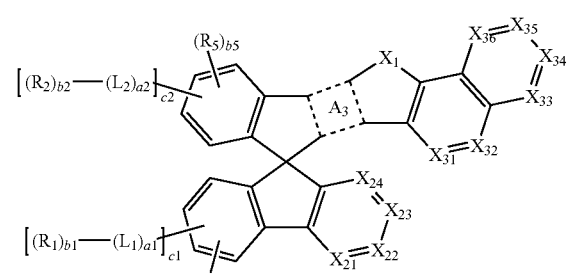

Formula 1-5
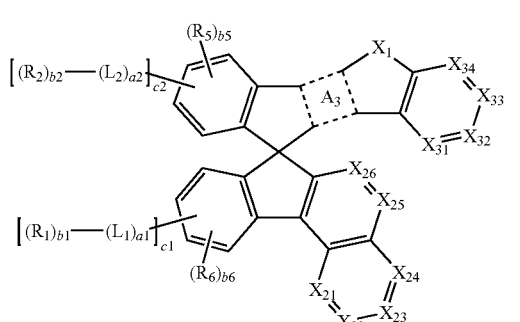

Formula 1-6
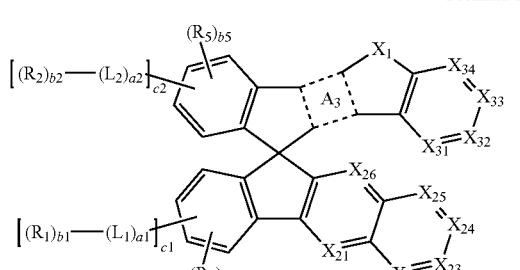

Formula 1-7
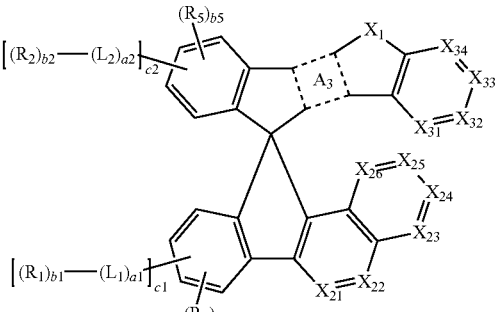

Formula 2A

Formula 2B

Formula 501
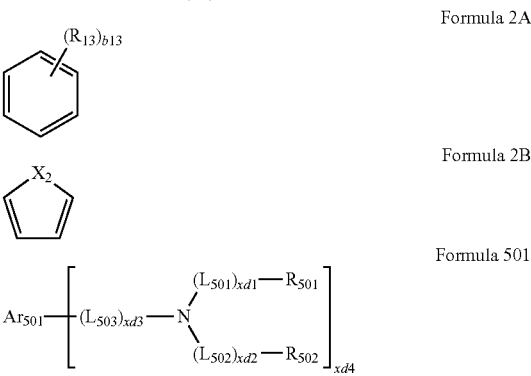

wherein, in Formulae 1-1 to 1-7, 2A, 2B, and 501,
ring $A_3$ is a group represented by Formula 2A or a group represented by Formula 2B,
$X_1$ is N-[$(L_{11})_{a11}$-$(R_{11})_{b11}$], O, or S,
$X_2$ is N-[$(L_{12})_{a12}$-$(R_{12})_{b12}$], O, or S,
$X_{21}$ is N or C($R_{21}$); $X_{22}$ is N or C($R_{22}$); $X_{23}$ is N or C($R_{23}$); $X_{24}$ is N or C($R_{24}$); $X_{25}$ is N or C($R_{25}$); $X_{26}$ is N or C($R_{26}$); $X_{31}$ is N or C($R_{31}$); $X_{32}$ is N or C($R_{32}$); $X_{33}$ is N or C($R_{33}$); $X_{34}$ is N or C($R_{34}$); $X_{35}$ is N or C($R_{35}$); and $X_{36}$ is N or C($R_{36}$),
provided that at least one of $X_{31}$ to $X_{34}$ in Formula 1-1 is N, and when at least one of $L_1$ and $L_2$ in Formulae 1-5, 1-6 and 1-7 is a substituted or unsubstituted anthracenylene group, at least one of $X_{25}$, $X_{26}$ and $X_{31}$ to $X_{34}$ in Formula 1-5 is N, at least one of $X_{21}$, $X_{26}$ and $X_{31}$ to $X_{34}$ in Formula 1-6 is N, and at least one of $X_{21}$, $X_{22}$ and $X_{31}$ to $X_{34}$ in Formula 1-7 is N,
$Ar_{501}$ is selected from a substituted or unsubstituted $C_5$-$C_{30}$ carbocyclic group and a substituted or unsubstituted $C_2$-$C_{30}$ heterocyclic group,
provided that $Ar_{501}$ is not a pyrene group, and
provided that when $Ar_{501}$ is at least one selected from a fluorene group, a spiro-bifluorene group, a benzofluorene group, a dibenzofluorene group, a phenanthrene group, an anthracene group, a fluoranthene group, a chrysene group, a naphthacene group, and a coronene group, then at least two selected from among $R_{501}$ and $R_{502}$ are substituted with —F,
$L_1$ and $L_2$ are each independently a substituted or unsubstituted condensed polycyclic group having three or more carbocyclic groups condensed with each other,
a1 and a2 are each independently an integer selected from 1 to 5, wherein when a1 is two or more, two or more $L_1$(s) are identical to or different from each other; and when a2 is two or more, two or more $L_2$(s) are identical to or different from each other, $L_{11}$, $L_{12}$ and $L_{501}$ to $L_{503}$ are each independently selected from a substituted or unsubstituted $C_3$-$C_{10}$ cycloalkylene group, a substituted or unsubstituted $C_1$-$C_{60}$ heterocycloalkylene group, a substituted or unsubstituted $C_3$-$C_{10}$ cycloalkenylene group, a substituted or unsubstituted $C_1$-$C_{60}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a11, a12, and xd1 to xd3 are each independently an integer selected from 0 to 5, wherein when a11 is two or more, two or more $L_{11}$(s) are identical to or different from each other; when a12 is two or more, two or more $L_{12}$(s) are identical to or different from each other; when xd1 is two or more, two or more $L_{501}$(s) are identical to or different from each other; when xd2 is two or more, two or more $L_{502}$(s) are identical to or different from each other; and when xd3 is two or more, two or more $L_{503}$(s) are identical to or different from each other, $R_1$ and $R_2$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, and a hydrazono group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, a benzofuranyl group, a benzothiophenyl group, a dibenzofuranyl group, a dibenzothiophenyl group, a benzocarbazolyl group, a dibenzocarbazolyl group a dibenzosilolyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, a benzofuranyl group, a benzothiophenyl group, a dibenzofuranyl group, a dibenzothiophenyl group, a benzocarbazolyl group, a dibenzocarbazolyl group, a dibenzosilolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, a benzofuranyl group, a benzothiophenyl group, a dibenzofuranyl group, a dibenzothiophenyl group, a benzocarbazolyl group, a dibenzocarbazolyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ are each independently selected from a $C_1$-$C_{10}$ alkyl group, a $C_1$-$C_{10}$ alkoxy group, a phenyl group, and a naphthyl group, $R_5$, $R_6$, $R_{11}$ to $R_{13}$, $R_{21}$ to $R_{26}$, $R_{31}$ to $R_{36}$, $R_{501}$, and $R_{502}$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), provided that in Formula 1-1, $R_{31}$ to $R_{34}$ are each hydrogen, b1, b2, b6, b11, and b12 are each independently an integer selected from 0 to 4, b5 is 0, b13 is 0, 1, or 2, c1 is an integer selected from 1 to 4, and c2 is 0, xd4 is an integer selected from 1 to 6, and at least one substituent of the substituted condensed polycyclic group having three or more carbocyclic groups condensed with each other, the substituted $C_5$-$C_{30}$ carbocyclic group, the substituted $C_2$-$C_{30}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from the group consisting of:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=Q)($Q_{31}$), —S(=Q)$_2$($Q_{31}$), and —P(=Q)($Q_{31}$)($Q_{32}$), wherein $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group, wherein at least one substituent of the substituted anthracenylene group is selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$) (wherein $Q_{31}$ to $Q_{33}$ are each independently selected from a $C_1$-$C_{10}$ alkyl group, a $C_1$-$C_{10}$ alkoxy group, a phenyl group, and a naphthyl group).

2. The organic light-emitting device of claim 1, wherein $X_1$ is O or S.

3. The organic light-emitting device of claim 1, wherein $Ar_{501}$ is selected from the group consisting of:

an indacene group, an acenaphthalene group, a fluorene group, a spiro-bifluorene group, a benzofluorene group, a dibenzofluorene group, a phenalene group, a phenanthrene group, an anthracene group, a fluoranthene group, a triphenylene group, a chrysene group, a naphthacene group, a picene group, a perylene group, a pentaphene group, a hexacene group, a pentacene group, a rubicene group, a coronene group, an ovalene group, a benzopyrene group, a benzochrysene group, a benzotriphenylene group, and a phenanthroline group; and an indacene group, an acenaphthalene group, a fluorene group, a spiro-bifluorene group, a benzofluorene group, a dibenzofluorene group, a phenalene group, a phenanthrene group, an anthracene group, a fluoranthene group, a triphenylene group, a chrysene group, a naphthacene group, a picene group, a perylene group, a pentaphene group, a hexacene group, a pentacene group, a rubicene group, a coronene group, an ovalene group, a benzopyrene group, a benzochrysene group, a benzotriphenylene group, and a phenanthroline group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$), wherein $Q_{31}$ to $Q_{33}$ are each independently selected from a $C_1$-$C_{10}$ alkyl group, a $C_1$-$C_{10}$ alkoxy group, a phenyl group, and a naphthyl group, provided that $Ar_{501}$ is not a pyrene group, and provided that when $Ar_{501}$ is at least one selected from a fluorene group, a spiro-bifluorene group, a benzofluorene group, a dibenzofluorene group, a phenanthrene group, an anthracene group, a fluoranthene group, a chrysene group, a naphthacene group, and a coronene group, then at least two selected from among $R_{501}$ and $R_{502}$ are substituted with —F.

4. The organic light-emitting device of claim 1, wherein $L_1$ and $L_2$ are each independently selected from the group consisting of:

an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, and an ovalenylene group; and an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, and an ovalenylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$), wherein $Q_{31}$ to $Q_{33}$ are each independently selected from a $C_1$-$C_{10}$ alkyl group, a $C_1$-$C_{10}$ alkoxy group, a phenyl group, and a naphthyl group.

5. The organic light-emitting device of claim 1, wherein $L_1$ and $L_2$ are each independently selected from groups represented by Formulae 3-8, 3-9, 3-25, and 3-35 to 3-41, and $L_{11}$, $L_{12}$, and $L_{501}$ to $L_{503}$ are each independently selected from groups represented by Formulae 3-1 to 3-41:

Formula 3-1

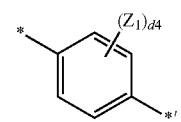

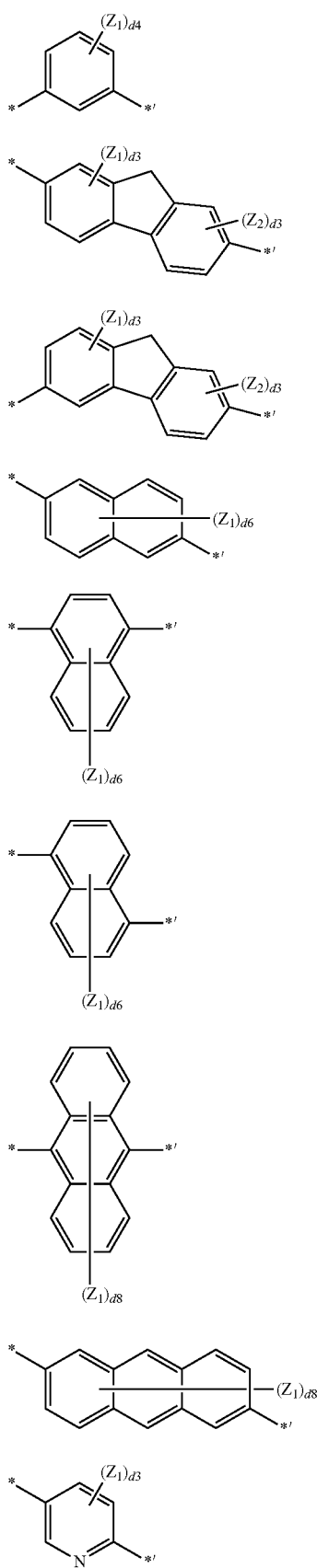
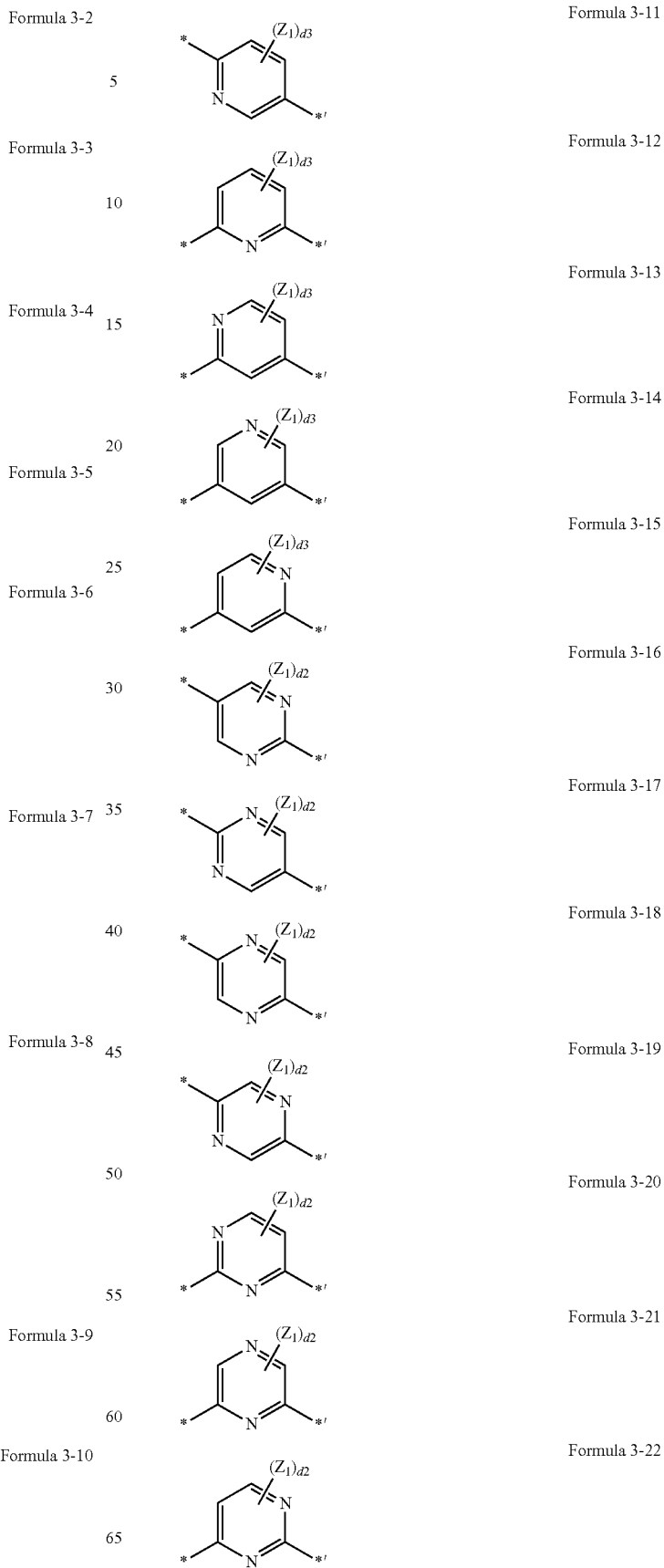

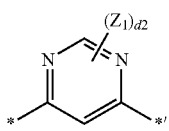 Formula 3-23
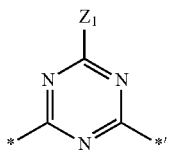 Formula 3-24
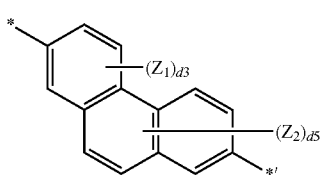 Formula 3-25
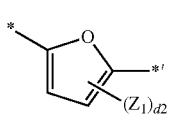 Formula 3-26
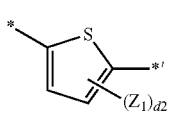 Formula 3-27
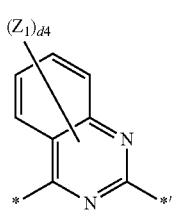 Formula 3-28
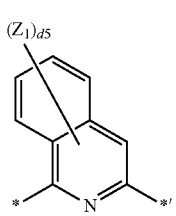 Formula 3-29
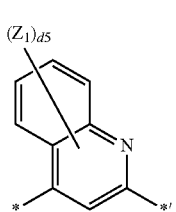 Formula 3-30
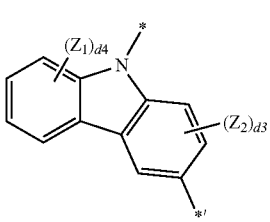 Formula 3-31
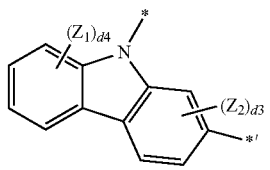 Formula 3-32
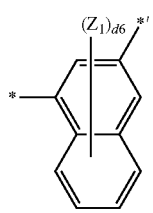 Formula 3-33
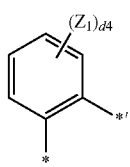 Formula 3-34
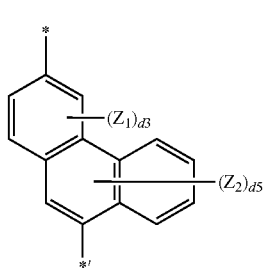 Formula 3-35
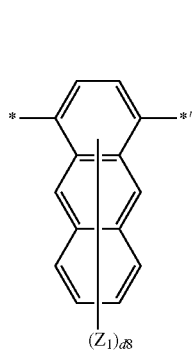 Formula 3-36
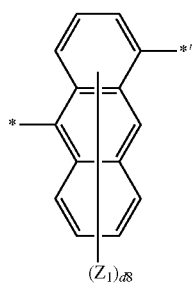 Formula 3-37

-continued

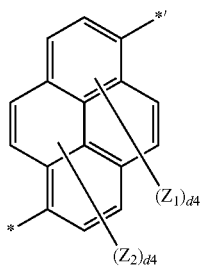
Formula 3-38

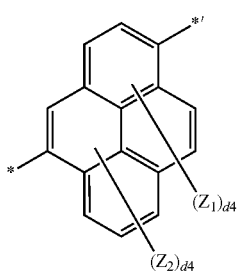
Formula 3-39

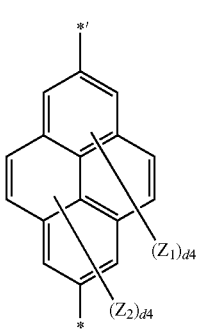
Formula 3-40

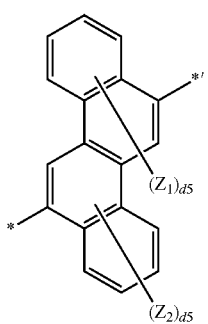
Formula 3-41 wherein, in Formulae 3-1 to 3-41, $Y_1$ is selected from O, S, C($Z_3$)($Z_4$), N($Z_5$), and Si($Z_6$)($Z_7$), and $Z_1$ to $Z_7$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —Si($Q_{31}$)($Q_{32}$)($Q_{33}$), wherein $Q_{31}$ to $Q_{33}$ are each independently selected from a $C_1$-$C_{10}$ alkyl group, a $C_1$-$C_{10}$ alkoxy group, a phenyl group, and a naphthyl group, d2 is an integer selected from 0 to 2, d3 is an integer selected from 0 to 3, d4 is an integer selected from 0 to 4, d5 is an integer selected from 0 to 5, d6 is an integer selected from 0 to 6, d8 is an integer selected from 0 to 8, and

* and *' each independently indicate a binding site to a neighboring atom.

6. The organic light-emitting device of claim 1, wherein $L_1$ and $L_2$ are each independently selected from groups represented by Formulae 4-11, 4-13, 4-27, and 4-29 to 4-35, and $L_{11}$, $L_{12}$, and $L_{501}$ to $L_{503}$ are each independently selected from groups represented by Formulae 4-1 to 4-35:

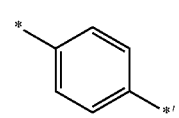
Formula 4-1

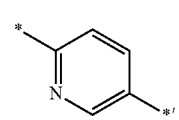
Formula 4-2

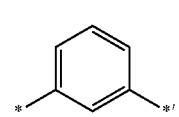
Formula 4-3

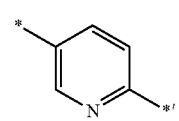
Formula 4-4

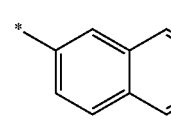
Formula 4-5

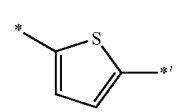
Formula 4-6

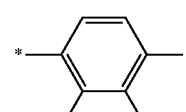
Formula 4-7

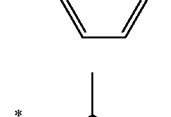
Formula 4-8

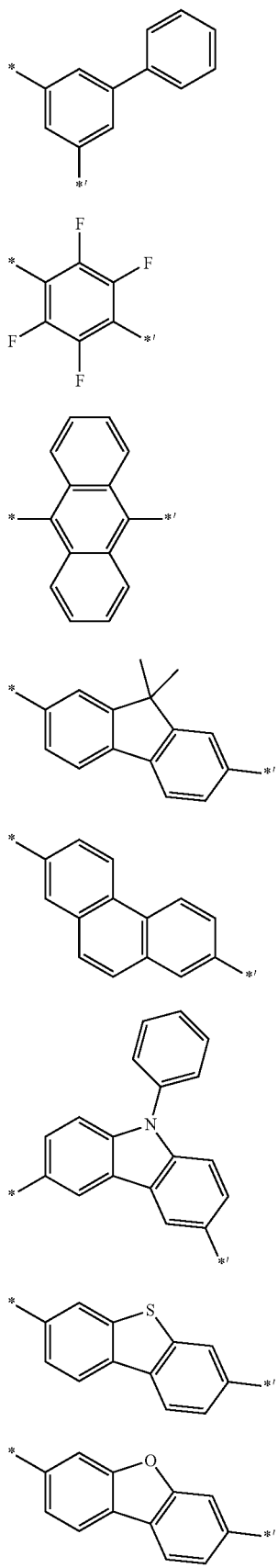

-continued

Formula 4-26
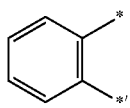

Formula 4-27
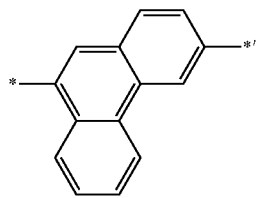

Formula 4-28
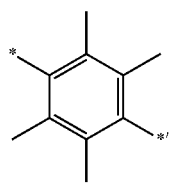

Formula 4-29
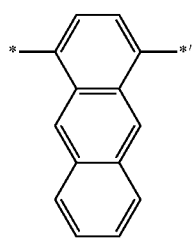

Formula 4-30
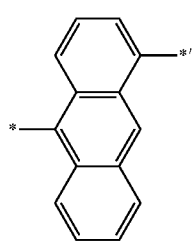

Formula 4-31
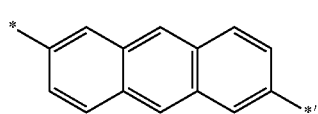

Formula 4-32
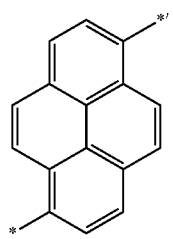

Formula 4-33
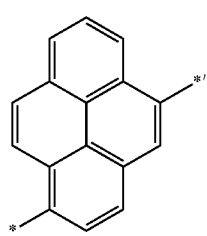

-continued

Formula 4-34
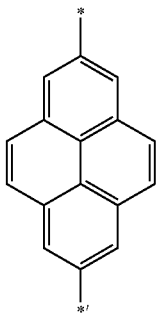

Formula 4-35
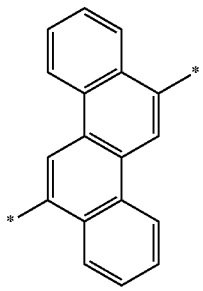

wherein, in Formulae 4-1 and 4-35, * and *' each independently indicate a binding site to a neighboring atom.

7. The organic light-emitting device of claim 1, wherein $R_5$, $R_6$, $R_{11}$ to $R_{13}$, $R_{21}$ to $R_{26}$, $R_{31}$ to $R_{36}$, $R_{501}$, and $R_{502}$ are each independently selected from the group consisting of:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, and a hydrazono group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group a dibenzosilolyl group, a thiadiazolyl group, an imidazopyridinyl group, and an imidazopyrimidinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ are each independently selected from a $C_1$-$C_{10}$ alkyl group, a $C_1$-$C_{10}$ alkoxy group, a phenyl group, and a naphthyl group.

8. The organic light-emitting device of claim 1, wherein $R_1$ and $R_2$ are each independently selected from hydrogen, deuterium, —F, —Cl, —Br, —I, a hydroxyl group, a cyano group, a nitro group, an amidino group, a hydrazino group, a hydrazono group, a $C_1$-$C_{10}$ alkyl group, a $C_1$-$C_{10}$ alkoxy group, a group represented by any of Formulae 5-1 to 5-20, and —Si($Q_1$)($Q_2$)($Q_3$), and $R_5$, $R_6$, $R_{11}$ to $R_{13}$, $R_{21}$ to $R_{26}$, $R_{31}$ to $R_{36}$, $R_{501}$, and $R_{502}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{10}$ alkyl group, a $C_1$-$C_{10}$ alkoxy group, a group represented by any of Formulae 5-1 to 5-75, and —Si($Q_1$)($Q_2$)($Q_3$), wherein $Q_1$ to $Q_3$ are each independently selected from a $C_1$-$C_{10}$ alkyl group, a $C_1$-$C_{10}$ alkoxy group, a phenyl group, and a naphthyl group:

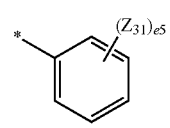

Formula 5-1

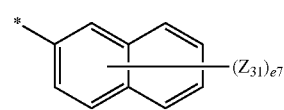

Formula 5-2

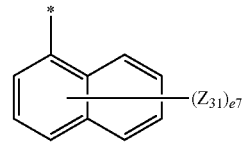

Formula 5-3

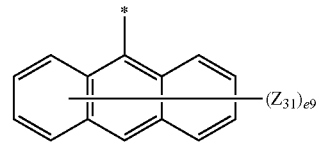

Formula 5-4

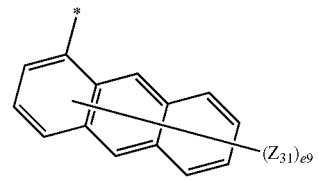

Formula 5-5

-continued
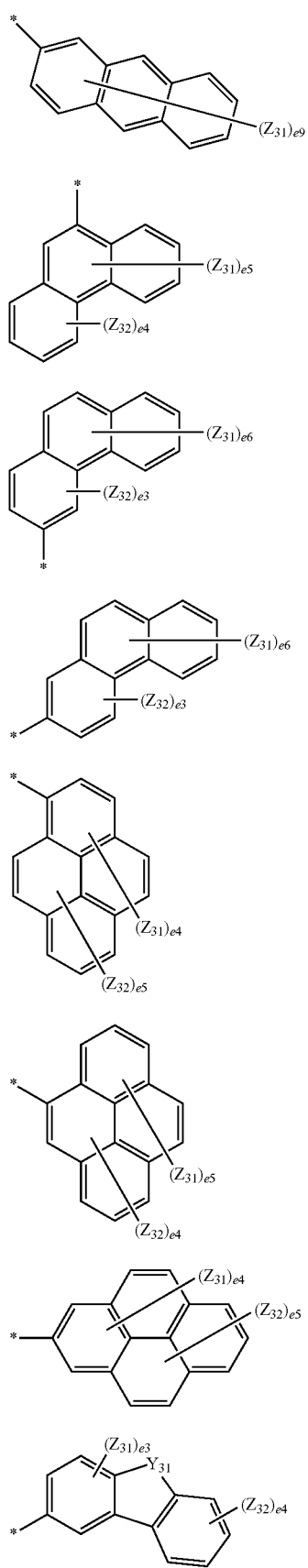
-continued
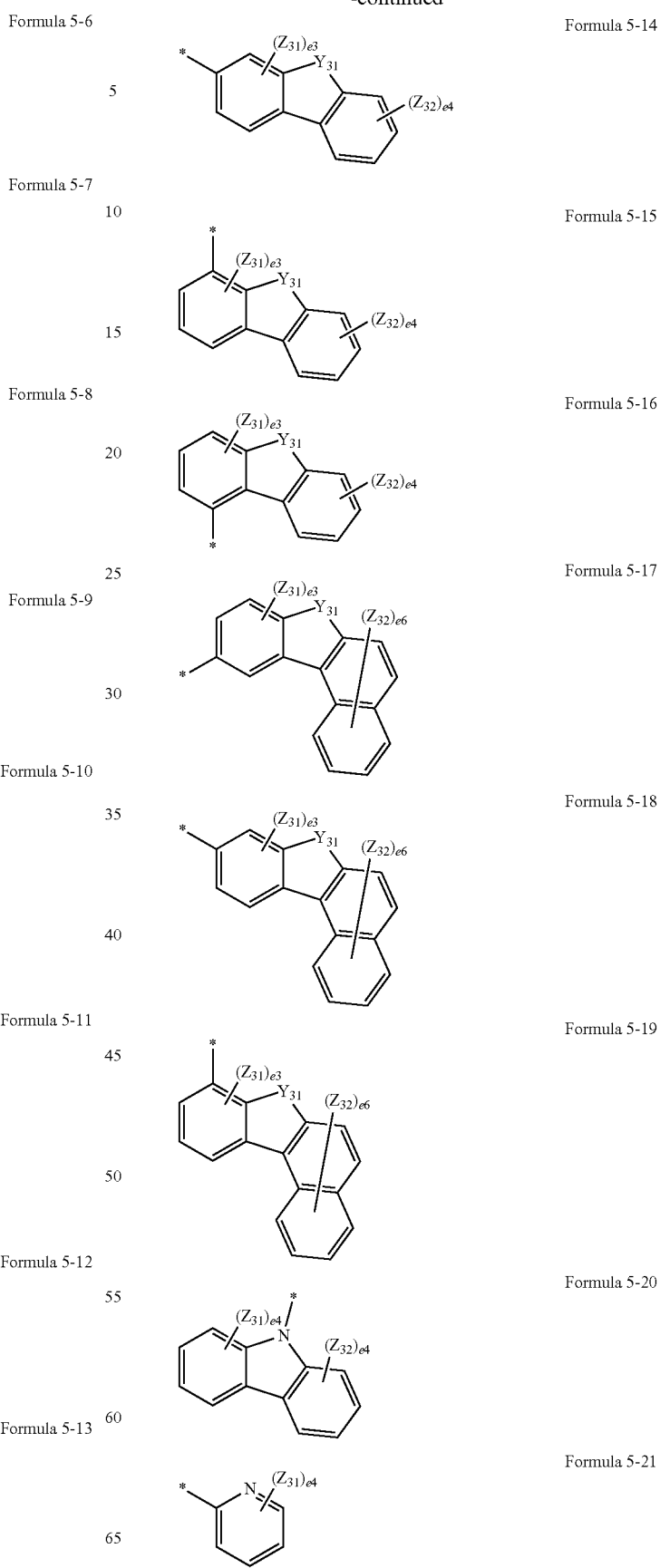

-continued
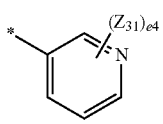 Formula 5-22
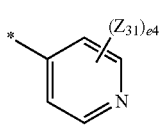 Formula 5-23
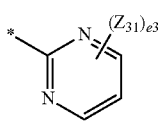 Formula 5-24
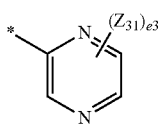 Formula 5-25
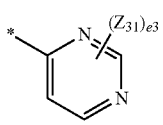 Formula 5-26
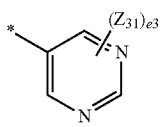 Formula 5-27
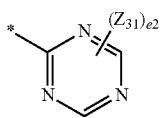 Formula 5-28
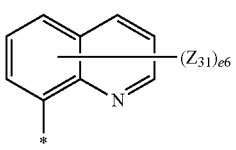 Formula 5-29
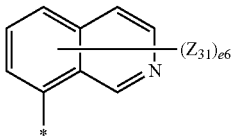 Formula 5-30
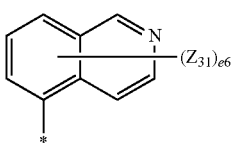 Formula 5-31
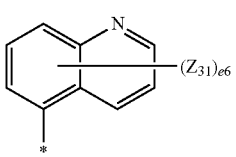 Formula 5-32
-continued
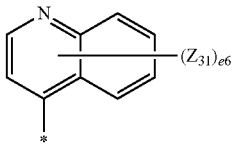 Formula 5-33
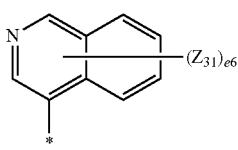 Formula 5-34
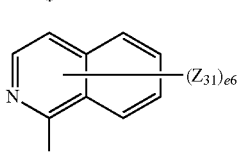 Formula 5-35
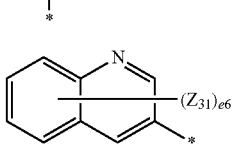 Formula 5-36
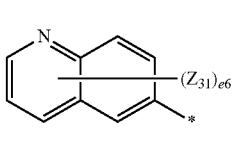 Formula 5-37
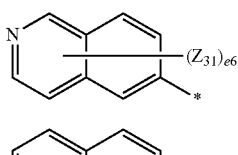 Formula 5-38
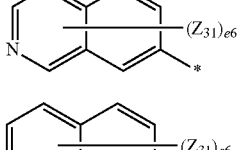 Formula 5-39
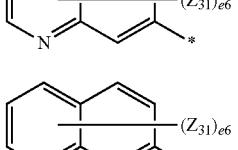 Formula 5-40
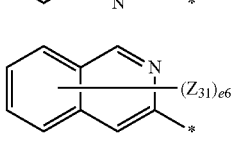 Formula 5-41
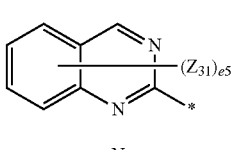 Formula 5-42
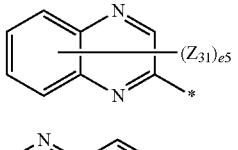 Formula 5-43
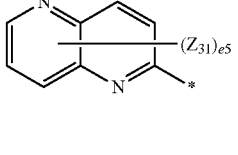 Formula 5-44
Formula 5-45

Formula 5-46
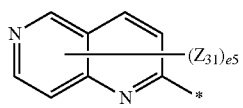
Formula 5-47
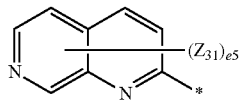
Formula 5-48
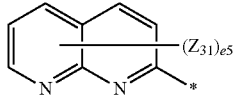
Formula 5-49
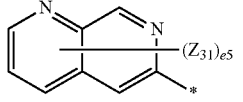
Formula 5-50
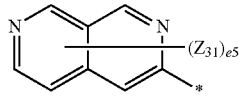
Formula 5-51
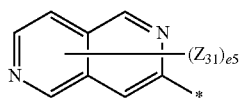
Formula 5-52
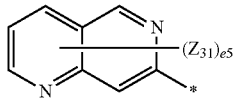
Formula 5-53
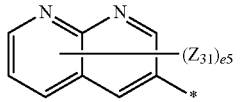
Formula 5-54
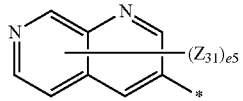
Formula 5-55
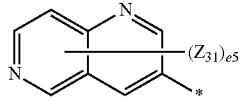
Formula 5-56
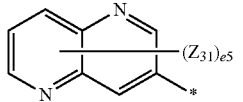
Formula 5-57
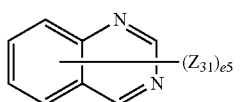
Formula 5-58
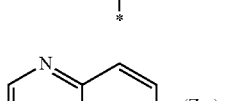
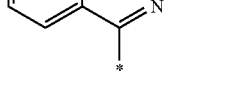
Formula 5-59
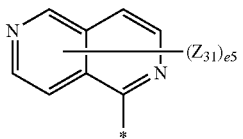
Formula 5-60
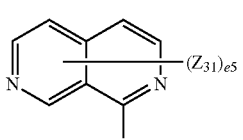
Formula 5-61
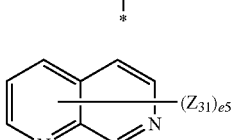
Formula 5-62
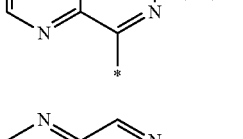
Formula 5-63
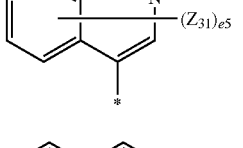
Formula 5-64
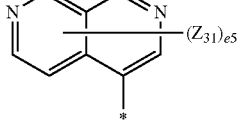
Formula 5-65
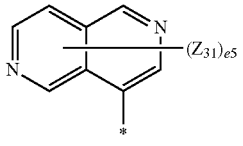
Formula 5-66
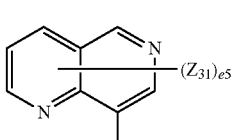
Formula 5-67
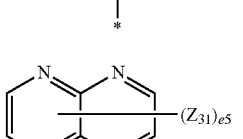
Formula 5-68
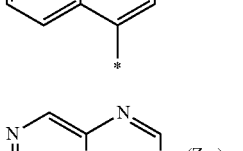

-continued

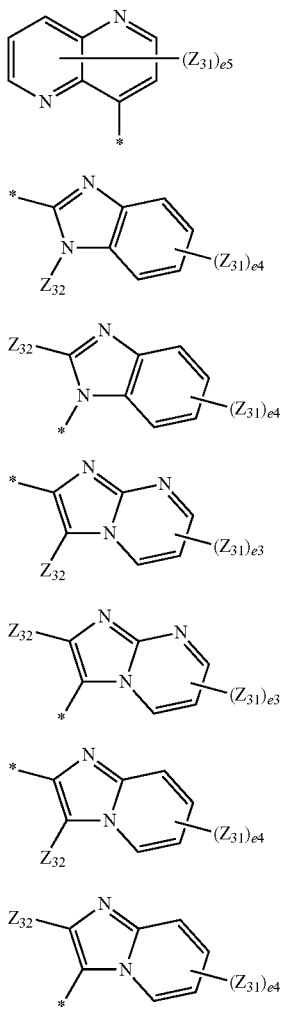

wherein, in Formulae 5-1 to 5-75,
Y$_{31}$ is selected from O, S, C(Z$_{33}$)(Z$_{34}$), N(Z$_{35}$), and Si(Z$_{36}$)(Z$_{37}$),
Z$_{31}$ to Z$_{37}$ are each independently selected from hydrogen, deuterium, —F, —Cl, —Br, —I, a hydroxyl group, a cyano group, a nitro group, an amidino group, a hydrazino group, a hydrazono group, a C$_1$-C$_{20}$ alkyl group, a C$_1$-C$_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a biphenyl group, a terphenyl group, and —Si(Q$_{31}$)(Q$_{32}$)(Q$_{33}$),
wherein Q$_{31}$ to Q$_{33}$ are each independently selected from a C$_1$-C$_{10}$ alkyl group, a C$_1$-C$_{10}$ alkoxy group, a phenyl group, and a naphthyl group,
e2 is an integer selected from 0 to 2,
e3 is an integer selected from 0 to 3,
e4 is an integer selected from 0 to 4,
e5 is an integer selected from 0 to 5,
e6 is an integer selected from 0 to 6,
e7 is an integer selected from 0 to 7,
e9 is an integer selected from 0 to 9, and
* indicates a binding site to a neighboring atom.

9. The organic light-emitting device of claim 1, wherein
R$_5$, R$_6$, R$_{21}$ to R$_{26}$, R$_{31}$ to R$_{36}$, and R$_{13}$ are each independently selected from hydrogen, deuterium, —F, —Cl, —Br, —I, a hydroxyl group, a cyano group, a nitro group, an amidino group, a hydrazino group, a hydrazono group, a C$_1$-C$_{10}$ alkyl group, a C$_1$-C$_{10}$ alkoxy group, a phenyl group, a naphthyl group, and —Si(Q$_1$)(Q$_2$)(Q$_3$), wherein Q$_1$ to Q$_3$ are each independently selected from a C$_1$-C$_{10}$ alkyl group, a C$_1$-C$_{10}$ alkoxy group, a phenyl group, and a naphthyl group,
R$_{11}$, R$_{12}$, R$_{501}$, and R$_{502}$ are each independently selected from groups represented by Formulae 6-1 to 6-43 and groups represented by Formulae 10-1 to 10-117, and
R$_1$ and R$_2$ are each independently selected from groups represented by Formulae 6-1 to 6-43:

Formula 6-1
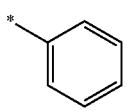

Formula 6-2
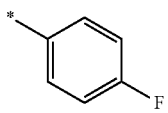

Formula 6-3
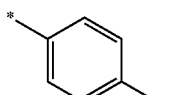

Formula 6-4
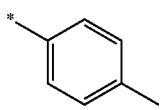

Formula 6-5
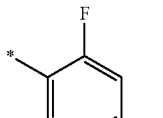

Formula 6-6
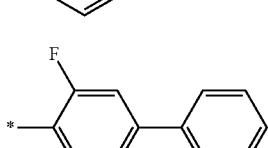

Formula 6-7
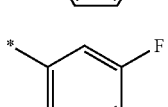

Formula 6-8
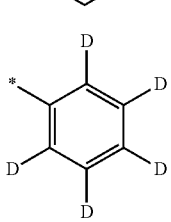

-continued
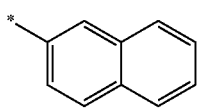
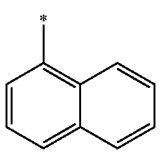
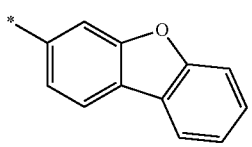
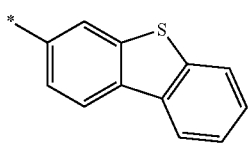
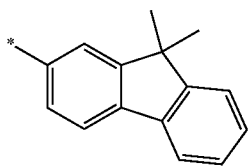
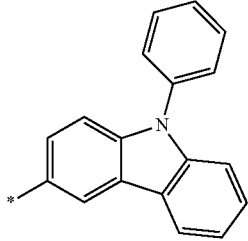
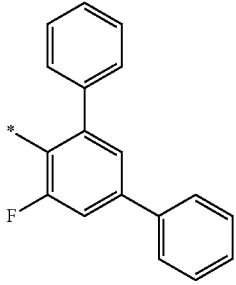
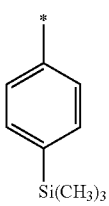
-continued
Formula 6-9
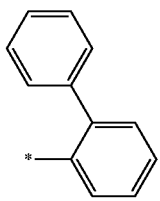
Formula 6-10
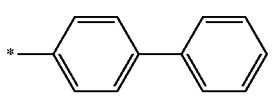
Formula 6-11
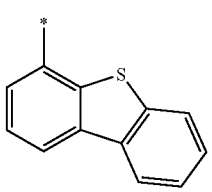
Formula 6-12
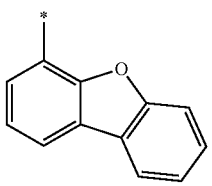
Formula 6-13
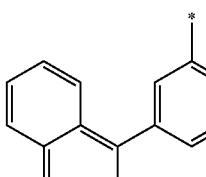
Formula 6-14
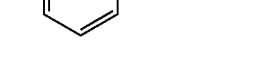
Formula 6-15
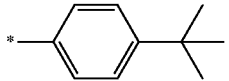
Formula 6-16
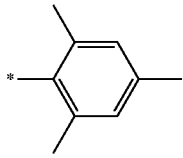
Formula 6-17
Formula 6-18
Formula 6-19
Formula 6-20
Formula 6-21
Formula 6-22
Formula 6-23
Formula 6-24
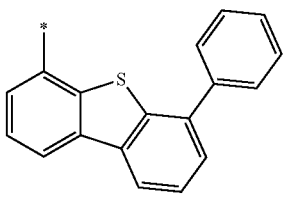
Formula 6-25
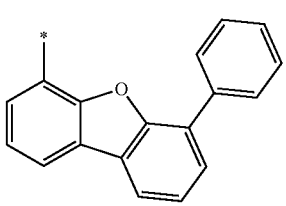

Formula 6-26

Formula 6-27

Formula 6-28

Formula 6-29

Formula 6-30

Formula 6-31

Formula 6-32

Formula 6-33

Formula 6-34

Formula 6-35

Formula 6-36

Formula 6-37

Formula 6-38

Formula 6-39

Formula 6-40

Formula 6-41

Formula 6-42

Formula 6-43

Formula 10-1

-continued
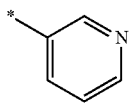
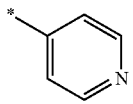
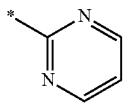
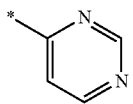
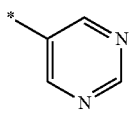
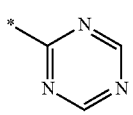
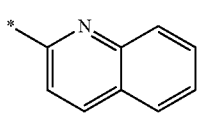
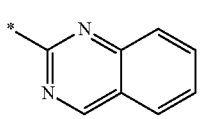
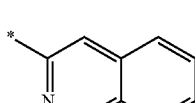
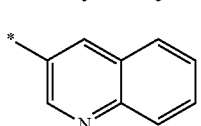
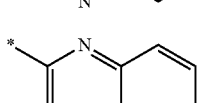
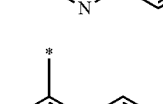
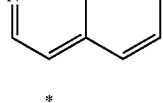
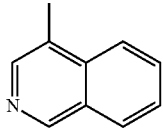
-continued
Formula 10-2
Formula 10-3
Formula 10-4
Formula 10-5
Formula 10-6
Formula 10-7
Formula 10-8
Formula 10-9
Formula 10-10
Formula 10-11
Formula 10-12
Formula 10-13
Formula 10-14
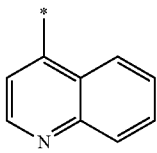
Formula 10-15
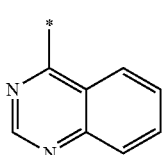
Formula 10-16
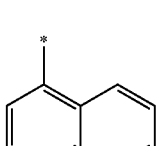
Formula 10-17
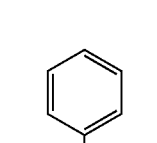
Formula 10-18
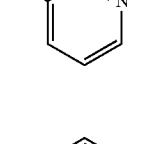
Formula 10-19
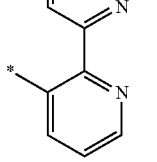
Formula 10-20
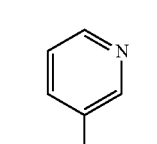
Formula 10-21
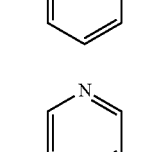
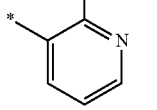

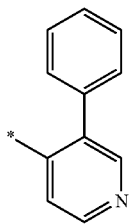
Formula 10-22
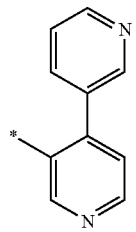
Formula 10-28
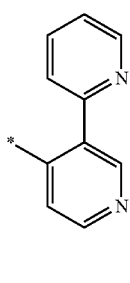
Formula 10-23
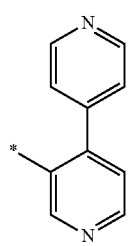
Formula 10-29
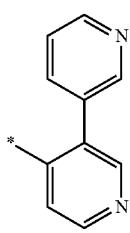
Formula 10-24
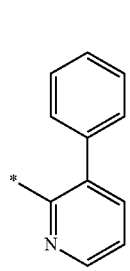
Formula 10-30
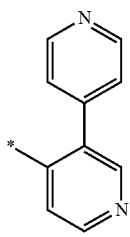
Formula 10-25
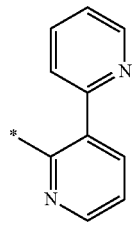
Formula 10-31
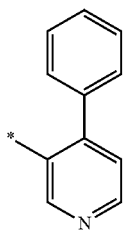
Formula 10-26
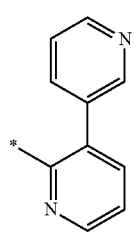
Formula 10-32
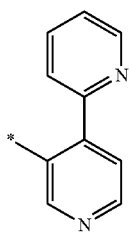
Formula 10-27
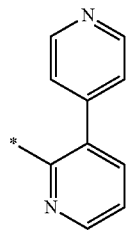
Formula 10-33

-continued
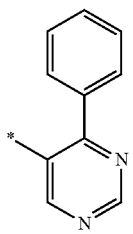
Formula 10-34
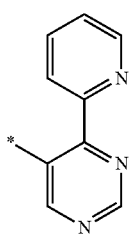
Formula 10-35
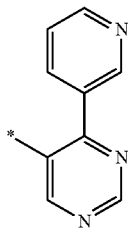
Formula 10-36
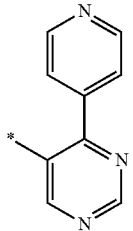
Formula 10-37
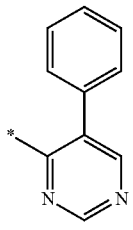
Formula 10-38
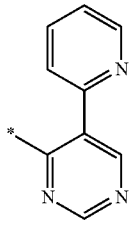
Formula 10-39
-continued
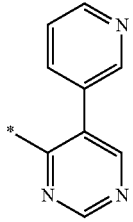
Formula 10-40
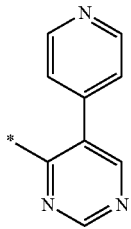
Formula 10-41
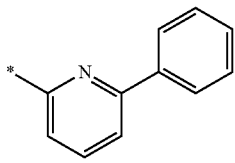
Formula 10-42
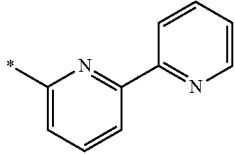
Formula 10-43
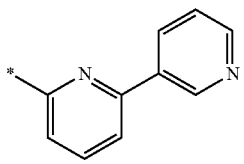
Formula 10-44
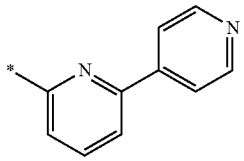
Formula 10-45
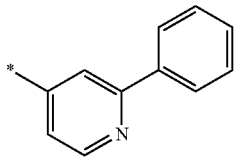
Formula 10-46
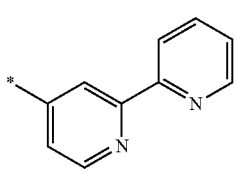
Formula 10-47

Formula 10-48
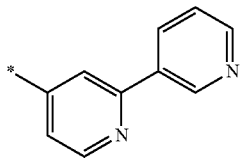
Formula 10-49
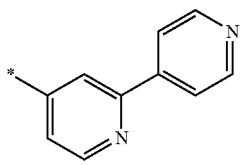
Formula 10-50
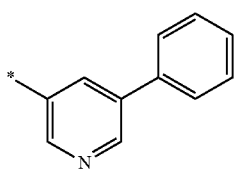
Formula 10-51
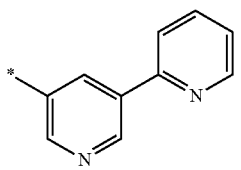
Formula 10-52
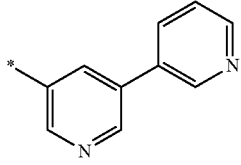
Formula 10-53
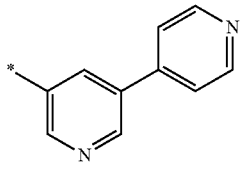
Formula 10-54
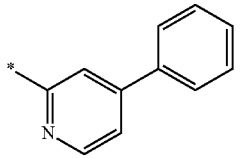
Formula 10-55
Formula 10-56
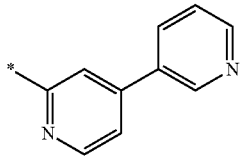
Formula 10-57
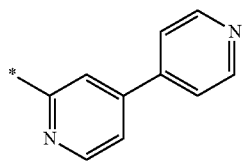
Formula 10-58
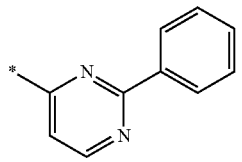
Formula 10-59
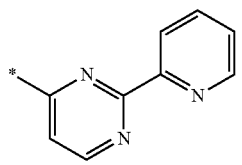
Formula 10-60
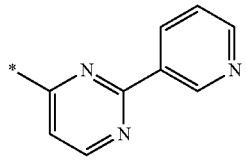
Formula 10-61
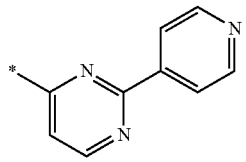
Formula 10-62
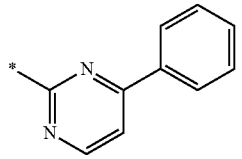
Formula 10-63
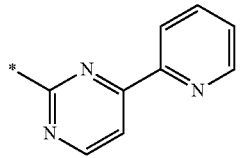
Formula 10-64
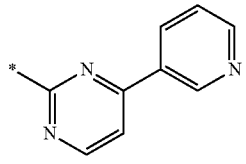
Formula 10-65
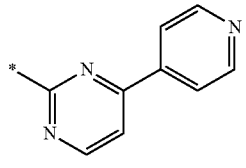

-continued
Formula 10-66
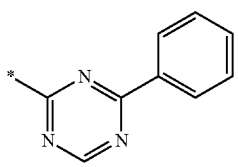
Formula 10-67
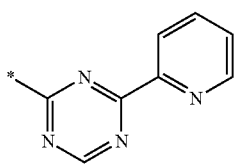
Formula 10-68
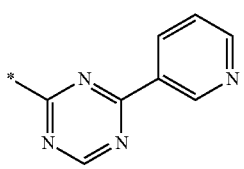
Formula 10-69
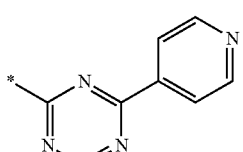
Formula 10-70
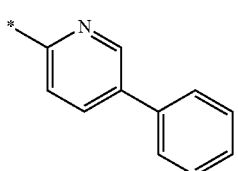
Formula 10-71
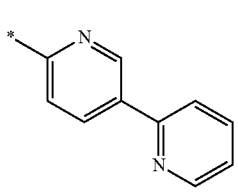
Formula 10-72
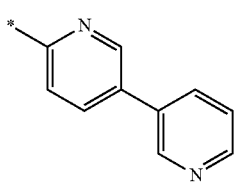
Formula 10-73
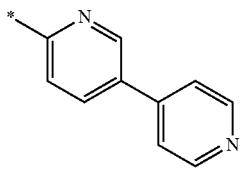
Formula 10-74
-continued
Formula 10-75
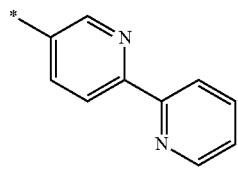
Formula 10-76
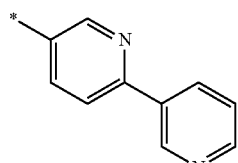
Formula 10-77
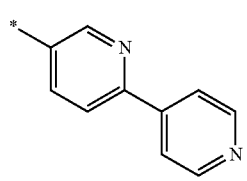
Formula 10-78
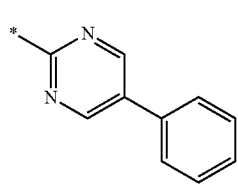
Formula 10-79
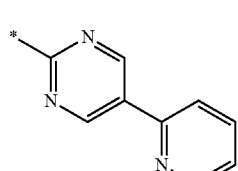
Formula 10-80
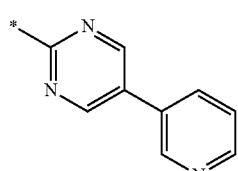
Formula 10-81
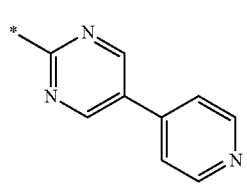
Formula 10-82
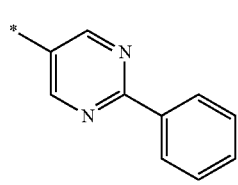
Formula 10-83
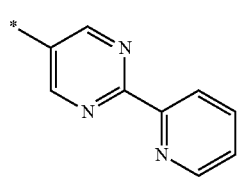

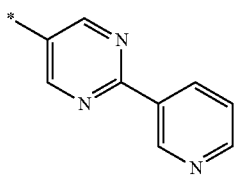
Formula 10-84
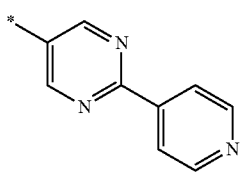
Formula 10-85
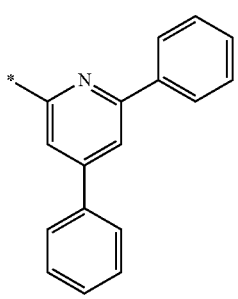
Formula 10-86
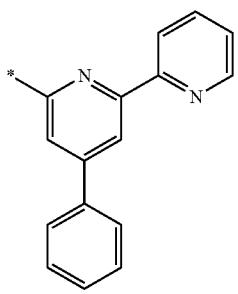
Formula 10-87
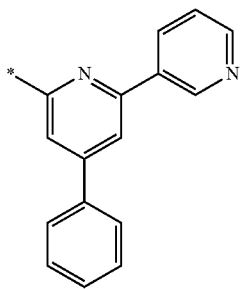
Formula 10-88
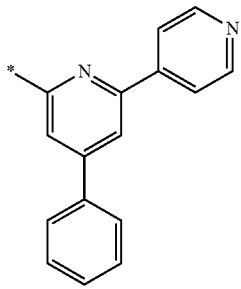
Formula 10-89
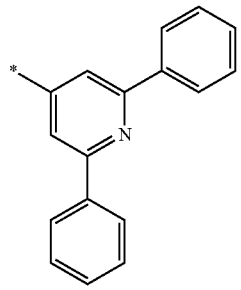
Formula 10-90
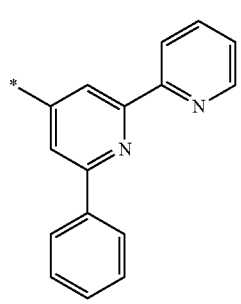
Formula 10-91
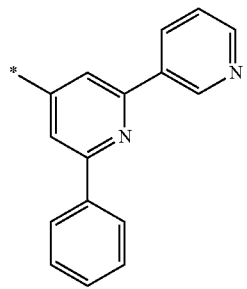
Formula 10-92
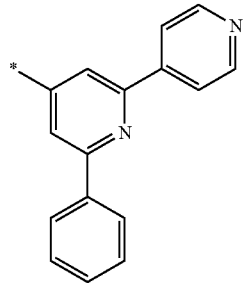
Formula 10-93
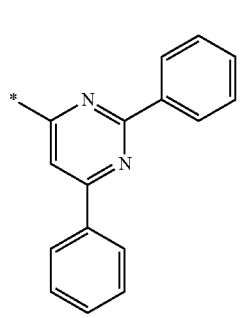
Formula 10-94

Formula 10-95

Formula 10-96

Formula 10-97

Formula 10-98

Formula 10-99

Formula 10-100

Formula 10-101

Formula 10-102

Formula 10-103

Formula 10-104

Formula 10-105
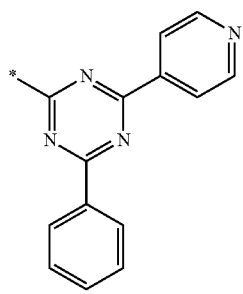

Formula 10-106
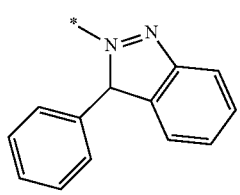

Formula 10-107
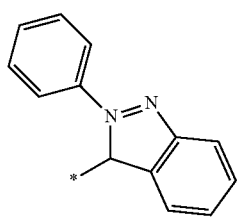

Formula 10-108
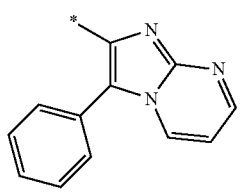

Formula 10-109
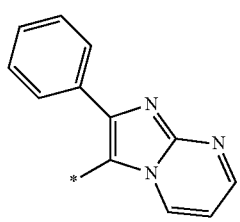

Formula 10-110
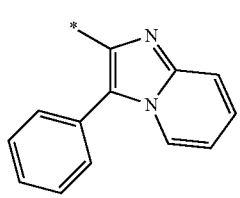

Formula 10-111
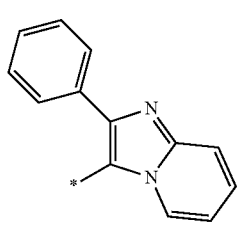

Formula 10-112
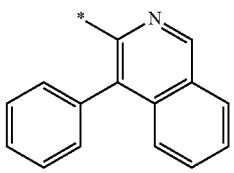

Formula 10-113
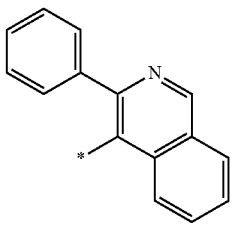

Formula 10-114
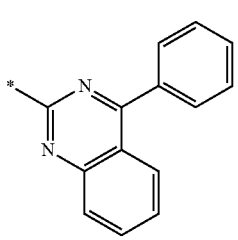

Formula 10-115
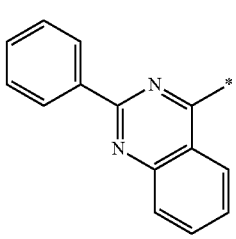

Formula 10-116
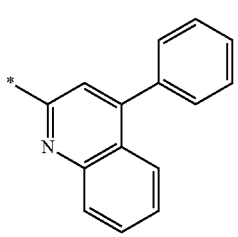

Formula 10-117
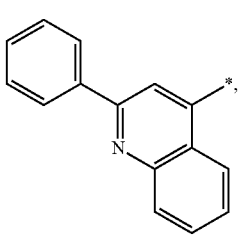, wherein, in Formulae 6-1 to 6-43 and 10-1 to 10-117, * indicates a binding site to a neighboring atom.

10. The organic light-emitting device of claim 1, wherein c1 is 1 and c2 is 0, and
xd4 is 2, 3, or 4.

11. The organic light-emitting device of claim 1, wherein the first compound is represented by one selected from Formulae 1(3), 1(6), 1(7), and 1(9) to 1(24):

Formula 1(3)
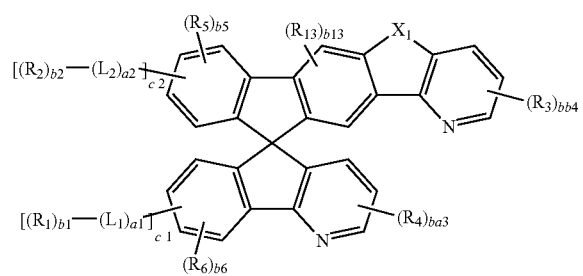
Formula 1(6)
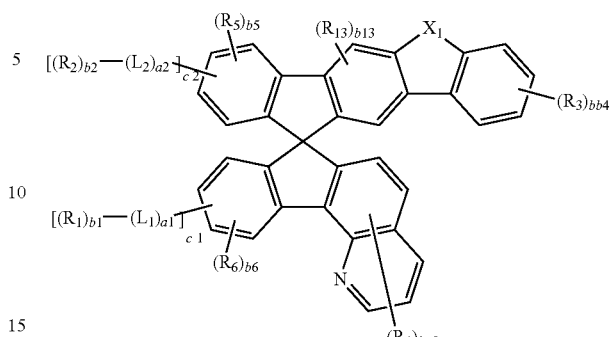
Formula 1(7)
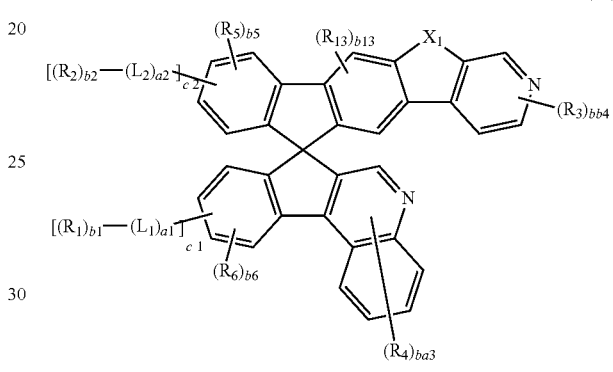
Formula 1(9)
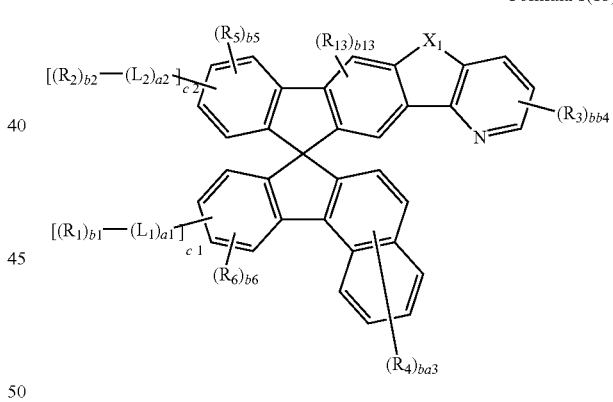
Formula 1(10)
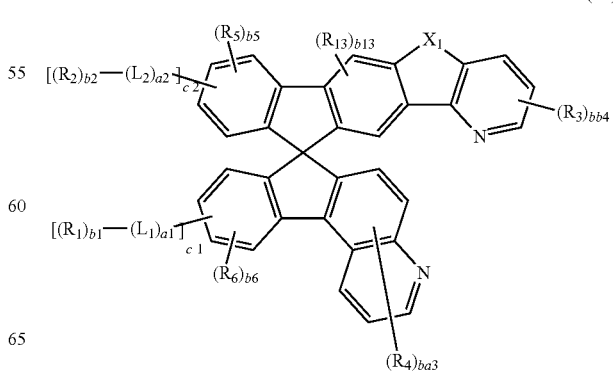
-continued
Formula 1(11)
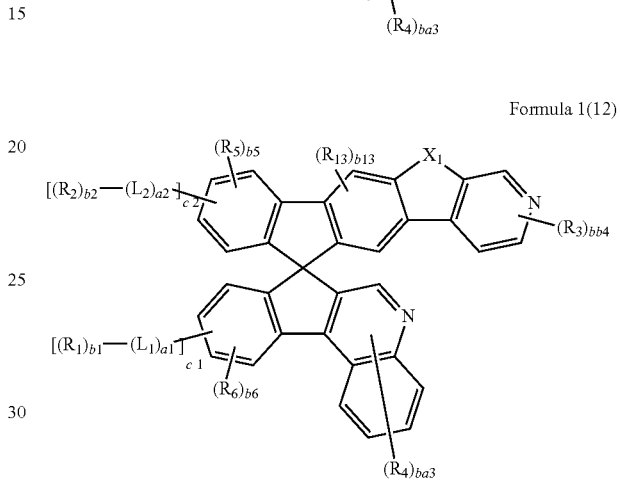
Formula 1(12)
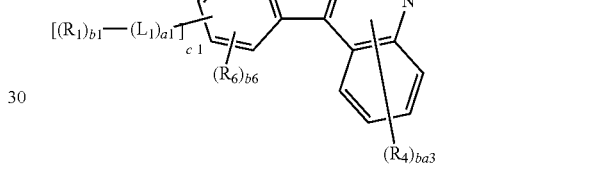
Formula 1(13)
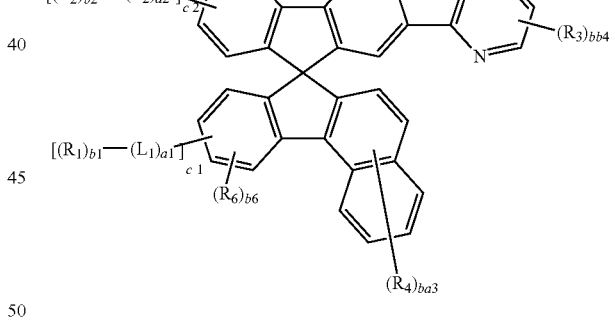
Formula 1(14)
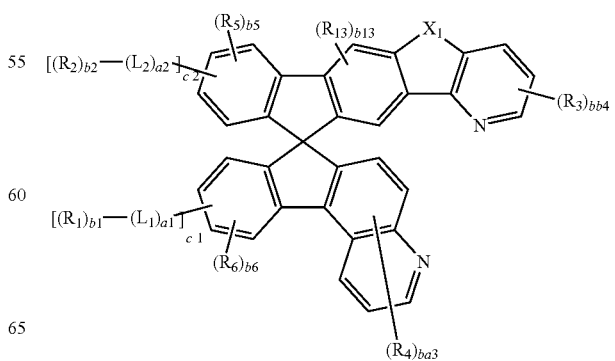

Formula 1(15)
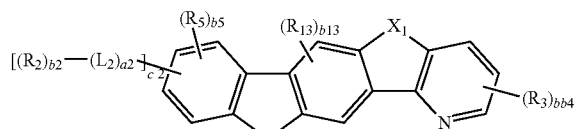
Formula 1(16)
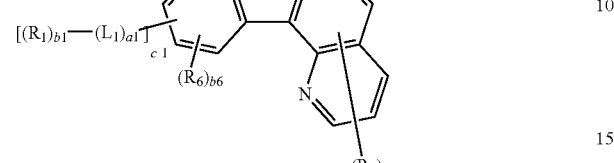
Formula 1(17)
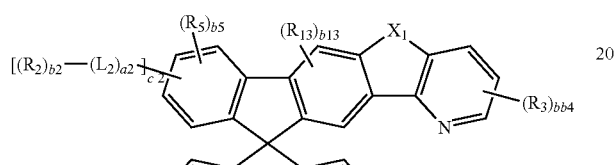
Formula 1(18)
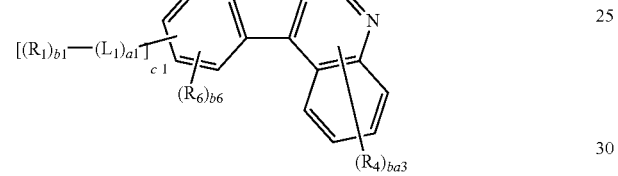
Formula 1(19)
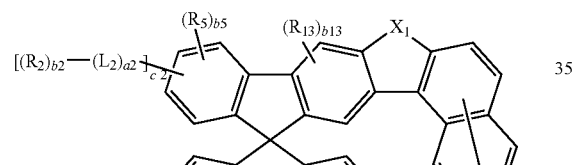
Formula 1(20)
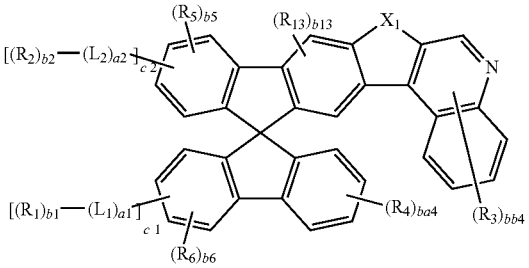
Formula 1(21)
Formula 1(22)
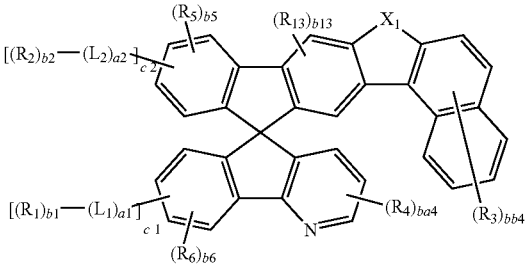
Formula 1(23)
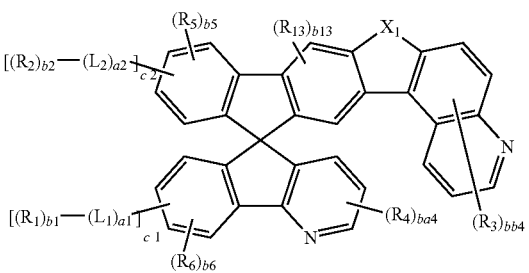
Formula 1(24)
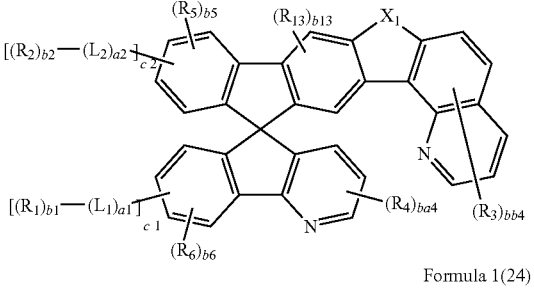
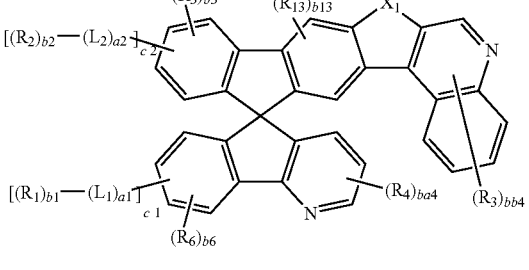
wherein, in Formulae 1(3), 1(6), 1(7), and 1(9) to 1(24),
ba3 and bb3 are each independently an integer selected from 0 to 3,
ba4 is an integer selected from 0 to 4,
ba5 and bb5 are each independently an integer selected from 0 to 5, and ba6 and bb6 are each independently an integer selected from 0 to 6,
provided that $L_1$ and $L_2$ in Formulae 1(9) to 1(11), and 1(17) are not each independently a substituted or unsubstituted anthracenylene group.

12. An organic light-emitting device comprising:
a first electrode;
a second electrode facing the first electrode; and
an organic layer between the first electrode and the second electrode, the organic layer comprising an emission layer,
wherein the organic layer comprises a first compound represented by one selected from Formulae 1A-2 and 1A-3 and a second compound represented by Formula 501,

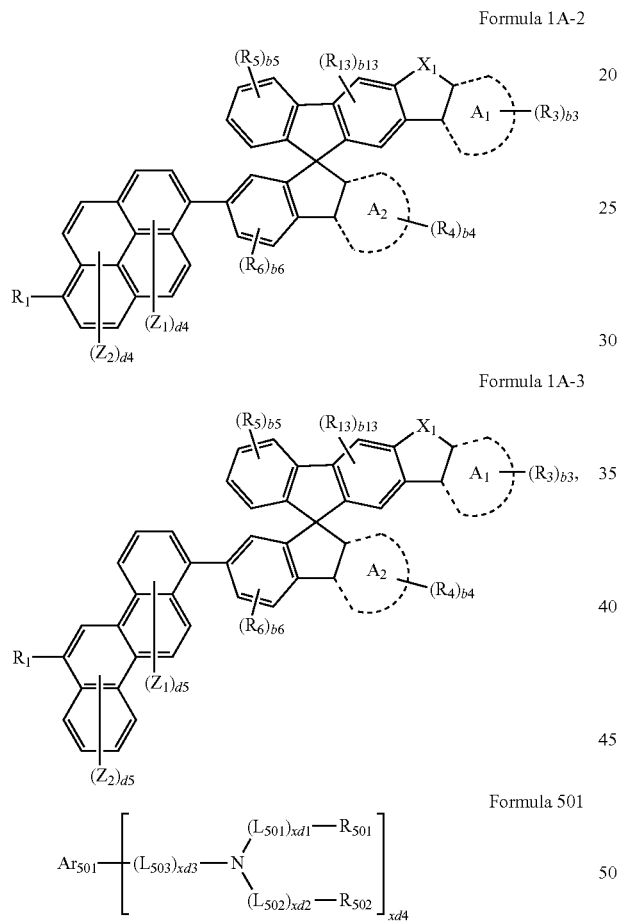

wherein, in Formulae 1A-2 and 1A-3,
ring $A_1$ is a naphthalene ring, a quinoline ring, or an isoquinoline ring, and ring $A_2$ is a benzene ring or a pyridine ring, or
ring $A_1$ is a benzene ring or a pyridine ring, and ring $A_2$ is a naphthalene ring, a quinoline ring, or an isoquinoline ring,
$X_1$ is O or S,
$R_1$ is selected from groups represented by Formulae 5-1 to 5-20,
$R_3$ to $R_6$, $R_{13}$, $Z_1$, and $Z_2$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, and a naphthyl group,
b3 to b6, b13, d4, and d5 are each independently 0, 1, or 2:

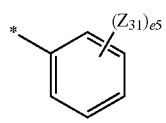

Formula 5-1

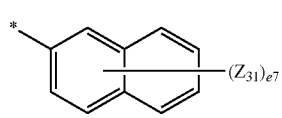

Formula 5-2

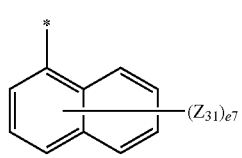

Formula 5-3

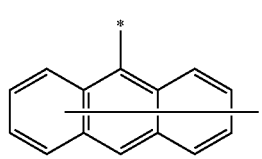

Formula 5-4

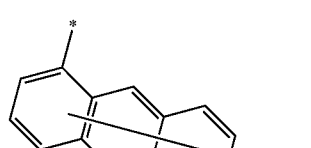

Formula 5-5

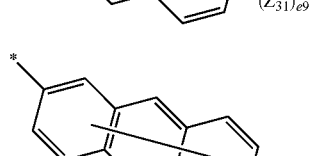

Formula 5-6

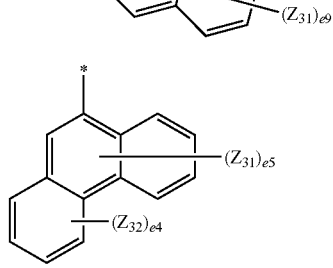

Formula 5-7

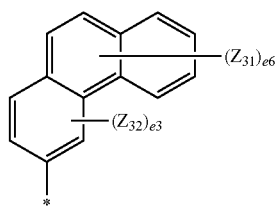

Formula 5-8

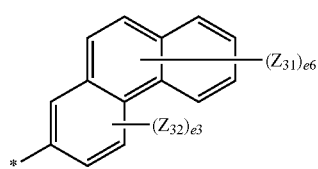

Formula 5-9

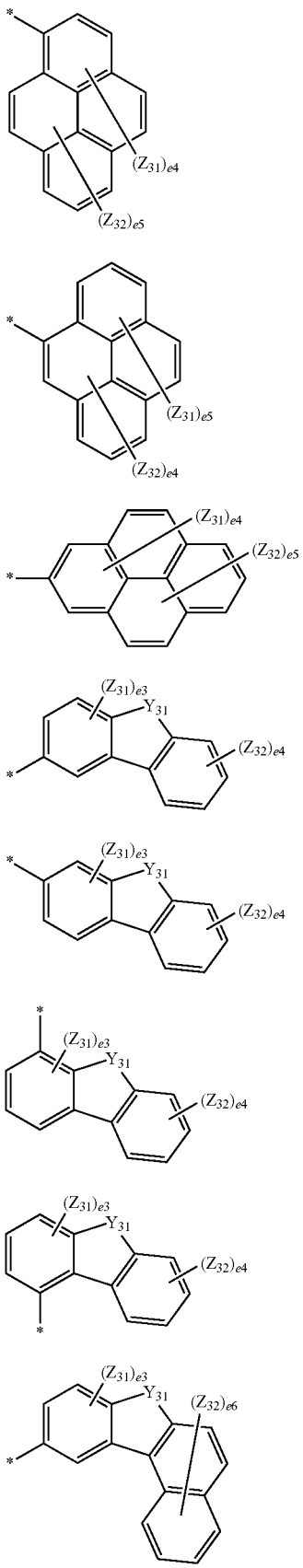

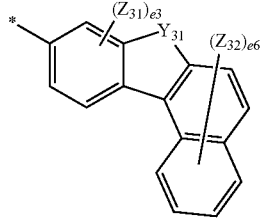

Formula 5-18

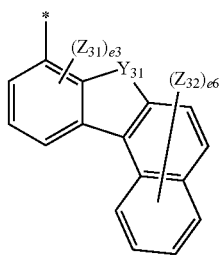

Formula 5-19

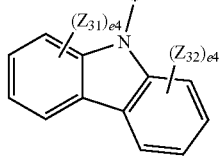

Formula 5-20 wherein, in Formulae 5-1 to 5-20, $Y_{31}$ is selected from O, S, $C(Z_{33})(Z_{34})$, $N(Z_{35})$, and $Si(Z_{36})(Z_{37})$;

$Z_{31}$ to $Z_{37}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a biphenyl group, a terphenyl group, and —$Si(Q_{31})(Q_{32})(Q_{33})$, wherein $Q_{31}$ to $Q_{33}$ are each independently selected from a $C_1$-$C_{10}$ alkyl group, a $C_1$-$C_{10}$ alkoxy group, a phenyl group, and a naphthyl group, e2 is an integer selected from 0 to 2,
e3 is an integer selected from 0 to 3,
e4 is an integer selected from 0 to 4,
e5 is an integer selected from 0 to 5,
e6 is an integer selected from 0 to 6,
e7 is an integer selected from 0 to 7,
e8 is an integer selected from 0 to 8, and
e9 is an integer selected from 0 to 9, and
wherein in Formula 501, $Ar_{501}$ is selected from a substituted or unsubstituted $C_5$-$C_{30}$ carbocyclic group and a substituted or unsubstituted $C_2$-$C_{30}$ heterocyclic group, provided that $Ar_{501}$ is not a pyrene group, and
provided that when $Ar_{501}$ is at least one selected from a fluorene group, a spiro-bifluorene group, a benzofluorene group, a dibenzofluorene group, a phenanthrene group, an anthracene group, a fluoranthene group, a chrysene group, a naphthacene group, and a coronene group, then at least two selected from among $R_{501}$ and $R_{502}$ are substituted with —F, $L_{501}$ to $L_{503}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xd1 to xd3 are each independently an integer selected from 0 to 5, wherein when xd1 is two or more, two or more $L_{501}(s)$ are identical to or different from each other;

when xd2 is two or more, two or more $L_{502}(s)$ are identical to or different from each other; and when xd3 is two or more, two or more $L_{503}(s)$ are identical to or different from each other, $R_{501}$, and $R_{502}$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), xd4 is an integer selected from 1 to 6, and at least one substituent of the substituted condensed polycyclic group having three or more carbocyclic groups condensed with each other, the substituted $C_5$-$C_{30}$ carbocyclic group, the substituted $C_2$-$C_{30}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{60}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from the group consisting of:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$);

$Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

13. The organic light-emitting device of claim 1, wherein the second compound is represented by one selected from Formulae 501-1 and 501-3:

Formula 501-1

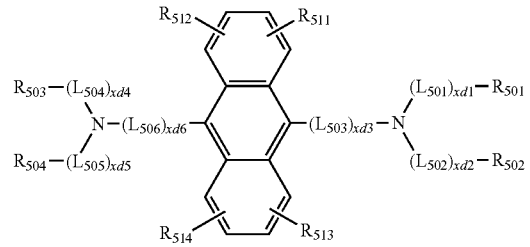

Formula 501-3

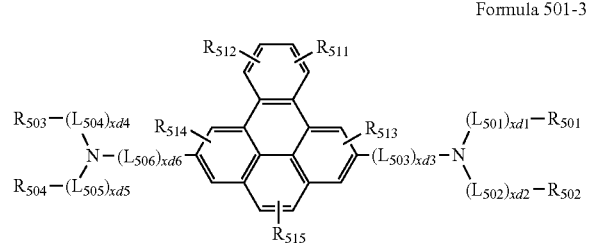

wherein, in Formulae 501-1 and 501-3, descriptions of $L_{501}$ to $L_{503}$, xd1 to xd3, $R_{501}$, and $R_{502}$ are the same as those provided in connection with Formula 501, descriptions of $L_{504}$ to $L_{506}$ are each independently the same as the description provided in connection with $L_{501}$, descriptions of $R_{503}$ and $R_{504}$ are each independently the same as the description provided in connection with $R_{501}$ and $R_{502}$, descriptions of xd4 and xd5 are each independently the same as the description provided in connection with xd1, description of xd6 is the same as the description provided in connection with xd3, and descriptions of $R_{511}$ to $R_{516}$ are each independently the same as the description provided in connection with $R_3$ in Formula 1, and wherein in Formula 501-1, at least two selected from among $R_{501}$ to $R_{504}$ are substituted with —F.

14. An organic light-emitting device comprising:

a first electrode;

a second electrode facing the first electrode; and an organic layer between the first electrode and the second electrode, the organic layer comprising an emission layer, wherein the organic layer comprises a first compound selected from Compounds 3 to 6, 9, 10, 17-24, and 35-38, and a second compound selected from Compounds 101, 104 to 106, and 109:

3

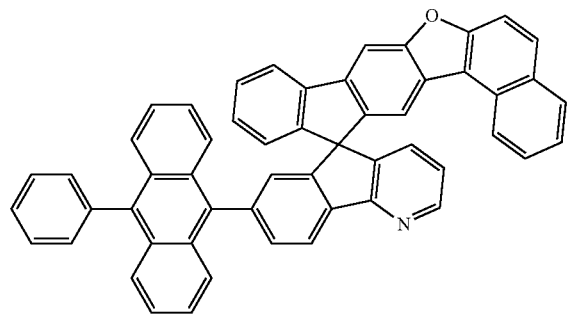

4

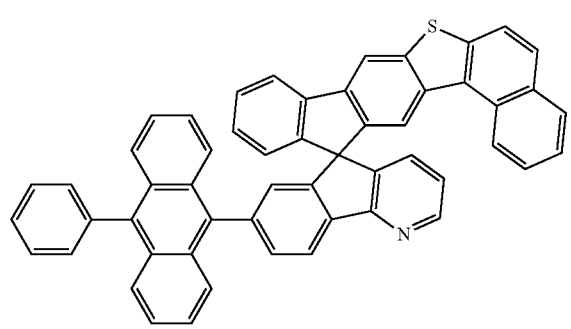

5

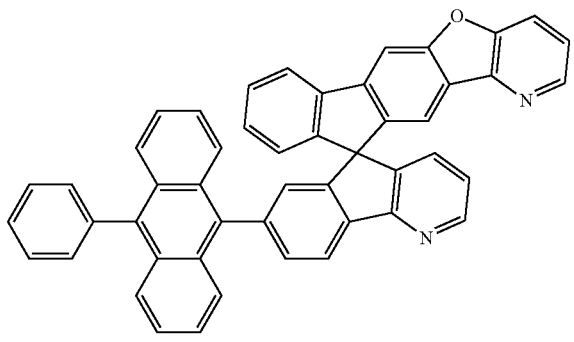

6

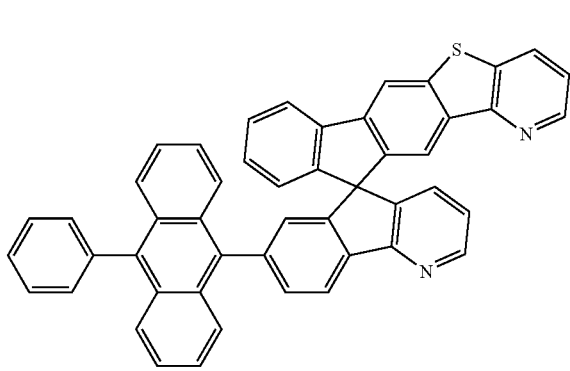

9
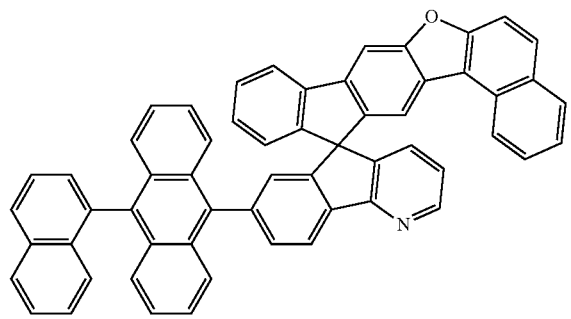
10
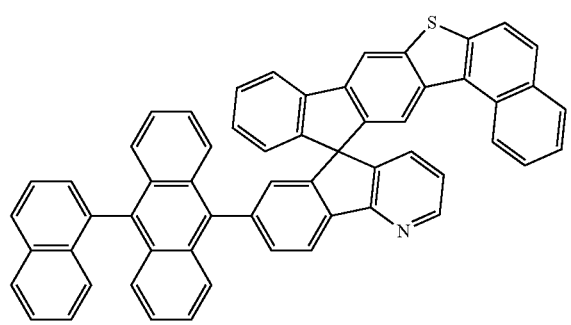
17
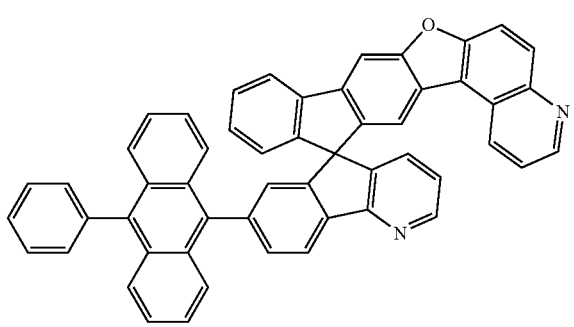
18
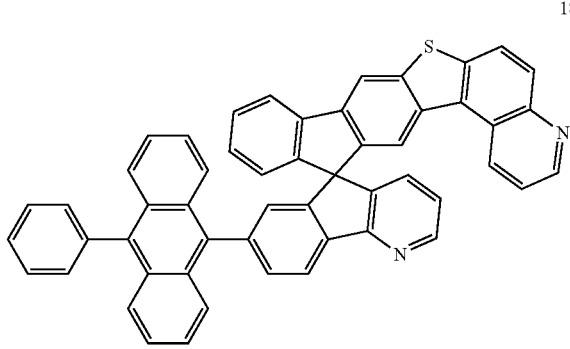
19
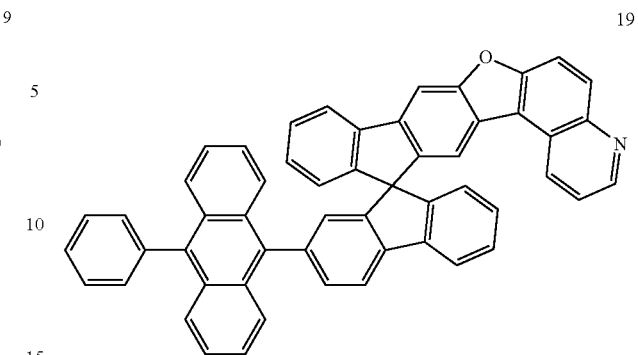
20
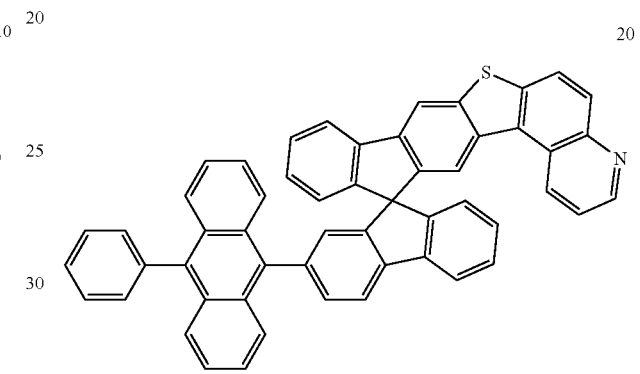
21
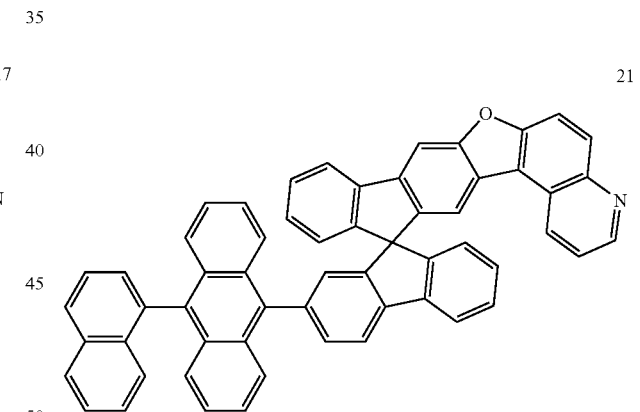
22
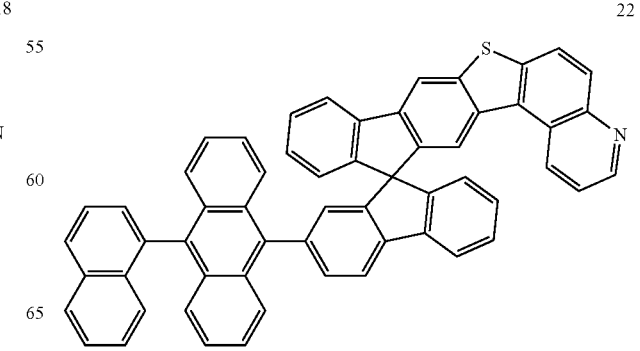

-continued
23
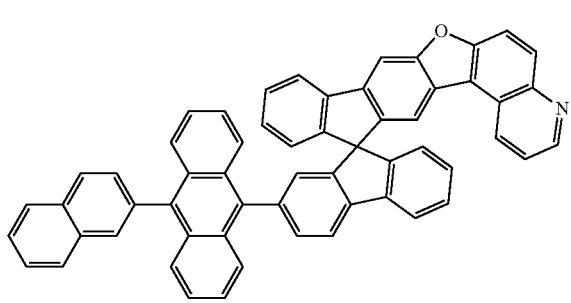
24
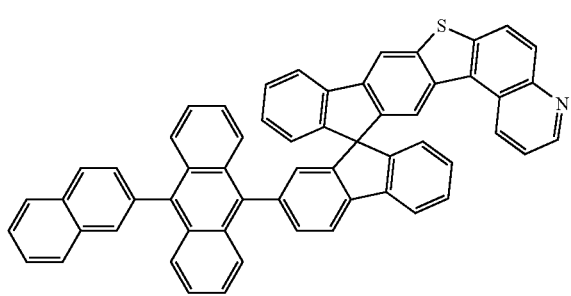
35
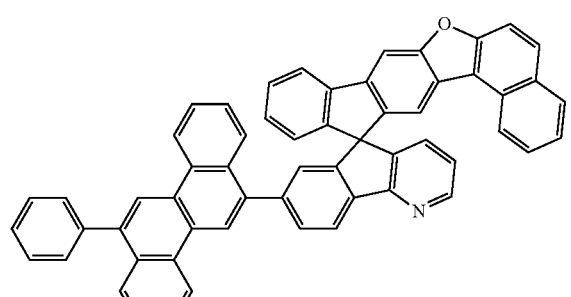
36
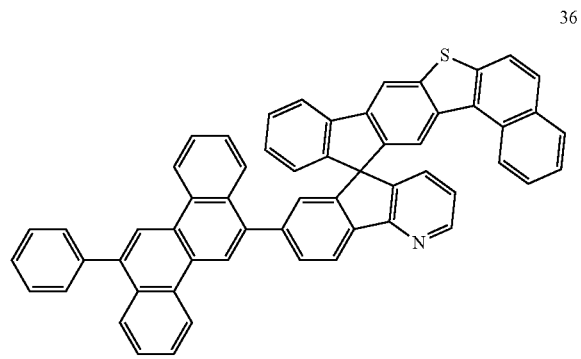 [SMILES: c1ccc(-c2cc3c4ccccc4c(-c4ccc5c(c4)C4(c6ccccc6-c6cc7oc8ccc9ccccc9c8c7cc64)c4cccnc4-5)cc3c3ccccc23)cc1]
37
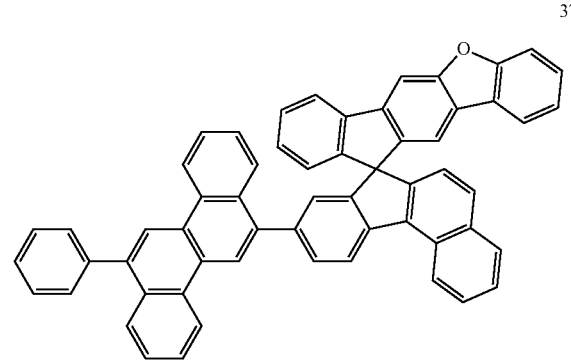
-continued
38
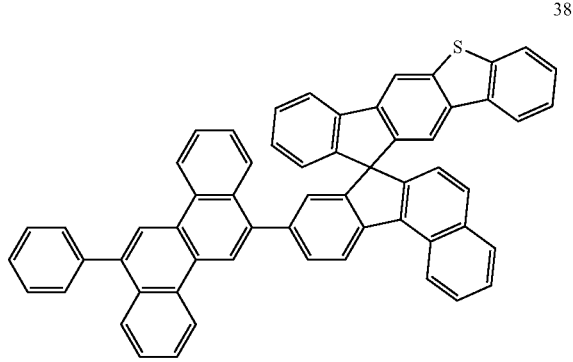
101
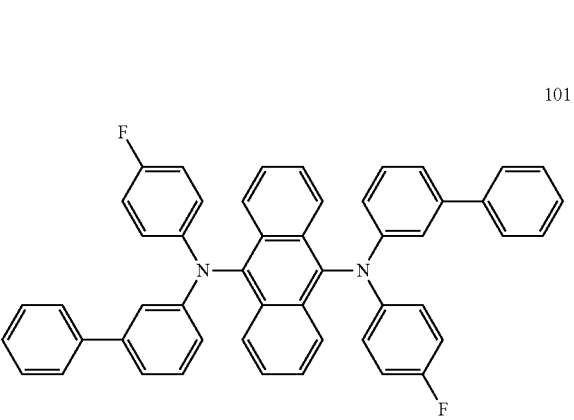
104
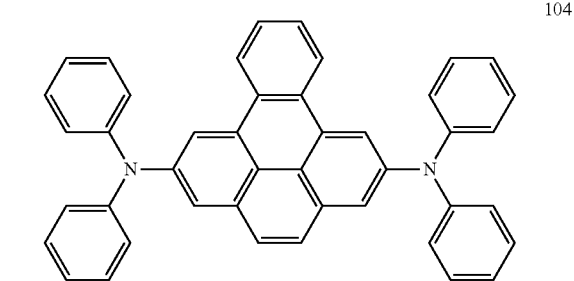
105
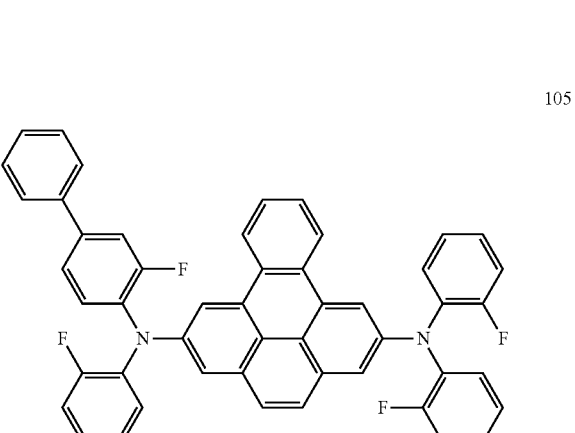

-continued

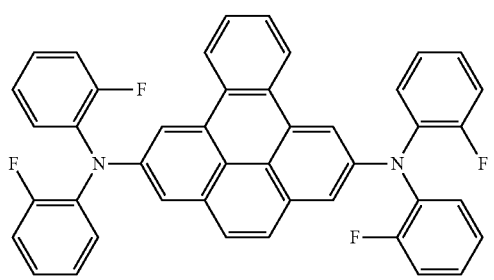
106

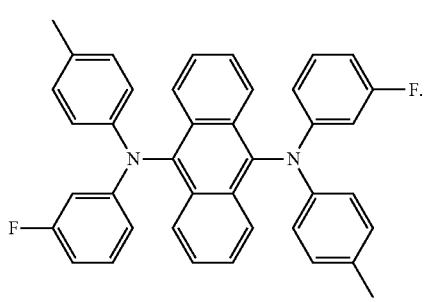
109

15. The organic light-emitting device of claim 1, wherein the emission layer comprises the first compound and the second compound.

16. The organic light-emitting device of claim 15, wherein an amount of the first compound in the emission layer is greater than an amount of the second compound in the emission layer.

17. The organic light-emitting device of claim 1, wherein the first electrode is an anode, the second electrode is a cathode, the organic layer further comprises a hole transport region between the first electrode and the emission layer, and an electron transport region between the emission layer and the second electrode, the hole transport region comprising a hole injection layer, a hole transport layer, an emission auxiliary layer, an electron blocking layer, or a combination thereof, and the electron transport region comprising a hole blocking layer, an electron transport layer, an electron injection layer, or a combination thereof.

* * * * *